United States Patent [19]
Cousens et al.

[11] Patent Number: 5,641,669
[45] Date of Patent: Jun. 24, 1997

[54] PLATELET-ACTIVATING FACTOR ACETYLHYDROLASE

[75] Inventors: Lawrence S. Cousens, Oakland, Calif.; Christine D. Eberhardt, Auburn, Wash.; Patrick Gray; Hai Le Trong, both of Seattle, Wash.; Larry W. Tjoelker, Bothell, Wash.; Cheryl L. Wilder, Bellevue, Wash.

[73] Assignee: ICOS Corporation, Bothell, Wash.

[21] Appl. No.: 318,905

[22] Filed: Oct. 6, 1994

Related U.S. Application Data

[63] Continuation-in-part of Ser. No. 133,803, Oct. 6, 1993.
[51] Int. Cl.[6] ................................................ C12N 9/14
[52] U.S. Cl. ........................ 435/195; 435/7.1; 435/7.2; 435/7.9; 530/300; 530/388.1; 514/2
[58] Field of Search ..................... 435/195, 7.1–7.9; 530/300, 350.1, 388.1; 514/2

[56] References Cited

FOREIGN PATENT DOCUMENTS

| | | |
|---|---|---|
| 9400413 | 1/1994 | United Kingdom . |
| 9313144 | 6/1994 | United Kingdom . |
| 94/20069 | 9/1994 | WIPO . |
| 95/00649 | 1/1995 | WIPO . |

OTHER PUBLICATIONS

Stafforini et al. JBC 262: 4223–4230 1987.
Tarbet et al JBC 266: 16667–16673 1990.
Adjei and Garren, "Pulmonary Delivery of Peptide Drugs: Effect of Particle Size on Bioavailability of Leuprolide Acetate in Healthy Male Volunteers", *Pharm. Res.*, 7(6):565–569 (1990).
Braquet et al., "Effect of Endothelin–1 on Blood Pressure and Bronchopulmonary System of the Guinea Pig", *J. Cardio. Pharm.*, 13(Supp. 5):S143–S146 (1989).
Brenner, "The molecular evolution of genes and proteins: a tale of two serines", *Nature*, 334:528–530 (Aug. 11, 1988).
Capecchi, "Altering the Genome by Homologous Recombination", *Science*, 244:1288–1292 (Jun. 16, 1989).
Chapus et al., "Minireview on pancreatic lipase and colipase", *Biochimie*, 70:1223–1224 (1988).
deBoer et al., "The tac promoter: A functional hybrid derived from the trp and lac promoters", *Proc. Natl. Acad. Sci. USA*, 80:21–25 (Jan. 1983).
Debs et al., "Lung–Specific Delivery of Cytokines Induces Sustained Pulmonary and Systemic Immunomodulation in Rats", *J. Immunol.*, 140(10):3462–3488 (May 15, 1933).
Denizot et al., "PAF–Acether and Acetylhydrolase in Stool of Patients with Crohn's Disease", *Digestive Diseases and Sciences*, 37(3):432–437 (Mar. 1992).
Furukawa et al., "Platelet–Activating Factor–Induced Ischemic Bowel Necrosis: The Effect of Platelet–Activating Factor Acetylhydrolase", *Ped. Res.*, 34(2):237–241 (1993).
Grino et al., "BN 52021: A Platelet Activating Factor Antagonist for Preventing Post–Transplant Renal Failure", *Anna. Int. Med.*, 121(5):345–347 (Sep. 1, 1994).
Handley and Saunders, "Platelet Activating Factor and Inflammation in Atherogenesis: Targets for Drug Development", *Drug. Dev. Res.*, 7:361–375 (1986).
Hattori et al., "Purification and Characterization of Bovine Brain Platelet–activating Factor Acetylhydrolase", *J. Biol. Chem.*, 268(25):18748–18753 (Sep. 5, 1993).
Hattori et al., "The Catalytic Subunit of Bovine Brain Platelet–activating Factor Acetylhydrolase Is a Novel Type of Serine Esterase", *J. Biol. Chem.*, 269(37):23150–23155 (Sep. 16, 1994).

(List continued on next page.)

*Primary Examiner*—Stephanie W. Zitomer
*Assistant Examiner*—Dianne Rees
*Attorney, Agent, or Firm*—Marshall, O'Toole, Gerstein, Murray & Borun

[57] ABSTRACT

The present invention provides purified and isolated polynucleotide sequences encoding human plasma platelet-activating factor acetylhydrolase. Also provided are materials and methods for the recombinant production of platelet-activating factor acetylhydrolase products which are expected to be useful in regulating pathological inflammatory events.

2 Claims, 10 Drawing Sheets

OTHER PUBLICATIONS

Henriques et al., "Endothelin-1 inhibits PAF-induced paw oedema and pleurisy in the mouse", *Br. J. Pharmacol.*, 106:579–582 (1992).

Heuer, "Current status of PAF antagonists", *Clin. Exp. Allergy*, 22:980–983 (1992).

Hoffman et al., "Detection of platelet-activating factor in amniotic fluid of complicated pregnancies", *Am. J. Obstet. Gynecol.*, 162(2):525–528 (1990).

Horwitz et al., "DNA sequences of the araBAD–araC controlling region in *Salmonella typhimurium* LT2", *Gene*, 14:309–319 (1981).

Hsieh and Ng, "Increased plasma platelet-activating factor in children with acute asthmatic attacks and decreased in vivo and in vitro production of platelet-activating factor after immunotherapy", *J. Allergy Clin. Immunol.*, 91:650–657 (Feb. 1993).

Hsueh et al., "Platelet-activating factor, tumor necrosis factor, hypoxia and necrotizing enterocolitis", *Acta P524 diatr., Suppl.* 396:11–17 (1994).

Hubbard et al., "Anti-Neutrophil-Elastase Defenses of the Lower Respiratory Tract in $\alpha$1-Antitrypsin Deficiency Directly Augmented with an Aerosol of A1–Antitrypsin", *Annals of Internal Medicine*, III(3):206–212 (Aug. 1, 1989).

Kald et al., "Release of Platelet-Activating Factor in Acute Experimental Pancreatitis", *Pancreas*, 8(4):440–442 (1993).

Kurosawa et al., "Increased levels of blood platelet-activating factor in bronchial asthmatic patients with active symptoms", *Allergy*, 49:60–63 (1994).

La Vallie et al., "A Thioredoxin Gene Fusion Expression System That Circumvents Inclusion Body Formation in the *E. coli* Cytoplasm", *Bio/Technology*, 11:187–193 (Feb. 11, 1993).

Lewin, pp. 136–141 in *Genes V*, Oxford University Press, New York, New York (1994).

Lindsberg et al., "Evidence for Platelet-Activating Factor as a Novel Mediator in Experimental Stroke in Rabbits", *Stroke*, 21(10):1452–1457 (Oct. 1990).

Lindsberg et al., "Platelet-activating Factor in Stroke and Brain Injury", *Ann. Neurol.*, 30(2):117–129 (Aug. 1991).

Maki et al., "Platelet-activating factor acetylhydrolase activity in maternal, fetal, and newborn rabbit plasma during pregnancy and lactation", *Proc. Natl. Acad. Sci. USA*, 85:728–732 (Feb. 1988).

Matsumoto et al., "Platelet-Activating Factor in Bronchoalveolar Lavage Fluid of Patients With Adult Respiratory Distress Syndrome", *Clin. Exp. Pharmacol. Physiol.*, 19:509–515 (1992).

Matsuzaki et al., "PAF acetylhydrolase activities in human systemic lupus erythematosus and lupus-prone mice", *Clinica Chimica Acta*, 210:139–144 (1992).

Mezzano et al., "Detection of Platelet-Activating Factor in Plasma of Patients with Streptococcal Nephritis", *J. Am. Soc. Nephrol.*, 4:235–242 (1993).

Miwa et al., "Characterization of Serum Platelet-activating Factor (PAF) Acetylhydrolase", *J. Clin. Invest.*, 82:1983–1991 (Dec. 1988).

Rabinovici et al., "ARDS-like lung injury produced by endotoxin in platelet-activating factor-primed rats", *J. Appl. Physiol.*, 74(4):1791–1802 (1993).

Rabinovici et al., "Platelet Activating Factor Mediates Interleukin-2-induced Lung Injury in the Rat", *J. Clin. Invest.*, 89:1669–1673 (May 1992).

Rodriguez-Roisin et al., "Platelet-activating Factor Causes Ventilation-Perfusion Mismatch in Humans", *J. Clin. Invest.*, 93:188–194 (Jan. 1994).

Satoh et al., "Platelet-activating Factor (PAF) Stimulates the Production of PAF Acetylhydrolase by the Human Hepatoma Cell Line, HepG2", *J. Clin. Invest.*, 87:476–481 (Feb. 1991).

Satoh et al., "Platelet-Activating Factor Acetylhydrolase in Plasma Lipoproteins From Patients With Ischemic Stroke", *Stroke*, 23:1090–1092 (1992).

Smith et al., "Pulmonary Deposition and Clearance of Aerosolized Alpha-1-Proteinase Inhibitor Administered to Dogs and to Sheep", *J. Clin. Invest.*, 84:1145–1154 (Oct. 1989).

Stafforini et al., "Human Macrophages Secrete Platelet-activating Factor Acetylhydrolase", *J. Biol. Chem.*, 265(17):9682–9687 (Jun. 15, 1990).

Stafforini et al., "Human Plasma Platelet-activating Factor Acetylhdrolase: Association with lipoprotein particles and role in the degradation of platelet-activating factor", *J. Biol. Chem.*, 262(9):4215–4222 (Mar. 25, 1987).

Stafforini et al., "Human Plasma Platelet-activating Factor Acetylhydrolase: Purification and Properties", *J. Biol. Chem.*, 262(9):4223–4230 (Mar. 25, 1987).

Stafforini et al., "Platelet-activating factor acetylhydrolase activity in human tissues and blood cells", *LIPIDS*, 26(12):979–985 (1991).

Stafforini et al., "The Platelet-activating Factor Acetylhydrolase from Human Erythrocytes: Purification and Properties", *J. Biol. Chem.*, 268(6):3857–3865 (Feb. 25, 1993).

Stafforini et al., "Lipoproteins alter the catalytic behavior of the platelet-activating factor acetylhydrolase in human plasma", *Proc. Natl. Acad. Sci.*, 86:2393–2397 (Apr. 1989).

Stremler et al., "Human Plasma Platelet-activating Factor Acetylhydrolase", *J. Biol. Chem.*, 266(17):11095–11103 (Jun. 15, 1991).

Tarbet et al., "Liver Cells Secrete the Plasma Form of Platelet-activating Factor Acetylhydrolase", *J. Biol. Chem.*, 266(25):16667–16673 (Sep. 1991).

Venable et al., "Platelet-activating factor: a phospholipid autacoid with diverse actions", *J. Lipid Res.*, 34:691–701 (1993).

von Heijne, "A new method for predicting signal sequence cleavage sites", *Nuc. Acids Res.*, 14(11):4683–4690 (1986).

Wada et al., "Codon Usage tabulated from the GenBank Genetic sequence data", *Nuc. Acids Res.*, 19S:1981–1986 (1991).

Watanabe et al., "Pharmacological analysis of neutrophil chemtactic factor production by leucocytes and roles of PAF in allergic inflammation in rats", *Br. J. Pharmacol.*, 111:123–130 (1994).

Watson et al., "The Platelet-Activating Factor Antagonist Web 2170 Its Beneficial Effect on Dog Renal Allograft Survival", *Transplantation*, 56(4):1047–1049 (Oct. 1993).

Zarco et al., "Involvement of platelet-activating factor and tumor necrosis factor in the pathogenesis of joint inflammation in rabbits", *Clin. exp. Immunol.*, 88:318–323 (1992).

Experiment 1

Experiment 2

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Phe  Lys  Asp  Leu  Gly  Glu  Glu  Asn  Phe  Lys  Ala  Leu  Val  Leu  Ile  Ala
1                  5                            10                           15

Phe
```

( 2 ) INFORMATION FOR SEQ ID NO:2:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Ile  Gln  Val  Leu  Met  Ala  Ala  Ala  Ser  Phe  Gly  Gln  Thr  Lys  Ile  Pro
```

( 2 ) INFORMATION FOR SEQ ID NO:3:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Met Lys Pro Leu Val Val Phe Val Leu Gly Gly
 1           5                   10
```

( 2 ) INFORMATION FOR SEQ ID NO:4:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Modified-site
        ( B ) LOCATION: group(13, 21, 27)
        ( C ) OTHER INFORMATION: /note= "The nucleotide at each of
            these positions is an inosine."

( x i ) SEQUENCE DESCRIPTION: SEQ ID NO:4:

ACATGAATTC GGNATC Y TTG NGT Y TGNCCR AA                        32

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

TATTTCTAGA AGTGTGGTGG AACTCGCTGG                            30

( 2 ) INFORMATION FOR SEQ ID NO:6:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

CGATGAATTC AGCTTGCAGC AGCCATCAGT AC                       32

( 2 ) INFORMATION FOR SEQ ID NO:7:

( i ) SEQUENCE CHARACTERISTICS:
        ( A ) LENGTH: 1520 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:

( A ) NAME/KEY: CDS
( B ) LOCATION: 162..1484

( x i ) SEQUENCE DESCRIPTION: SEQ ID NO:7:

```
GCTGGTCGGA GGCTCGCAGT GCTGTCGGCG AGAAGCAGTC GGGTTTGGAG CGCTTGGGTC    60

GCGTTGGTGC GCGGTGGAAC GCGCCCAGGG ACCCCAGTTC CGCGAGCAG CTCCGCGCCG    120

CGCCTGAGAG ACTAAGCTGA AACTGCTGCT CAGCTCCCAA G ATG GTG CCA CCC       173
                                              Met Val Pro Pro
                                               1
```

| | | | | | | | | | | | | | | | | |
|---|---|---|---|---|---|---|---|---|---|---|---|---|---|---|---|---|
| AAA | TTG | CAT | GTG | CTT | TTC | TGC | CTC | TGC | GGC | TGC | CTG | GCT | GTG | GTT | TAT | 221 |
| Lys | Leu | His | Val | Leu | Phe | Cys | Leu | Cys | Gly | Cys | Leu | Ala | Val | Val | Tyr | |
| 5 | | | | 10 | | | | | 15 | | | | | | 20 | |
| CCT | TTT | GAC | TGG | CAA | TAC | ATA | AAT | CCT | GTT | GCC | CAT | ATG | AAA | TCA | TCA | 269 |
| Pro | Phe | Asp | Trp | Gln | Tyr | Ile | Asn | Pro | Val | Ala | His | Met | Lys | Ser | Ser | |
| | | | | 25 | | | | | 30 | | | | | 35 | | |
| GCA | TGG | GTC | AAC | AAA | ATA | CAA | GTA | CTG | ATG | GCT | GCT | GCA | AGC | TTT | GGC | 317 |
| Ala | Trp | Val | Asn | Lys | Ile | Gln | Val | Leu | Met | Ala | Ala | Ala | Ser | Phe | Gly | |
| | | | 40 | | | | | 45 | | | | | 50 | | | |
| CAA | ACT | AAA | ATC | CCC | CGG | GGA | AAT | GGG | CCT | TAT | TCC | GTT | GGT | TGT | ACA | 365 |
| Gln | Thr | Lys | Ile | Pro | Arg | Gly | Asn | Gly | Pro | Tyr | Ser | Val | Gly | Cys | Thr | |
| | | 55 | | | | | 60 | | | | | 65 | | | | |
| GAC | TTA | ATG | TTT | GAT | CAC | ACT | AAT | AAG | GGC | ACC | TTC | TTG | CGT | TTA | TAT | 413 |
| Asp | Leu | Met | Phe | Asp | His | Thr | Asn | Lys | Gly | Thr | Phe | Leu | Arg | Leu | Tyr | |
| | 70 | | | | | 75 | | | | | 80 | | | | | |
| TAT | CCA | TCC | CAA | GAT | AAT | GAT | CGC | CTT | GAC | ACC | CTT | TGG | ATC | CCA | AAT | 461 |
| Tyr | Pro | Ser | Gln | Asp | Asn | Asp | Arg | Leu | Asp | Thr | Leu | Trp | Ile | Pro | Asn | |
| 85 | | | | | 90 | | | | | 95 | | | | | 100 | |
| AAA | GAA | TAT | TTT | TGG | GGT | CTT | AGC | AAA | TTT | CTT | GGA | ACA | CAC | TGG | CTT | 509 |
| Lys | Glu | Tyr | Phe | Trp | Gly | Leu | Ser | Lys | Phe | Leu | Gly | Thr | His | Trp | Leu | |
| | | | | 105 | | | | | 110 | | | | | 115 | | |
| ATG | GGC | AAC | ATT | TTG | AGG | TTA | CTC | TTT | GGT | TCA | ATG | ACA | ACT | CCT | GCA | 557 |
| Met | Gly | Asn | Ile | Leu | Arg | Leu | Leu | Phe | Gly | Ser | Met | Thr | Thr | Pro | Ala | |
| | | | 120 | | | | | 125 | | | | | 130 | | | |
| AAC | TGG | AAT | TCC | CCT | CTG | AGG | CCT | GGT | GAA | AAA | TAT | CCA | CTT | GTT | GTT | 605 |
| Asn | Trp | Asn | Ser | Pro | Leu | Arg | Pro | Gly | Glu | Lys | Tyr | Pro | Leu | Val | Val | |
| | | 135 | | | | | 140 | | | | | 145 | | | | |
| TTT | TCT | CAT | GGT | CTT | GGG | GCA | TTC | AGG | ACA | CTT | TAT | TCT | GCT | ATT | GGC | 653 |
| Phe | Ser | His | Gly | Leu | Gly | Ala | Phe | Arg | Thr | Leu | Tyr | Ser | Ala | Ile | Gly | |
| | 150 | | | | | 155 | | | | | 160 | | | | | |
| ATT | GAC | CTG | GCA | TCT | CAT | GGG | TTT | ATA | GTT | GCT | GCT | GTA | GAA | CAC | AGA | 701 |
| Ile | Asp | Leu | Ala | Ser | His | Gly | Phe | Ile | Val | Ala | Ala | Val | Glu | His | Arg | |
| 165 | | | | | 170 | | | | | 175 | | | | | 180 | |
| GAT | AGA | TCT | GCA | TCT | GCA | ACT | TAC | TAT | TTC | AAG | GAC | CAA | TCT | GCT | GCA | 749 |
| Asp | Arg | Ser | Ala | Ser | Ala | Thr | Tyr | Tyr | Phe | Lys | Asp | Gln | Ser | Ala | Ala | |
| | | | | 185 | | | | | 190 | | | | | 195 | | |
| GAA | ATA | GGG | GAC | AAG | TCT | TGG | CTC | TAC | CTT | AGA | ACC | CTG | AAA | CAA | GAG | 797 |
| Glu | Ile | Gly | Asp | Lys | Ser | Trp | Leu | Tyr | Leu | Arg | Thr | Leu | Lys | Gln | Glu | |
| | | | 200 | | | | | 205 | | | | | 210 | | | |
| GAG | GAG | ACA | CAT | ATA | CGA | AAT | GAG | CAG | GTA | CGG | CAA | AGA | GCA | AAA | GAA | 845 |
| Glu | Glu | Thr | His | Ile | Arg | Asn | Glu | Gln | Val | Arg | Gln | Arg | Ala | Lys | Glu | |
| | | 215 | | | | | 220 | | | | | 225 | | | | |
| TGT | TCC | CAA | GCT | CTC | AGT | CTG | ATT | CTT | GAC | ATT | GAT | CAT | GGA | AAG | CCA | 893 |
| Cys | Ser | Gln | Ala | Leu | Ser | Leu | Ile | Leu | Asp | Ile | Asp | His | Gly | Lys | Pro | |
| | 230 | | | | | 235 | | | | | 240 | | | | | |
| GTG | AAG | AAT | GCA | TTA | GAT | TTA | AAG | TTT | GAT | ATG | GAA | CAA | CTG | AAG | GAC | 941 |
| Val | Lys | Asn | Ala | Leu | Asp | Leu | Lys | Phe | Asp | Met | Glu | Gln | Leu | Lys | Asp | |
| 245 | | | | 250 | | | | | 255 | | | | | 260 | | |
| TCT | ATT | GAT | AGG | GAA | AAA | ATA | GCA | GTA | ATT | GGA | CAT | TCT | TTT | GGT | GGA | 989 |
| Ser | Ile | Asp | Arg | Glu | Lys | Ile | Ala | Val | Ile | Gly | His | Ser | Phe | Gly | Gly | |

|  |  |  |  |  |  |  |  |  |  |  |  |  |  |  |  |  |
|---|---|---|---|---|---|---|---|---|---|---|---|---|---|---|---|---|
|  | 265 |  |  |  |  | 270 |  |  |  |  | 275 |  |  |  |  |  |
| GCA | ACG | GTT | ATT | CAG | ACT | CTT | AGT | GAA | GAT | CAG | AGA | TTC | AGA | TGT | GGT | 1037 |
| Ala | Thr | Val | Ile | Gln | Thr | Leu | Ser | Glu | Asp | Gln | Arg | Phe | Arg | Cys | Gly |  |
|  |  |  | 280 |  |  |  | 285 |  |  |  |  | 290 |  |  |  |  |
| ATT | GCC | CTG | GAT | GCA | TGG | ATG | TTT | CCA | CTG | GGT | GAT | GAA | GTA | TAT | TCC | 1085 |
| Ile | Ala | Leu | Asp | Ala | Trp | Met | Phe | Pro | Leu | Gly | Asp | Glu | Val | Tyr | Ser |  |
|  |  | 295 |  |  |  |  | 300 |  |  |  |  | 305 |  |  |  |  |
| AGA | ATT | CCT | CAG | CCC | CTC | TTT | TTT | ATC | AAC | TCT | GAA | TAT | TTC | CAA | TAT | 1133 |
| Arg | Ile | Pro | Gln | Pro | Leu | Phe | Phe | Ile | Asn | Ser | Glu | Tyr | Phe | Gln | Tyr |  |
|  | 310 |  |  |  |  | 315 |  |  |  |  | 320 |  |  |  |  |  |
| CCT | GCT | AAT | ATC | ATA | AAA | ATG | AAA | AAA | TGC | TAC | TCA | CCT | GAT | AAA | GAA | 1181 |
| Pro | Ala | Asn | Ile | Ile | Lys | Met | Lys | Lys | Cys | Tyr | Ser | Pro | Asp | Lys | Glu |  |
| 325 |  |  |  |  | 330 |  |  |  |  | 335 |  |  |  |  | 340 |  |
| AGA | AAG | ATG | ATT | ACA | ATC | AGG | GGT | TCA | GTC | CAC | CAG | AAT | TTT | GCT | GAC | 1229 |
| Arg | Lys | Met | Ile | Thr | Ile | Arg | Gly | Ser | Val | His | Gln | Asn | Phe | Ala | Asp |  |
|  |  |  |  | 345 |  |  |  |  | 350 |  |  |  |  | 355 |  |  |
| TTC | ACT | TTT | GCA | ACT | GGC | AAA | ATA | ATT | GGA | CAC | ATG | CTC | AAA | TTA | AAG | 1277 |
| Phe | Thr | Phe | Ala | Thr | Gly | Lys | Ile | Ile | Gly | His | Met | Leu | Lys | Leu | Lys |  |
|  |  |  | 360 |  |  |  |  | 365 |  |  |  |  | 370 |  |  |  |
| GGA | GAC | ATA | GAT | TCA | AAT | GTA | GCT | ATT | GAT | CTT | AGC | AAC | AAA | GCT | TCA | 1325 |
| Gly | Asp | Ile | Asp | Ser | Asn | Val | Ala | Ile | Asp | Leu | Ser | Asn | Lys | Ala | Ser |  |
|  |  | 375 |  |  |  |  | 380 |  |  |  |  | 385 |  |  |  |  |
| TTA | GCA | TTC | TTA | CAA | AAG | CAT | TTA | GGA | CTT | CAT | AAA | GAT | TTT | GAT | CAG | 1373 |
| Leu | Ala | Phe | Leu | Gln | Lys | His | Leu | Gly | Leu | His | Lys | Asp | Phe | Asp | Gln |  |
|  | 390 |  |  |  |  | 395 |  |  |  |  | 400 |  |  |  |  |  |
| TGG | GAC | TGC | TTG | ATT | GAA | GGA | GAT | GAT | GAG | AAT | CTT | ATT | CCA | GGG | ACC | 1421 |
| Trp | Asp | Cys | Leu | Ile | Glu | Gly | Asp | Asp | Glu | Asn | Leu | Ile | Pro | Gly | Thr |  |
| 405 |  |  |  |  | 410 |  |  |  |  | 415 |  |  |  |  | 420 |  |
| AAC | ATT | AAC | ACA | ACC | AAT | CAA | CAC | ATC | ATG | TTA | CAG | AAC | TCT | TCA | GGA | 1469 |
| Asn | Ile | Asn | Thr | Thr | Asn | Gln | His | Ile | Met | Leu | Gln | Asn | Ser | Ser | Gly |  |
|  |  |  | 425 |  |  |  |  | 430 |  |  |  |  | 435 |  |  |  |
| ATA | GAG | AAA | TAC | AAT | TAGGATTAAA | ATAGGTTTTT | TAAAAAAAAA | AAAAAA |  |  |  |  |  |  |  | 1520 |
| Ile | Glu | Lys | Tyr | Asn |  |  |  |  |  |  |  |  |  |  |  |  |
|  |  |  | 440 |  |  |  |  |  |  |  |  |  |  |  |  |  |

( 2 ) INFORMATION FOR SEQ ID NO:8:

( i ) SEQUENCE CHARACTERISTICS:
      ( A ) LENGTH: 441 amino acids
      ( B ) TYPE: amino acid
      ( D ) TOPOLOGY: linear ( i i ) MOLECULE TYPE: protein ( x i ) SEQUENCE DESCRIPTION: SEQ ID NO:8:

| Met | Val | Pro | Pro | Lys | Leu | His | Val | Leu | Phe | Cys | Leu | Cys | Gly | Cys | Leu |
|---|---|---|---|---|---|---|---|---|---|---|---|---|---|---|---|
| 1 |  |  |  | 5 |  |  |  |  | 10 |  |  |  |  | 15 |  |
| Ala | Val | Val | Tyr | Pro | Phe | Asp | Trp | Gln | Tyr | Ile | Asn | Pro | Val | Ala | His |
|  |  |  | 20 |  |  |  |  | 25 |  |  |  |  | 30 |  |  |
| Met | Lys | Ser | Ser | Ala | Trp | Val | Asn | Lys | Ile | Gln | Val | Leu | Met | Ala | Ala |
|  |  | 35 |  |  |  |  | 40 |  |  |  |  | 45 |  |  |  |
| Ala | Ser | Phe | Gly | Gln | Thr | Lys | Ile | Pro | Arg | Gly | Asn | Gly | Pro | Tyr | Ser |
|  | 50 |  |  |  |  | 55 |  |  |  |  | 60 |  |  |  |  |
| Val | Gly | Cys | Thr | Asp | Leu | Met | Phe | Asp | His | Thr | Asn | Lys | Gly | Thr | Phe |
| 65 |  |  |  |  | 70 |  |  |  |  | 75 |  |  |  |  | 80 |
| Leu | Arg | Leu | Tyr | Tyr | Pro | Ser | Gln | Asp | Asn | Asp | Arg | Leu | Asp | Thr | Leu |
|  |  |  |  | 85 |  |  |  |  | 90 |  |  |  |  | 95 |  |
| Trp | Ile | Pro | Asn | Lys | Glu | Tyr | Phe | Trp | Gly | Leu | Ser | Lys | Phe | Leu | Gly |
|  |  |  | 100 |  |  |  |  | 105 |  |  |  |  | 110 |  |  |
| Thr | His | Trp | Leu | Met | Gly | Asn | Ile | Leu | Arg | Leu | Leu | Phe | Gly | Ser | Met |

|     |     |     | 115 |     |     |     | 120 |     |     |     | 125 |     |     |     |
| --- | --- | --- | --- | --- | --- | --- | --- | --- | --- | --- | --- | --- | --- | --- |
| Thr | Thr | Pro | Ala | Asn | Trp | Asn | Ser | Pro | Leu | Arg | Pro | Gly | Glu | Lys | Tyr |
|     | 130 |     |     |     |     | 135 |     |     |     |     | 140 |     |     |     |     |
| Pro | Leu | Val | Val | Phe | Ser | His | Gly | Leu | Gly | Ala | Phe | Arg | Thr | Leu | Tyr |
| 145 |     |     |     |     | 150 |     |     |     |     | 155 |     |     |     |     | 160 |
| Ser | Ala | Ile | Gly | Ile | Asp | Leu | Ala | Ser | His | Gly | Phe | Ile | Val | Ala | Ala |
|     |     |     |     | 165 |     |     |     |     | 170 |     |     |     |     | 175 |     |
| Val | Glu | His | Arg | Asp | Arg | Ser | Ala | Ser | Ala | Thr | Tyr | Tyr | Phe | Lys | Asp |
|     |     |     | 180 |     |     |     |     | 185 |     |     |     |     | 190 |     |     |
| Gln | Ser | Ala | Ala | Glu | Ile | Gly | Asp | Lys | Ser | Trp | Leu | Tyr | Leu | Arg | Thr |
|     |     | 195 |     |     |     |     | 200 |     |     |     |     | 205 |     |     |     |
| Leu | Lys | Gln | Glu | Glu | Glu | Thr | His | Ile | Arg | Asn | Glu | Gln | Val | Arg | Gln |
|     | 210 |     |     |     |     | 215 |     |     |     |     | 220 |     |     |     |     |
| Arg | Ala | Lys | Glu | Cys | Ser | Gln | Ala | Leu | Ser | Leu | Ile | Leu | Asp | Ile | Asp |
| 225 |     |     |     |     | 230 |     |     |     |     | 235 |     |     |     |     | 240 |
| His | Gly | Lys | Pro | Val | Lys | Asn | Ala | Leu | Asp | Leu | Lys | Phe | Asp | Met | Glu |
|     |     |     |     | 245 |     |     |     |     | 250 |     |     |     |     | 255 |     |
| Gln | Leu | Lys | Asp | Ser | Ile | Asp | Arg | Glu | Lys | Ile | Ala | Val | Ile | Gly | His |
|     |     |     | 260 |     |     |     |     | 265 |     |     |     |     | 270 |     |     |
| Ser | Phe | Gly | Gly | Ala | Thr | Val | Ile | Gln | Thr | Leu | Ser | Glu | Asp | Gln | Arg |
|     |     | 275 |     |     |     |     | 280 |     |     |     |     | 285 |     |     |     |
| Phe | Arg | Cys | Gly | Ile | Ala | Leu | Asp | Ala | Trp | Met | Phe | Pro | Leu | Gly | Asp |
|     | 290 |     |     |     |     | 295 |     |     |     |     | 300 |     |     |     |     |
| Glu | Val | Tyr | Ser | Arg | Ile | Pro | Gln | Pro | Leu | Phe | Phe | Ile | Asn | Ser | Glu |
| 305 |     |     |     |     | 310 |     |     |     |     | 315 |     |     |     |     | 320 |
| Tyr | Phe | Gln | Tyr | Pro | Ala | Asn | Ile | Ile | Lys | Met | Lys | Lys | Cys | Tyr | Ser |
|     |     |     |     | 325 |     |     |     |     | 330 |     |     |     |     | 335 |     |
| Pro | Asp | Lys | Glu | Arg | Lys | Met | Ile | Thr | Ile | Arg | Gly | Ser | Val | His | Gln |
|     |     |     | 340 |     |     |     |     | 345 |     |     |     |     | 350 |     |     |
| Asn | Phe | Ala | Asp | Phe | Thr | Phe | Ala | Thr | Gly | Lys | Ile | Ile | Gly | His | Met |
|     |     | 355 |     |     |     |     | 360 |     |     |     |     | 365 |     |     |     |
| Leu | Lys | Leu | Lys | Gly | Asp | Ile | Asp | Ser | Asn | Val | Ala | Ile | Asp | Leu | Ser |
|     | 370 |     |     |     |     | 375 |     |     |     |     | 380 |     |     |     |     |
| Asn | Lys | Ala | Ser | Leu | Ala | Phe | Leu | Gln | Lys | His | Leu | Gly | Leu | His | Lys |
| 385 |     |     |     |     | 390 |     |     |     |     | 395 |     |     |     |     | 400 |
| Asp | Phe | Asp | Gln | Trp | Asp | Cys | Leu | Ile | Glu | Gly | Asp | Asp | Glu | Asn | Leu |
|     |     |     |     | 405 |     |     |     |     | 410 |     |     |     |     | 415 |     |
| Ile | Pro | Gly | Thr | Asn | Ile | Asn | Thr | Thr | Asn | Gln | His | Ile | Met | Leu | Gln |
|     |     |     | 420 |     |     |     |     | 425 |     |     |     |     | 430 |     |     |
| Asn | Ser | Ser | Gly | Ile | Glu | Lys | Tyr | Asn |     |     |     |     |     |     |     |
|     |     | 435 |     |     |     |     | 440 |     |     |     |     |     |     |     |     |

( 2 ) INFORMATION FOR SEQ ID NO:9:

( i ) SEQUENCE CHARACTERISTICS:
        ( A ) LENGTH: 504 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: exon
        ( B ) LOCATION: 185..311

( x i ) SEQUENCE DESCRIPTION: SEQ ID NO:9:

GCGCGCTCTA GTAGAGCCGG GCCACACACG CTCCTCCCCG TACCTCCTCC AGCATCACCG    60

```
AGGGGAAGGA   GAGGGTCGGG   CCACAAGGCG   CGCTAGGCGG   ACCCAGGACA   CAGCCCGCGC      120

GCAGCCCACC   CGCCCGGCCG   CCTGCCAGGA   GCTGCTGCGG   CCGCGCAGCC   AGGGGGACAG      180

GCGGGCTGGT   CGGAGGCTCG   CAGTGCTGTC   GGCGAGAAGC   AGTCGGGTTT   GGAGCGCTTG      240

GGTCGCGTTG   GTGCGCGGTG   GAACGCGCCC   AGGGACCCCA   GTTCCCGCGA   GCAGCTCCGC      300

GCCGCGCCTG   AGTGAGGAGG   GGCCCCGGGG   GCGAGGCGGG   AGTGGGAGGA   AGGGCACGGT      360

CGCCGCGCTG   GAGGTCGGGA   CCCCGGAGCG   CGACCGGCCG   GGGTGGGCTC   GCTGAGTCGC      420

ACCCGCTCTG   CTGGCCGGAC   CTGGGCTCAC   AGTCCTGCAG   CCCTCGGAAA   CAGCGCTAGG      480

ATCCTTCGGG   AGAGGAGAGA   TGAC                                                  504
```

( 2 ) INFORMATION FOR SEQ ID NO:10:

( i ) SEQUENCE CHARACTERISTICS:
        ( A ) LENGTH: 417 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: exon
        ( B ) LOCATION: 145..287

( x i ) SEQUENCE DESCRIPTION: SEQ ID NO:10:

```
GTACCAATCT   AAAACCCAGC   ACAGAAAAAT   ACATGTTTTA   TTTTTTCCAA   GTGTTACTAG       60

TACCTCAGCC   TTTCTTGATT   TGTCAGCTTA   TTTAAGGCCT   CTTCATTGCA   TACTTCTTTT      120

TTCTTTTAAT   CATCTGCTTC   GAAGGAGACT   AAGCTGAAAC   TGCTGCTCAG   CTCCCAAGAT      180

GGTGCCACCC   AAATTGCATG   TGCTTTTCTG   CCTCTGCGGC   TGCCTGGCTG   TGGTTTATCC      240

TTTTGACTGG   CAATACATAA   ATCCTGTTGC   CCATATGAAA   TCATCAGGTA   AGAGGTGTAT      300

TTGTTCAAGG   TCTTGAGCAA   CTGATCTGTC   GCCATACTTC   AAGTGGGCCC   CAAGAAGTTG      360

CACATCTGCA   CATCTAAACA   AGTCCTATTT   AAAGGCTTAT   GGAGATCCTG   TATTCTC         417
```

( 2 ) INFORMATION FOR SEQ ID NO:11:

( i ) SEQUENCE CHARACTERISTICS:
        ( A ) LENGTH: 498 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: exon
        ( B ) LOCATION: 251..372

( x i ) SEQUENCE DESCRIPTION: SEQ ID NO:11:

```
CATTAGGAGG   TAACAGTCCA   AGGCAGCTGA   GAGAAAGGCT   ATGTCTACTT   TCATCTCTTT       60

ACCCTCCAAA   ACCCCTACAC   AGTGTTTCAA   ACAGAGAGAC   CCTCAATAAT   TGCATATCTT      120

ACTTGTTAGG   TTGAGAAAGA   AAGAAGGCCA   GAAACTATGG   GAAGTAACTT   GATTCCGTTG      180

GAATTCTTTT   GCATAATAAA   ATCTGATATG   TAATGGATGA   CAAATGAGAT   AATATTTACC      240

TGTTTTTCAG   CATGGGTCAA   CAAAATACAA   GTACTGATGG   CTGCTGCAAC   GTTTGGCCAA      300

ACTAAAATCC   CCCGGGGAAA   TGGGCCTTAT   TCCGTTGGTT   GTACAGACTT   AATGTTTGAT      360

CACACTAATA   AGGTAATGCT   TTGATTTATA   CAACTTATCC   TGATACTCTA   ATATTGTCTG      420

TCGCTATGGA   CCACTAGAAG   GTGTTCAAAT   GTGACCTTGC   CCTCACCTGA   GAATGACTCA      480
```

TTTTCGAATT TGTATTGT 498

(2) INFORMATION FOR SEQ ID NO:12:

(i) SEQUENCE CHARACTERISTICS:
        (A) LENGTH: 433 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 130..274

(xi) SEQUENCE DESCRIPTION: SEQ ID NO:12:

```
CAGCAGCCTA AAGTCTTAGA CTTTGTGAAC ACAGAGGTAT TGAGTCCCAC TAATTAATAT      60
CGAAAATAGC TGCTGGAATA TGTTTGAGAC ACAACTTCTC TAAAAGTGCA TTAATTTCTT     120
TCTTAACAGG GCACCTTCTT GCGTTTATAT TATCCATCCC AAGATAATGA TCACCTTGAC     180
ACCCTTTGGA TCCCAAATAA AGAATATTTT TGGGGTCTTA GCAAATTTCT TGGAACACAC     240
TGGCTTATGG GCAACATTTT GAGGTTACTC TTTGGTAAGA TTTCTGTTGA TCCTTCTTTG     300
TAGGCTCTTG CATGTATGAA AACCTTGAAA ACAACAAGAA CTTCAAGTAG TTAAGACCAA     360
AGTAGATTTT TCTTCAGTCC AAATAGCTCC TAAAATGATA AGGAAAGTAT TTCTTTAAAG     420
CCCAGGCAAC TAC                                                        433
```

(2) INFORMATION FOR SEQ ID NO:13:

(i) SEQUENCE CHARACTERISTICS:
        (A) LENGTH: 486 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 164..257

(xi) SEQUENCE DESCRIPTION: SEQ ID NO:13:

```
TTGGTGGGTA TCTAGTAGCA GTCTTTTTAA TGAATCTACT ATTCATCCAT AAAAAAGTAG      60
ATATAAATCA GATGGGTCTG CATTTTATGC TAATGAGATA TGAATTAAAT TCACTAGCAA     120
CACTCAGAGA AAACCTTAAC TATAACCTTC CATTGTTGTC TAGGTTCAAT GACAACTCCT     180
GCAAACTGGA ATTCCCTCT GAGGCCTGGT GAAAATATC CACTTGTTGT TTTTTCTCAT      240
GGTCTTGGGG CATTCAGGTA ATGTTTGAGA GGTTGAACAA TTTTGGCTTC CAGGAATAAA     300
TGACAATTTT TTTATTCAAG AAAGAAATAG CAGAGTTTGG AATGTCATGC AGGCCCTTGT     360
CTGGAGGAGT TGGGGTTCCT CAATAATTGG CTGTGGGTCT ATTGATCAGT CCTAGACCTG     420
TCTGGTCAAG TAGTTTTTC CCTACTATCA GCTCATTGGG ATTAGCCTCA CAGCAGAGAA     480
GAAAGG                                                                486
```

(2) INFORMATION FOR SEQ ID NO:14:

(i) SEQUENCE CHARACTERISTICS:
        (A) LENGTH: 363 base pairs
        (B) TYPE: nucleic acid
        (C) STRANDEDNESS: single
        (D) TOPOLOGY: linear ( i i ) MOLECULE TYPE: DNA (genomic)

( i x ) FEATURE:
    ( A ) NAME/KEY: exon
    ( B ) LOCATION: 113..181

( x i ) SEQUENCE DESCRIPTION: SEQ ID NO:14:

| | | | | | | |
|---|---|---|---|---|---|---|
| CCCCAGGCTC | TACTACAGGG | TGTAATGGCC | TCCATGTTCC | CAGTTTTATT | AGTGACTCAG | 60 |
| CCTTGTAATT | CATGACTGGT | AGTTGTAATT | CTTCCCTCTT | TTTGTTTTGA | AGGACACTTT | 120 |
| ATTCTGCTAT | TGGCATTGAC | CTGGCATCTC | ATGGGTTTAT | AGTTGCTGCT | GTAGAACACA | 180 |
| GGTATGTTAC | CTGATATAAT | TGGGCTCTTT | GGCCAACTAC | AGGGAATGTC | AATGCTCATA | 240 |
| ACTATGTTTC | TAATTTTCAT | AAAAGTTTAT | TTAAAATGTT | GATGGAACTT | TCAAGTATGG | 300 |
| TAACATCATG | AGCAAAAAAG | GAGATTGAGT | TTTATCGACT | TAAAAGACTT | AAAAGCACCT | 360 |
| AAC | | | | | | 363 |

( 2 ) INFORMATION FOR SEQ ID NO:15:

( i ) SEQUENCE CHARACTERISTICS:
        ( A ) LENGTH: 441 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: exon
        ( B ) LOCATION: 68..191

( x i ) SEQUENCE DESCRIPTION: SEQ ID NO:15:

| | | | | | | |
|---|---|---|---|---|---|---|
| GAACTGAGAA | ACATGGTCAG | ATGAGGAAGG | GAAGGAGCAT | GCATAAATAA | TTTTGCTTGT | 60 |
| ATTATAGAGA | TAGATCTGCA | TCTGCAACTT | ACTATTTCAA | GGACCAATCT | GCTGCAGAAA | 120 |
| TAGGGGACAA | GTCTTGGCTC | TACCTTAGAA | CCCTGAAACA | AGAGGAGGAG | ACACATATAC | 180 |
| GAAATGAGCA | GGTACATTGC | AGTGAAGGA | GAGGTGGTTG | GTGACCTAAA | AGCATGTACA | 240 |
| AAAGGATGAC | ATTTGTTAAT | TTAATTTTAC | ACCTGGCAAG | TTATGCTCCT | AGCTCTCCTA | 300 |
| TTTCCCATTC | CCAAAAGATC | TGTCAATAGA | TTCCTGGAGC | AGTAAAATTC | CCTTAATGGA | 360 |
| ATATCTAGTT | CATAGTAAAA | ACAAGGCAA | ATACAAAAAT | TGGGAGATG | ACAGTGAATA | 420 |
| TTCAGAATTC | CTCGAGCCGG | G | | | | 441 |

( 2 ) INFORMATION FOR SEQ ID NO:16:

( i ) SEQUENCE CHARACTERISTICS:
        ( A ) LENGTH: 577 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: exon
        ( B ) LOCATION: 245..358

( x i ) SEQUENCE DESCRIPTION: SEQ ID NO:16:

| | | | | | | |
|---|---|---|---|---|---|---|
| GGTTAAGTAA | ATCGTCTGAA | GTCACATAGT | AGGTAAGGCA | AAACAGAGCC | AGGATTTGGA | 60 |
| CTAAGGCTAT | ACCTATGTGC | AAAGCTGGGG | CCTGTGTCAT | TATGGTAGCA | AGTAATAGTC | 120 |
| ACTAATCAGA | TTTCCAGTTT | ATAACTGACC | AACGATTTTT | CCCAAATACA | GCTTCTACCT | 180 |
| AAACTTTAAA | ATAAGTGTTA | TAACTTTTTA | CTTGTCATT | TCCTTCTTCT | AATAATTATA | 240 |

| TTAGGTACGG | CAAAGAGCAA | AAGAATGTTC | CCAAGCTCTC | AGTCTGATTC | TTGACATTGA | 300 |
| TCATGGAAAG | CCAGTGAAGA | ATGCATTAGA | TTTAAAGTTT | GATATGGAAC | AACTGAAGGT | 360 |
| AAGCTATAAA | AAGTAATTTT | TCTCTTGTCC | TACAGTTCTT | TATTGTTTTT | TGTCATTTAA | 420 |
| TTTTCTGCCT | ATATTGCAAG | GTACAATATG | ATAAAGGGCT | GCAACCAGCC | CCTCCCCAAT | 480 |
| GCGCACACAC | AGACACACAA | AGCAGTACAG | GTAAAGTATT | GCAGCAATGA | AGAATGCATT | 540 |
| ATCTTGGACT | AGATATGAAT | GCAAAGTTAG | TCAGTTT | | | 577 |

( 2 ) INFORMATION FOR SEQ ID NO:17:

( i ) SEQUENCE CHARACTERISTICS:
        ( A ) LENGTH: 396 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: exon
        ( B ) LOCATION: 108..199

( x i ) SEQUENCE DESCRIPTION: SEQ ID NO:17:

| ATCAATGTAT | TTACCATCCC | CATGAAATGA | ACAATTATAT | GATTGACAAA | TCATTTCTTC | 60 |
| TAACACCACG | AAATAGCTAT | AAATTTATAT | CATGCTTTTT | CAAATAGGAC | TCTATTGATA | 120 |
| GGGAAAAAAT | AGCAGTAATT | GGACATTCTT | TTGGTGGAGC | AACGGTTATT | CAGACTCTTA | 180 |
| GTGAAGATCA | GAGATTCAGG | TAAGAAAATA | AGATAGTAAA | GCAAGAGAAT | AGTAAATTAT | 240 |
| TGGAAGAAAT | TATATTGTGA | GATATAATTT | TTATTCAAAT | TCTTAGTGAA | GGAAGGGGAT | 300 |
| CTCTTGGAGT | TTATAAGGCT | ATTCTTTTGC | CCCCATAAAA | TACTCTATAT | ACATTTCCT | 360 |
| AGGCTAAAAC | ATCTCCTCTC | CTGCTATTAA | AATCTC | | | 396 |

( 2 ) INFORMATION FOR SEQ ID NO:18:

( i ) SEQUENCE CHARACTERISTICS:
        ( A ) LENGTH: 519 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: exon
        ( B ) LOCATION: 181..351

( x i ) SEQUENCE DESCRIPTION: SEQ ID NO:18:

| CTTACAAAGT | TAATCATATC | CCTTTCCCAC | ATTGAAGTAT | GATACCTCTT | TATTCCAATC | 60 |
| AGATAACCCA | TAATAAACTG | GTATGGTGCG | TGTCCACCAA | TCCTAGCATT | ATTAGGATGT | 120 |
| CCTCAATGTT | GGCTAGTATG | TAACCAGTTT | AATTTCATCA | TTGTCAACAA | ATATCTACAG | 180 |
| ATGTGGTATT | GCCCTGGATG | CATGGATGTT | TCCACTGGGT | GATGAAGTAT | ATTCCAGAAT | 240 |
| TCCTCAGCCC | CTCTTTTTA | TCAACTCTGA | ATATTTCCAA | TATCCTGCTA | ATATCATAAA | 300 |
| AATGAAAAAA | TGCTACTCAC | CTGATAAAGA | AAGAAAGATG | ATTACAATCA | GGTAAGTATT | 360 |
| AGTGACTTAT | TTCATTATGT | GAAACAAACT | TGAAGCTTGG | GTAAATATCA | ATCGATATCA | 420 |
| TTTGGTAACT | ATTAAAGAAT | TGCTGAATTG | GTTGTTTAGA | CTTTCAATAA | GGAGAGAATT | 480 |
| AGATAATCTC | AGTTTCTAAG | TACATTTAGT | CTACTCTTT | | | 519 |

( 2 ) INFORMATION FOR SEQ ID NO:19:

( i ) SEQUENCE CHARACTERISTICS:
    ( A ) LENGTH: 569 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: exon
    ( B ) LOCATION: 156..304

( x i ) SEQUENCE DESCRIPTION: SEQ ID NO:19:

| | | | | | | |
|---|---|---|---|---|---|---|
| TGAAACACAT | CTAAGTAGAT | CAAATTACAA | GTTTTATTTC | TTCTTTGGTT | TTCAGTAAAC | 60 |
| AGACCAACAA | GACCAGTACC | TTTCCTTACA | CTCTAACTAA | AAAAATAATA | ATTTTATCAA | 120 |
| ACAATGTGAC | TTTTAAATGT | CTTGTTCTCT | TTTAGGGGTT | CAGTCCACCA | GAATTTTGCT | 180 |
| GACTTCACTT | TTGCAACTGG | CAAAATAATT | GGACACATGC | TCAAATTAAA | GGGAGACATA | 240 |
| GATTCAAATG | TAGCTATTGA | TCTTAGCAAC | AAAGCTTCAT | TAGCATTCTT | ACAAAAGCAT | 300 |
| TTAGGTAAGA | AACTATTTTT | TTCATGACCT | AAACCGAGAT | GAATCTCGAG | GACAAAGCTG | 360 |
| TCTATCTTAA | TACAGCTTTA | GTACTATTTA | AACTATTTCC | AGTTGGTTTA | CAATGGAACA | 420 |
| AAGCAGTATA | TCAATTTGAA | AACAGAAATT | TGAGAAAGTC | AATTTGCTG | CTTTACATCT | 480 |
| CTATATCATA | GAAAGCAAAT | CAACTGTTAA | AGGTAATATT | CTTTGTATGA | GCTAGAGTGA | 540 |
| CTCATGTGAG | GATATCGAAC | GACGGTGCT | | | | 569 |

( 2 ) INFORMATION FOR SEQ ID NO:20:

( i ) SEQUENCE CHARACTERISTICS:
    ( A ) LENGTH: 469 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: exon
    ( B ) LOCATION: 137..253

( x i ) SEQUENCE DESCRIPTION: SEQ ID NO:20:

| | | | | | | |
|---|---|---|---|---|---|---|
| GATACAGAGG | CACATCGTCT | CTACCATCCT | AACGGAACTT | GTGTAATTTG | TAAATCTTTA | 60 |
| TTGCCACCTA | GGGGCATCCA | AACTGTTTAA | TGCTCTCAAA | AGTTAATAT | GTTGATTAAC | 120 |
| ACTTTATATT | TTATAGGACT | TCATAAAGAT | TTTGATCAGT | GGGACTGCTT | GATTGAAGGA | 180 |
| GATGATGAGA | ATCTTATTCC | AGGGACCAAC | ATTAACACAA | CCAATCAACA | CATCATGTTA | 240 |
| CAGAACTCTT | CAGGAATAGA | GAAATACAAT | TAGGATTAAA | ATAGGTTTTT | TAAAAGTCTT | 300 |
| GTTTCAAAAC | TGTCTAAAAT | TATGTGTGTG | TGTGTGTGTG | TGTGTGTGTG | AGAGAGAGAG | 360 |
| AGAGAGAGAG | AGAGAGAATT | TTAATGTATT | TTCCCAAAGG | ACTCATATTT | TAAAATGTAG | 420 |
| GCTATACTGT | AATCGTGATT | GAAGCTTGGA | CTAAGAATTT | TTTCCCTTT | | 469 |

( 2 ) INFORMATION FOR SEQ ID NO:21:

( i ) SEQUENCE CHARACTERISTICS:
    ( A ) LENGTH: 1494 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:

( A ) NAME/KEY: CDS
( B ) LOCATION: 117..1436

( x i ) SEQUENCE DESCRIPTION: SEQ ID NO:21:

| | |
|---|---|
| GGCACGAGCT AGGATCTGAC TCGCTCTGGT GGCATTGCTG CGCTCAGGGT TCTGGGTATC | 60 |
| CGGGAGTCAG TGCAGTGACC AGAACATCAA ACTGAAGCCA CTGCTCAGCT CCTAAG | 116 |

| | | | | | | | | | | | | | | | | |
|---|---|---|---|---|---|---|---|---|---|---|---|---|---|---|---|---|
| ATG | GTA | CCA | CTC | AAA | CTG | CAG | GCG | CTT | TTC | TGC | CTC | CTC | TGC | TGC | CTC | 164 |
| Met | Val | Pro | Leu | Lys | Leu | Gln | Ala | Leu | Phe | Cys | Leu | Leu | Cys | Cys | Leu | |
| 1 | | | | 5 | | | | | 10 | | | | | 15 | | |
| CCA | TGG | GTC | CAT | CCT | TTT | CAC | TGG | CAA | GAC | ACA | TCT | TCT | TTT | GAC | TTC | 212 |
| Pro | Trp | Val | His | Pro | Phe | His | Trp | Gln | Asp | Thr | Ser | Ser | Phe | Asp | Phe | |
| | | | 20 | | | | | 25 | | | | | 30 | | | |
| AGG | CCG | TCA | GTA | ATG | TTT | CAC | AAG | CTC | CAA | TCG | GTG | ATG | TCT | GCT | GCC | 260 |
| Arg | Pro | Ser | Val | Met | Phe | His | Lys | Leu | Gln | Ser | Val | Met | Ser | Ala | Ala | |
| | | 35 | | | | | 40 | | | | | 45 | | | | |
| GGC | TCT | GGC | CAT | AGT | AAA | ATC | CCC | AAA | GGA | AAT | GGA | TCG | TAC | CCC | GTC | 308 |
| Gly | Ser | Gly | His | Ser | Lys | Ile | Pro | Lys | Gly | Asn | Gly | Ser | Tyr | Pro | Val | |
| | 50 | | | | | 55 | | | | | 60 | | | | | |
| GGT | TGT | ACA | GAT | CTG | ATG | TTC | GGT | TAT | GGG | AAT | GAG | AGC | GTC | TTC | GTG | 356 |
| Gly | Cys | Thr | Asp | Leu | Met | Phe | Gly | Tyr | Gly | Asn | Glu | Ser | Val | Phe | Val | |
| 65 | | | | | 70 | | | | | 75 | | | | | 80 | |
| CGT | TTG | TAC | TAC | CCA | GCT | CAA | GAT | CAA | GGT | CGC | CTC | GAC | ACT | GTT | TGG | 404 |
| Arg | Leu | Tyr | Tyr | Pro | Ala | Gln | Asp | Gln | Gly | Arg | Leu | Asp | Thr | Val | Trp | |
| | | | | 85 | | | | | 90 | | | | | 95 | | |
| ATC | CCA | AAC | AAA | GAA | TAT | TTT | TTG | GGT | CTT | AGT | ATA | TTT | CTT | GGA | ACA | 452 |
| Ile | Pro | Asn | Lys | Glu | Tyr | Phe | Leu | Gly | Leu | Ser | Ile | Phe | Leu | Gly | Thr | |
| | | | 100 | | | | | 105 | | | | | 110 | | | |
| CCC | AGT | ATT | GTA | GGC | AAT | ATT | TTA | CAC | CTC | TTA | TAT | GGT | TCT | CTG | ACA | 500 |
| Pro | Ser | Ile | Val | Gly | Asn | Ile | Leu | His | Leu | Leu | Tyr | Gly | Ser | Leu | Thr | |
| | | 115 | | | | | 120 | | | | | 125 | | | | |
| ACT | CCT | GCA | AGC | TGG | AAT | TCT | CCT | TTA | AGG | ACT | GGA | GAA | AAA | TAC | CCG | 548 |
| Thr | Pro | Ala | Ser | Trp | Asn | Ser | Pro | Leu | Arg | Thr | Gly | Glu | Lys | Tyr | Pro | |
| | 130 | | | | | 135 | | | | | 140 | | | | | |
| CTC | ATT | GTC | TTT | TCT | CAT | GGT | CTC | GGA | GCC | TTC | AGG | ACG | ATT | TAT | TCT | 596 |
| Leu | Ile | Val | Phe | Ser | His | Gly | Leu | Gly | Ala | Phe | Arg | Thr | Ile | Tyr | Ser | |
| 145 | | | | | 150 | | | | | 155 | | | | | 160 | |
| GCT | ATT | GGC | ATT | GGC | TTG | GCA | TCT | AAT | GGG | TTT | ATA | GTG | GCC | ACT | GTC | 644 |
| Ala | Ile | Gly | Ile | Gly | Leu | Ala | Ser | Asn | Gly | Phe | Ile | Val | Ala | Thr | Val | |
| | | | | 165 | | | | | 170 | | | | | 175 | | |
| GAA | CAC | AGA | GAC | AGA | TCT | GCA | TCG | GCA | ACT | TAC | TTT | TTT | GAA | GAC | CAG | 692 |
| Glu | His | Arg | Asp | Arg | Ser | Ala | Ser | Ala | Thr | Tyr | Phe | Phe | Glu | Asp | Gln | |
| | | | 180 | | | | | 185 | | | | | 190 | | | |
| GTG | GCT | GCA | AAA | GTG | GAA | AAC | AGG | TCT | TGG | CTT | TAC | CTG | AGA | AAA | GTA | 740 |
| Val | Ala | Ala | Lys | Val | Glu | Asn | Arg | Ser | Trp | Leu | Tyr | Leu | Arg | Lys | Val | |
| | | 195 | | | | | 200 | | | | | 205 | | | | |
| AAA | CAA | GAG | GAG | TCG | GAA | AGT | GTC | CGG | AAA | GAA | CAG | GTT | CAG | CAA | AGA | 788 |
| Lys | Gln | Glu | Glu | Ser | Glu | Ser | Val | Arg | Lys | Glu | Gln | Val | Gln | Gln | Arg | |
| | 210 | | | | | 215 | | | | | 220 | | | | | |
| GCA | ATA | GAA | TGT | TCC | CGG | GCT | CTC | AGT | GCG | ATT | CTT | GAC | ATT | GAA | CAT | 836 |
| Ala | Ile | Glu | Cys | Ser | Arg | Ala | Leu | Ser | Ala | Ile | Leu | Asp | Ile | Glu | His | |
| 225 | | | | | 230 | | | | | 235 | | | | | 240 | |
| GGA | GAC | CCA | AAA | GAG | AAT | GTA | CTA | GGT | TCA | GCT | TTT | GAC | ATG | AAA | CAG | 884 |
| Gly | Asp | Pro | Lys | Glu | Asn | Val | Leu | Gly | Ser | Ala | Phe | Asp | Met | Lys | Gln | |
| | | | | 245 | | | | | 250 | | | | | 255 | | |
| CTG | AAG | GAT | GCT | ATT | GAT | GAG | ACT | AAA | ATA | GCT | TTG | ATG | GGA | CAT | TCT | 932 |
| Leu | Lys | Asp | Ala | Ile | Asp | Glu | Thr | Lys | Ile | Ala | Leu | Met | Gly | His | Ser | |
| | | | 260 | | | | | 265 | | | | | 270 | | | |
| TTT | GGA | GGA | GCA | ACA | GTT | CTT | CAA | GCC | CTT | AGT | GAG | GAC | CAG | AGA | TTC | 980 |
| Phe | Gly | Gly | Ala | Thr | Val | Leu | Gln | Ala | Leu | Ser | Glu | Asp | Gln | Arg | Phe | |
| | | 275 | | | | | 280 | | | | | 285 | | | | |

-continued

| | | | | | | | | | | | | | | | |
|---|---|---|---|---|---|---|---|---|---|---|---|---|---|---|---|
| AGA | TGT | GGA | GTT | GCT | CTT | GAT | CCA | TGG | ATG | TAT | CCG | GTG | AAC | GAA | GAG | 1028 |
| Arg | Cys | Gly | Val | Ala | Leu | Asp | Pro | Trp | Met | Tyr | Pro | Val | Asn | Glu | Glu | |
| 290 | | | | | 295 | | | | | 300 | | | | | | |
| CTG | TAC | TCC | AGA | ACC | CTC | CAG | CCT | CTC | CTC | TTT | ATC | AAC | TCT | GCC | AAA | 1076 |
| Leu | Tyr | Ser | Arg | Thr | Leu | Gln | Pro | Leu | Leu | Phe | Ile | Asn | Ser | Ala | Lys | |
| 305 | | | | 310 | | | | | 315 | | | | | 320 | | |
| TTC | CAG | ACT | CCA | AAG | GAC | ATC | GCA | AAA | ATG | AAA | AAG | TTC | TAC | CAG | CCT | 1124 |
| Phe | Gln | Thr | Pro | Lys | Asp | Ile | Ala | Lys | Met | Lys | Lys | Phe | Tyr | Gln | Pro | |
| | | | 325 | | | | | 330 | | | | | 335 | | | |
| GAC | AAG | GAA | AGG | AAA | AAT | GAT | TAC | AAT | CAA | GGG | CTC | AGG | CAC | CAG | AAC | 1172 |
| Asp | Lys | Glu | Arg | Lys | Asn | Asp | Tyr | Asn | Gln | Gly | Leu | Arg | His | Gln | Asn | |
| | | 340 | | | | | 345 | | | | | 350 | | | | |
| TTT | GAC | GAC | TTT | ACT | TTT | GTA | ACT | GGC | AAA | ATA | ATT | GGA | AAC | AAG | CTG | 1220 |
| Phe | Asp | Asp | Phe | Thr | Phe | Val | Thr | Gly | Lys | Ile | Ile | Gly | Asn | Lys | Leu | |
| | 355 | | | | | 360 | | | | | 365 | | | | | |
| ACA | CTG | AAA | GGA | GAA | ATC | GAT | TCC | AGA | GTA | GCC | ATC | GAC | CTC | ACC | AAC | 1268 |
| Thr | Leu | Lys | Gly | Glu | Ile | Asp | Ser | Arg | Val | Ala | Ile | Asp | Leu | Thr | Asn | |
| 370 | | | | | 375 | | | | | 380 | | | | | | |
| AAA | GCT | TCG | ATG | GCT | TTC | TTA | CAA | AAG | CAT | TTA | GGG | CTT | CAG | AAA | GAC | 1316 |
| Lys | Ala | Ser | Met | Ala | Phe | Leu | Gln | Lys | His | Leu | Gly | Leu | Gln | Lys | Asp | |
| 385 | | | | 390 | | | | | 395 | | | | | 400 | | |
| TTT | GAT | CAG | TGG | GAC | CCT | CTG | GTG | GAA | GGA | GAT | GAT | GAG | AAC | CTG | ATT | 1364 |
| Phe | Asp | Gln | Trp | Asp | Pro | Leu | Val | Glu | Gly | Asp | Asp | Glu | Asn | Leu | Ile | |
| | | | 405 | | | | | 410 | | | | | 415 | | | |
| CCT | GGG | TCA | CCC | TTT | GAC | GCA | GTC | ACC | CAG | GCC | CCG | GCT | CAG | CAA | CAC | 1412 |
| Pro | Gly | Ser | Pro | Phe | Asp | Ala | Val | Thr | Gln | Ala | Pro | Ala | Gln | Gln | His | |
| | | 420 | | | | | 425 | | | | | 430 | | | | |
| TCT | CCA | GGA | TCA | CAG | ACC | CAG | AAT | TAGAAGAACT | TGCTTGTTAC | ACAGTTGCCT | | | | | | 1466 |
| Ser | Pro | Gly | Ser | Gln | Thr | Gln | Asn | | | | | | | | | |
| | | 435 | | | | 440 | | | | | | | | | | |

TTTAAAAGTA GAGTGACATG AGAGAGAG                                                             1494

( 2 ) INFORMATION FOR SEQ ID NO:22:

( i ) SEQUENCE CHARACTERISTICS:
        ( A ) LENGTH: 2191 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 92..1423

( x i ) SEQUENCE DESCRIPTION: SEQ ID NO:22:

CCGCGCGCTC CGGCCGGGGG ACCCTGGTTC CGGCGAGCGG CTCAGCGCGG CGCCCGGAAG          60

TTTAAGCTGA AACCACTGCT CAGCTTCCAA G ATG TTG CCA CCC AAA CTG CAT           112
                                                Met Leu Pro Pro Lys Leu His
                                                  1                 5

| | | | | | | | | | | | | | | | |
|---|---|---|---|---|---|---|---|---|---|---|---|---|---|---|---|
| GCG | CTT | TTC | TGC | CTC | TGC | AGC | TGC | CTC | ACA | CTG | GTT | CAT | CCT | ATT | GAC | 160 |
| Ala | Leu | Phe | Cys | Leu | Cys | Ser | Cys | Leu | Thr | Leu | Val | His | Pro | Ile | Asp | |
| | | 10 | | | | | 15 | | | | | 20 | | | | |
| TGG | CAA | GAC | CTA | AAT | CCT | GTT | GCC | CAT | ATT | AGA | TCA | TCA | GCA | TGG | GCC | 208 |
| Trp | Gln | Asp | Leu | Asn | Pro | Val | Ala | His | Ile | Arg | Ser | Ser | Ala | Trp | Ala | |
| | 25 | | | | | 30 | | | | | 35 | | | | | |
| AAT | AAA | ATA | CAA | GCT | CTG | ATG | GCT | GCT | GCA | AGT | ATT | AGG | CAA | AGT | AGA | 256 |
| Asn | Lys | Ile | Gln | Ala | Leu | Met | Ala | Ala | Ala | Ser | Ile | Arg | Gln | Ser | Arg | |
| 40 | | | | | 45 | | | | | 50 | | | | | 55 | |
| ATT | CCC | AAA | GGA | AAT | GGA | TCT | TAT | TCT | GTC | GGT | TGT | ACA | GAT | TTG | ATG | 304 |

-continued

| | | | | | | | | | | | | | | |
|---|---|---|---|---|---|---|---|---|---|---|---|---|---|---|
| Ile | Pro | Lys | Gly | Asn | Gly | Ser | Tyr | Ser | Val | Gly | Cys | Thr | Asp | Leu | Met |
| | | | 60 | | | | | 65 | | | | | 70 | |

| TTT | GAT | TAT | ACT | AAT | AAG | GGC | ACC | TTT | TTG | CGT | TTG | TAT | TAT | CCA | TCG | 352 |
|---|---|---|---|---|---|---|---|---|---|---|---|---|---|---|---|---|
| Phe | Asp | Tyr | Thr | Asn | Lys | Gly | Thr | Phe | Leu | Arg | Leu | Tyr | Tyr | Pro | Ser | |
| | | | 75 | | | | 80 | | | | | 85 | | | | |

| CAA | GAG | GAT | GAC | CAC | TCT | GAC | ACG | CTT | TGG | ATC | CCA | AAC | AAA | GAA | TAT | 400 |
| Gln | Glu | Asp | Asp | His | Ser | Asp | Thr | Leu | Trp | Ile | Pro | Asn | Lys | Glu | Tyr | |
| | | | 90 | | | | 95 | | | | 100 | | | | | |

| TTT | TTT | GGT | CTT | AGT | AAA | TAT | CTT | GGA | ACA | CCC | TGG | CTT | ATG | GGC | AAA | 448 |
| Phe | Phe | Gly | Leu | Ser | Lys | Tyr | Leu | Gly | Thr | Pro | Trp | Leu | Met | Gly | Lys | |
| | | 105 | | | | 110 | | | | 115 | | | | | | |

| ATA | TTG | AGC | TTC | TTT | TTT | GGT | TCA | GTG | ACA | ACT | CCT | GCG | AAC | TGG | AAT | 496 |
| Ile | Leu | Ser | Phe | Phe | Phe | Gly | Ser | Val | Thr | Thr | Pro | Ala | Asn | Trp | Asn | |
| 120 | | | | | 125 | | | | 130 | | | | | 135 | | |

| TCC | CCT | CTG | AGG | ACT | GGT | GAA | AAA | TAT | CCA | CTG | ATT | GTT | TTT | TCT | CAT | 544 |
| Ser | Pro | Leu | Arg | Thr | Gly | Glu | Lys | Tyr | Pro | Leu | Ile | Val | Phe | Ser | His | |
| | | | | 140 | | | | 145 | | | | | 150 | | | |

| GGT | CTT | GGA | GCA | TTC | CGG | ACA | ATT | TAT | TCT | GCT | ATT | GGC | ATT | GAT | CTA | 592 |
| Gly | Leu | Gly | Ala | Phe | Arg | Thr | Ile | Tyr | Ser | Ala | Ile | Gly | Ile | Asp | Leu | |
| | | 155 | | | | 160 | | | | 165 | | | | | | |

| GCA | TCA | CAT | GGG | TTC | ATC | GTT | GCT | GCT | ATA | GAA | CAC | AGA | GAT | GGA | TCC | 640 |
| Ala | Ser | His | Gly | Phe | Ile | Val | Ala | Ala | Ile | Glu | His | Arg | Asp | Gly | Ser | |
| | | 170 | | | | 175 | | | | 180 | | | | | | |

| GCC | TCT | GCG | ACT | TAC | TAT | TTC | AAG | GAC | CAG | TCT | GCT | GCA | GAA | ATA | GGG | 688 |
| Ala | Ser | Ala | Thr | Tyr | Tyr | Phe | Lys | Asp | Gln | Ser | Ala | Ala | Glu | Ile | Gly | |
| 185 | | | | | 190 | | | | 195 | | | | | | | |

| AAC | AAA | TCT | TGG | TCT | TAT | CTT | CAA | GAA | CTA | AAA | CCA | GGG | GAT | GAG | GAG | 736 |
| Asn | Lys | Ser | Trp | Ser | Tyr | Leu | Gln | Glu | Leu | Lys | Pro | Gly | Asp | Glu | Glu | |
| 200 | | | | 205 | | | | 210 | | | | | | 215 | | |

| ATA | CAT | GTT | CGA | AAT | GAG | CAG | GTA | CAG | AAA | AGG | GCA | AAG | GAG | TGC | TCC | 784 |
| Ile | His | Val | Arg | Asn | Glu | Gln | Val | Gln | Lys | Arg | Ala | Lys | Glu | Cys | Ser | |
| | | | | 220 | | | | 225 | | | | | 230 | | | |

| CAA | GCT | CTC | AAC | TTG | ATT | CTG | GAC | ATT | GAT | CAT | GGA | AGG | CCA | ATT | AAG | 832 |
| Gln | Ala | Leu | Asn | Leu | Ile | Leu | Asp | Ile | Asp | His | Gly | Arg | Pro | Ile | Lys | |
| | | | 235 | | | | | 240 | | | | | 245 | | | |

| AAT | GTA | CTA | GAC | TTA | GAG | TTT | GAT | GTG | GAA | CAA | CTG | AAG | GAC | TCT | ATT | 880 |
| Asn | Val | Leu | Asp | Leu | Glu | Phe | Asp | Val | Glu | Gln | Leu | Lys | Asp | Ser | Ile | |
| | | 250 | | | | | 255 | | | | | 260 | | | | |

| GAC | AGG | GAT | AAA | ATA | GCA | GTA | ATT | GGA | CAT | TCT | TTT | GGT | GGA | GCC | ACA | 928 |
| Asp | Arg | Asp | Lys | Ile | Ala | Val | Ile | Gly | His | Ser | Phe | Gly | Gly | Ala | Thr | |
| | 265 | | | | | 270 | | | | | 275 | | | | | |

| GTT | CTT | CAG | GCT | CTT | AGT | GAA | GAC | CAG | AGA | TTT | AGG | TGC | GGG | ATT | GCC | 976 |
| Val | Leu | Gln | Ala | Leu | Ser | Glu | Asp | Gln | Arg | Phe | Arg | Cys | Gly | Ile | Ala | |
| 280 | | | | | 285 | | | | | 290 | | | | | 295 | |

| TTG | GAT | GCA | TGG | ATG | CTT | CCA | CTG | GAT | GAT | GCA | ATA | TAT | TCC | AGA | ATC | 1024 |
| Leu | Asp | Ala | Trp | Met | Leu | Pro | Leu | Asp | Asp | Ala | Ile | Tyr | Ser | Arg | Ile | |
| | | | | 300 | | | | | 305 | | | | | 310 | | |

| CCT | CAG | CCC | CTC | TTT | TTT | ATT | AAC | TCG | GAA | CGG | TTC | CAA | TTT | CCT | GAG | 1072 |
| Pro | Gln | Pro | Leu | Phe | Phe | Ile | Asn | Ser | Glu | Arg | Phe | Gln | Phe | Pro | Glu | |
| | | | 315 | | | | | 320 | | | | | 325 | | | |

| AAT | ATC | AAA | AAA | ATG | AAA | AAA | TGC | TAC | TCA | CCT | GAC | AAA | GAA | AGA | AAA | 1120 |
| Asn | Ile | Lys | Lys | Met | Lys | Lys | Cys | Tyr | Ser | Pro | Asp | Lys | Glu | Arg | Lys | |
| | | 330 | | | | | 335 | | | | | 340 | | | | |

| ATG | ATT | ACA | ATC | AGG | GGT | TCA | GTC | CAT | CAG | AAC | TTT | GCT | GAT | TTC | ACT | 1168 |
| Met | Ile | Thr | Ile | Arg | Gly | Ser | Val | His | Gln | Asn | Phe | Ala | Asp | Phe | Thr | |
| | 345 | | | | | 350 | | | | | 355 | | | | | |

| TTT | ACA | ACT | GGC | AAA | ATA | GTT | GGA | TAC | ATA | TTC | ACA | TTA | AAA | GGA | GAT | 1216 |
| Phe | Thr | Thr | Gly | Lys | Ile | Val | Gly | Tyr | Ile | Phe | Thr | Leu | Lys | Gly | Asp | |
| 360 | | | | | 365 | | | | | 370 | | | | | 375 | |

| ATA | GAT | TCA | AAT | GTA | GCA | ATT | GAT | CTT | TGC | AAC | AAA | GCT | TCA | TTG | GCA | 1264 |

-continued

```
        Ile  Asp  Ser  Asn  Val  Ala  Ile  Asp  Leu  Cys  Asn  Lys  Ala  Ser  Leu  Ala
                       380                      385                      390

TTT  TTA  CAA  AAG  CAT  TTA  GGA  CTG  CGG  AAA  GAT  TTT  GAT  CAG  TGG  GAT           1312
Phe  Leu  Gln  Lys  His  Leu  Gly  Leu  Arg  Lys  Asp  Phe  Asp  Gln  Trp  Asp
          395                      400                      405

TCT  TTG  ATT  GAA  GGA  AAA  GAC  GAA  AAT  CTT  ATG  CCA  GGG  ACC  AAC  ATT           1360
Ser  Leu  Ile  Glu  Gly  Lys  Asp  Glu  Asn  Leu  Met  Pro  Gly  Thr  Asn  Ile
               410                      415                      420

AAC  ATC  ACC  AAC  GAA  CAT  GAC  ACT  CTA  CAG  AAC  TCT  CCA  GAA  GCA  GAG           1408
Asn  Ile  Thr  Asn  Glu  His  Asp  Thr  Leu  Gln  Asn  Ser  Pro  Glu  Ala  Glu
          425                      430                      435

AAA  TCG  AAT  TTA  GAT  TAAAAGCACT  TTTTTAAGA  TCTTGTTTAA  AAACTGTCAA                   1463
Lys  Ser  Asn  Leu  Asp
440

AAAATGTGTG  TATGACTTTT  AATATATTTT  CTCAAATAAC  TCATATTGGA  AAATGTAGGC                   1523

TATCCCATAA  AAGTGATTGA  AGCTTGGACT  AGGAGGTTTT  TTTCTTTAAA  GAAAGATTGG                   1583

TGTCTATCGA  AATCATGCCA  GCCTAAATTT  TAATTTTACT  AAAATGATGC  TGTGTCAAAA                   1643

TTAATAACTA  CTTTTACATT  CTTTAATGGA  CAAGTATAAC  AGGCACAAGG  CTAATGAAAA                   1703

CGTGTTGCAA  TGACATAACA  ATCCCTAAAA  ATACAGATGT  TCTTGCCTCT  TTTTCTATT                    1763

ATAATTGAGT  TTTAGCAACA  TGTTATGCTA  GGTAGAATTT  GGAAGCACTT  CCCTTTGACT                   1823

TTTGGTCATG  ATAAGAAAAA  TTAGATCAAG  CAAATGATAA  AAGCAGTGTT  TTACCAAGGA                   1883

TTAGGGATAC  TGAACAATTT  CACTATGGTA  ACTGAATGGG  GAGTGACCAA  GGGTAAAAAT                   1943

ATTAAAGCCA  AGGCAAAGGC  AGCAGATTAG  AATGGATTAA  AGAGAGTTTA  TAATTTGTTT                   2003

GCATTTACTT  GATGGTTTAT  CTCATGGATT  CATGAGTCAA  GAAAGGTGCG  TAGGACAGGC                   2063

CAGGGATTCC  AGTTATAACA  CATTATTCAC  CCAAAGGGTT  CTTTAATTCT  GTATGAGTAT                   2123

TGGGAGTGGA  TTAGCACAAT  AGAGGCATAT  GTTGCTTTAA  AAAAAAAAAA  AAAAAAAAA                    2183

AAAAAAAA                                                                                2191
```

( 2 ) INFORMATION FOR SEQ ID NO:23:

( i ) SEQUENCE CHARACTERISTICS:
        ( A ) LENGTH: 517 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 2..514

( x i ) SEQUENCE DESCRIPTION: SEQ ID NO:23:

```
G  GGG  CAT  TCT  TTT  GGA  GGA  GCA  ACA  GTT  TTT  CAA  GCC  CTA  AGT  GAA            46
   Gly  His  Ser  Phe  Gly  Gly  Ala  Thr  Val  Phe  Gln  Ala  Leu  Ser  Glu
    1              5                        10                       15

GAC  CAG  AGA  TTC  AGA  TGT  GGG  ATT  GCC  CTT  GAT  CCG  TGG  ATG  TTT  CCC           94
Asp  Gln  Arg  Phe  Arg  Cys  Gly  Ile  Ala  Leu  Asp  Pro  Trp  Met  Phe  Pro
               20                       25                       30

GTG  AGT  GAG  GAG  CTG  TAC  TCC  AGA  GTT  CCT  CAG  CCT  CTC  TTC  TTT  ATC           142
Val  Ser  Glu  Glu  Leu  Tyr  Ser  Arg  Val  Pro  Gln  Pro  Leu  Phe  Phe  Ile
          35                       40                       45

AAC  TCT  GCC  GAA  TTC  CAG  ACT  CCA  AAG  GAC  ATT  GCA  AAA  ATG  AAA  AAC           190
Asn  Ser  Ala  Glu  Phe  Gln  Thr  Pro  Lys  Asp  Ile  Ala  Lys  Met  Lys  Asn
          50                       55                       60

TTC  TAC  CAG  CCT  GAC  AAG  GAA  AGG  AAA  ATG  ATT  ACG  ATC  AAG  GGC  TCA           238
```

| | | | | | | | | | | | | | | | | |
|---|---|---|---|---|---|---|---|---|---|---|---|---|---|---|---|---|
| Phe | Tyr | Gln | Pro | Asp | Lys | Glu | Arg | Lys | Met | Ile | Thr | Ile | Lys | Gly | Ser | |
| | 65 | | | | | 70 | | | | | 75 | | | | | |

| GTG | CAC | CAG | AAT | TTT | GCT | GAC | GGG | ACT | TTT | GTA | ACT | GGC | AAA | ATA | ATT | 286 |
|---|---|---|---|---|---|---|---|---|---|---|---|---|---|---|---|---|
| Val | His | Gln | Asn | Phe | Ala | Asp | Gly | Thr | Phe | Val | Thr | Gly | Lys | Ile | Ile | |
| 80 | | | | | 85 | | | | | 90 | | | | | 95 | |

| GGA | AAC | AAG | CTG | TCA | CTG | AAA | GGA | GAC | ATA | GAC | TCC | AGA | GTT | GCC | ATA | 334 |
|---|---|---|---|---|---|---|---|---|---|---|---|---|---|---|---|---|
| Gly | Asn | Lys | Leu | Ser | Leu | Lys | Gly | Asp | Ile | Asp | Ser | Arg | Val | Ala | Ile | |
| | | | | | 100 | | | | | 105 | | | | | 110 | |

| GAC | CTC | ACC | AAC | AAG | GCT | TCC | TTG | GCT | TTC | TTA | CAA | AAA | CAT | TTA | GGA | 382 |
|---|---|---|---|---|---|---|---|---|---|---|---|---|---|---|---|---|
| Asp | Leu | Thr | Asn | Lys | Ala | Ser | Leu | Ala | Phe | Leu | Gln | Lys | His | Leu | Gly | |
| | | | 115 | | | | | 120 | | | | | 125 | | | |

| CTT | CAT | AAA | GAC | TTT | GAT | CAG | TGG | GAC | TGT | CTG | GTG | GAG | GGA | GAG | AAC | 430 |
|---|---|---|---|---|---|---|---|---|---|---|---|---|---|---|---|---|
| Leu | His | Lys | Asp | Phe | Asp | Gln | Trp | Asp | Cys | Leu | Val | Glu | Gly | Glu | Asn | |
| | | 130 | | | | | 135 | | | | | 140 | | | | |

| GAG | AAC | CTC | ATC | CCG | GGG | TCA | CCC | TTT | GAT | GTA | GTC | ACC | CAG | TCC | CCG | 478 |
|---|---|---|---|---|---|---|---|---|---|---|---|---|---|---|---|---|
| Glu | Asn | Leu | Ile | Pro | Gly | Ser | Pro | Phe | Asp | Val | Val | Thr | Gln | Ser | Pro | |
| | 145 | | | | | 150 | | | | | 155 | | | | | |

| GCT | CTG | CAG | AGT | TCT | CCC | GGA | TCA | CAC | AAC | CAG | AAT | TAG | | | | 517 |
|---|---|---|---|---|---|---|---|---|---|---|---|---|---|---|---|---|
| Ala | Leu | Gln | Ser | Ser | Pro | Gly | Ser | His | Asn | Gln | Asn | | | | | |
| 160 | | | | | 165 | | | | | 170 | | | | | | |

( 2 ) INFORMATION FOR SEQ ID NO:24:

( i ) SEQUENCE CHARACTERISTICS:
        ( A ) LENGTH: 580 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..580

( x i ) SEQUENCE DESCRIPTION: SEQ ID NO:24:

| CAA | GTA | CTG | ATG | GCT | GCT | GCA | AGC | TTT | GGC | GAA | CGT | AAA | ATC | CCT | AAG | 48 |
|---|---|---|---|---|---|---|---|---|---|---|---|---|---|---|---|---|
| Gln | Val | Leu | Met | Ala | Ala | Ala | Ser | Phe | Gly | Glu | Arg | Lys | Ile | Pro | Lys | |
| 1 | | | | 5 | | | | | 10 | | | | | 15 | | |

| GGA | AAT | GGG | CCT | TAT | TCC | GTT | GGT | TGT | ACA | GAC | TTA | ATG | TTT | GAT | TAC | 96 |
|---|---|---|---|---|---|---|---|---|---|---|---|---|---|---|---|---|
| Gly | Asn | Gly | Pro | Tyr | Ser | Val | Gly | Cys | Thr | Asp | Leu | Met | Phe | Asp | Tyr | |
| | | | 20 | | | | | 25 | | | | | 30 | | | |

| ACT | AAA | AAG | GGC | ACC | TTC | TTG | CGT | TTA | TAT | TAT | CCA | TCC | CAA | GAT | GAT | 144 |
|---|---|---|---|---|---|---|---|---|---|---|---|---|---|---|---|---|
| Thr | Lys | Lys | Gly | Thr | Phe | Leu | Arg | Leu | Tyr | Tyr | Pro | Ser | Gln | Asp | Asp | |
| | | 35 | | | | | 40 | | | | | 45 | | | | |

| GAT | CGC | CTT | GAC | ACC | CTT | TGG | ATC | CCA | AAT | AAG | GAG | TAT | TTT | TGG | GGT | 192 |
|---|---|---|---|---|---|---|---|---|---|---|---|---|---|---|---|---|
| Asp | Arg | Leu | Asp | Thr | Leu | Trp | Ile | Pro | Asn | Lys | Glu | Tyr | Phe | Trp | Gly | |
| | 50 | | | | | 55 | | | | | 60 | | | | | |

| CTT | AGC | AAG | TAT | CTT | GGA | AAA | CAC | TGG | CTT | ATG | GGC | AAC | ATT | TTG | AGT | 240 |
|---|---|---|---|---|---|---|---|---|---|---|---|---|---|---|---|---|
| Leu | Ser | Lys | Tyr | Leu | Gly | Lys | His | Trp | Leu | Met | Gly | Asn | Ile | Leu | Ser | |
| 65 | | | | | 70 | | | | | 75 | | | | | 80 | |

| TTA | CTC | TTT | GGT | TCA | GTG | ACA | ACT | CCT | GCA | AAC | TGG | AAT | TCC | CCT | CTG | 288 |
|---|---|---|---|---|---|---|---|---|---|---|---|---|---|---|---|---|
| Leu | Leu | Phe | Gly | Ser | Val | Thr | Thr | Pro | Ala | Asn | Trp | Asn | Ser | Pro | Leu | |
| | | | | 85 | | | | | 90 | | | | | 95 | | |

| AGG | CCT | GGT | GAA | AAA | TAC | CCA | CTT | GTT | GTT | TTT | TCT | CAT | GGT | CTT | GGA | 336 |
|---|---|---|---|---|---|---|---|---|---|---|---|---|---|---|---|---|
| Arg | Pro | Gly | Glu | Lys | Tyr | Pro | Leu | Val | Val | Phe | Ser | His | Gly | Leu | Gly | |
| | | | 100 | | | | | 105 | | | | | 110 | | | |

| GCA | TTC | AGG | ACA | ATT | TAT | TCT | GCT | ATT | GGC | ATT | GAC | CTG | GCA | TCT | CAT | 384 |
|---|---|---|---|---|---|---|---|---|---|---|---|---|---|---|---|---|
| Ala | Phe | Arg | Thr | Ile | Tyr | Ser | Ala | Ile | Gly | Ile | Asp | Leu | Ala | Ser | His | |
| | | 115 | | | | | 120 | | | | | 125 | | | | |

| GGG | TTT | ATA | GTT | GCT | GCT | GTA | GAA | CAC | AGA | GAT | AGA | TCT | GCA | TCT | GCA | 432 |
|---|---|---|---|---|---|---|---|---|---|---|---|---|---|---|---|---|
| Gly | Phe | Ile | Val | Ala | Ala | Val | Glu | His | Arg | Asp | Arg | Ser | Ala | Ser | Ala | |
| | 130 | | | | | 135 | | | | | 140 | | | | | |

```
ACT TAC TAT TTC AAG AAC CAA TCT GCT GCA GAA ATA GGG AAA AAG TCT         480
Thr Tyr Tyr Phe Lys Asn Gln Ser Ala Ala Glu Ile Gly Lys Lys Ser
145                 150                 155                 160

TGG CTC TAC CTT AGA ACC CTG AAA GAA GAG GAG GAG ATA CAT ATA CGA         528
Trp Leu Tyr Leu Arg Thr Leu Lys Glu Glu Glu Glu Ile His Ile Arg
                165                 170                 175

AAT AAG CAG GTA CGA CAA AGA GCA AAA GAA TGT TCC CAA GCT CTC AGT         576
Asn Lys Gln Val Arg Gln Arg Ala Lys Glu Cys Ser Gln Ala Leu Ser
                180                 185                 190

CTG A                                                                    580
Leu
```

(2) INFORMATION FOR SEQ ID NO:25:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

TATTCTAGAA TTATGATACA AGTATTAATG GCTGCTGCAA G                            41

(2) INFORMATION FOR SEQ ID NO:26:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

ATTGATATCC TAATTGTATT TCTCTATTCC TG                                      32

PLATELET-ACTIVATING FACTOR ACETYLHYDROLASE

This application is a continuation-in-part of co-pending U.S. patent application Ser. No. 08/133,803 filed Oct. 6, 1993.

FIELD OF THE INVENTION

The present invention relates generally to platelet-activating factor acetylhydrolase and more specifically to novel purified and isolated polynucleotides encoding human plasma platelet-activating factor acetylhydrolase, to the platelet-activating factor acetylhydrolase products encoded by the polynucleotides, to materials and methods for the recombinant production of platelet-activating factor acetylhydrolase products and to antibody substances specific for platelet-activating factor acetylhydrolase.

BACKGROUND

Platelet-activating factor (PAF) is a biologically active phospholipid synthesized by various cell types. In vivo and at normal concentrations of $10^{-10}$ to $10^{-9}$M, PAF activates target cells such as platelets and neutrophils by binding to specific G protein-coupled cell surface receptors [Venable et al., *J. Lipid Res.*, 34:691–701 (1993)]. PAF has the structure 1-O-alkyl-2-acetyl-sn-glycero-3-phosphocholine. For optimal biological activity, the sn-1 position of the PAF glycerol backbone must be in an ether linkage with a fatty alcohol and the sn-3 position must have a phosphocholine head group.

PAF functions in normal physiological processes (e.g., inflammation, hemostasis and parturition) and is implicated in pathological inflammatory responses (e.g., asthma, anaphylaxis, septic shock and arthritis) [Venable et al., supra, and Lindsberg et al., *Ann. Neurol.*, 30:117–129 (1991)]. The likelihood of PAF involvment in pathological responses has prompted attempts to modulate the activity of PAF and the major focus of these attempts has been the development of antagonists of PAF activity which interfere with binding of PAF to cell surface receptors. See, for example, Heuer et al., *Clin. Exp. Allergy*, 22:980–983 (1992).

The synthesis and secretion of PAF as well as its degradation and clearance appear to be tightly controlled. To the extent that pathological inflammatory actions of PAF result from a failure of PAF regulatory mechanisms giving rise to excessive production, inappropriate production or lack of degradation, an alternative means of modulating the activity of PAF would involve mimicing or augmenting the natural process by which resolution of inflammation occurs. Macrophages [Stafforini et al., *J. Biol. Chem.*, 265(17) :9682–9687 (1990)], hepatocytes and the human hepatoma cell line HepG2 [Satoh et al., *J. Clin. Invest.*, 87:476–481 (1991) and Tarbet et al., *J. Biol. Chem.*, 266(25) :16667–16673 (1991)] have been reported to release an enzymatic activity, PAF acetylhydrolase (PAF-AH), that inactivates PAF. In addition to inactivating PAF, PAF-AH also inactivates oxidatively fragmented phospholipids such as products of the arachidonic acid cascade that mediate inflammation. See, Stremler et al., *J. Biol. Chem.*, 266(17) :11095–11103 (1991). The inactivation of PAF by PAF-AH occurs primarily by hydrolysis of the PAF sn-2 acetyl group and PAF-AH metabolizes oxidatively fragmented phospholipids by removing sn-2 acyl groups. Two types of PAF-AH have been identified: cytoplasmic forms found in a variety of cell types and tissues such as endothelial cells and erythrocytes, and an extracellular form found in plasma and serum. Plasma PAF-AH does not hydrolyze intact phospholipids except for PAF and this substrate specificity allows the enzyme to circulate in vivo in a fully active state without adverse effects. The plasma PAF-AH appears to account for all of the PAF degradation in human blood ex vivo [Stafforini et al., *J. Biol. Chem.*, 262(9):4223–4230 (1987)].

While the cytoplasmic and plasma forms of PAF-AH appear to have identical substrate specificity, plasma PAF-AH has biochemical characteristics which distinguish it from cytoplasmic PAF-AH and from other characterized lipases. Specifically, plasma PAF-AH is associated with lipoprotein particles, is inhibited by diisopropyl fluorophosphate, is not affected by calcium ions, is relatively insensitive to proteolysis, and has an apparent molecular weight of 43,000 daltons. See, Stafforini et al. (1987), supra. The same Stafforini et al. article describes a procedure for partial purification of PAF-AH from human plasma and the amino acid composition of the plasma material obtained by use of the procedure. Cytoplasmic PAF-AH has been purified from erythrocytes as reported in Stafforini et al., *J. Biol. Chem.*, 268(6):3857–3865 (1993) and ten amino terminal residues of cytoplasmic PAF-AH are also described in the article. Hattori et al., *J. Biol. Chem.*, 268(25):18748–18753 (1993) describes the purification of cytoplasmic PAF-AH from bovine brain. Subsequent to filing of the parent application hereto the nucleotide sequence of bovine brain cytoplasmic PAF-AH was published in Hattori et al, *J. Biol. Chem.*, 269(237):23150–23155 (1994). To date no nucleotide sequence for the plasma form of PAF-AH has been published.

The recombinant production of PAF-AH would make possible the use of exogenous PAF-AH to mimic or augment normal processes of resolution of inflammation in vivo. The administration of PAF-AH would provide a physiological advantage over administration of PAF receptor antagonists because PAF-AH is a product normally found in plasma. Moreover, because PAF receptor antagonists which are structurally related to PAF inhibit native PAF-AH activity, the desirable metabolism of PAF and of oxidatively fragmented phospholipids is thereby prevented. Thus, the inhibition of PAF-AH activity by PAF receptor antagonists counteracts the competitive blockade of the PAF receptor by the antagonists. See, Stremler et al., supra. In addition, in locations of acute inflammation, for example, the release of oxidants results in inactivation of the native PAF-AH enzyme in turn resulting in elevated local levels of PAF and PAF-like compounds which would compete with any exogenously administed PAF receptor antagonist for binding to the PAF receptor. In contrast, treatment with recombinant PAF-AH would augment endogenous PAF-AH activity and compensate for any inactivated endogenous enzyme.

There thus exists a need in the art to identify and isolate polynucleotide sequences encoding human plasma PAF-AH, to develop materials and methods useful for the recombinant production of PAF-AH and to generate reagents for the detection of PAF-AH in plasma.

SUMMARY OF THE INVENTION

The present invention provides novel purified and isolated polynucleotides (i.e., DNA and RNA both sense and antisense strands) encoding human plasma PAF-AH or enzymatically active fragments thereof. Preferred DNA sequences of the invention include genomic and cDNA sequences as well as wholly or partially chemically synthesized DNA sequences. The DNA sequence encoding PAF- AH that is set out in SEQ ID NO: 7 and DNA sequences which hybridize to the noncoding strand thereof under standard stringent conditions or which would hybridize but for the redundancy of the genetic code, are contemplated by the invention. Also contemplated by the invention are biological replicas (i.e., copies of isolated DNA sequences made in vivo or in vitro) of DNA sequences of the invention. Autonomously replicating recombinant constructions such as plasmid and viral DNA vectors incorporating PAF-AH sequences and especially vectors wherein DNA encoding PAF-AH is operatively linked to an endogenous or exogenous expression control DNA sequence and a transcription terminator are also provided.

According to another aspect of the invention, procaryotic or eucaryotic host cells are stably transformed with DNA sequences of the invention in a manner allowing the desired PAF-AH to be expressed therein. Host cells expressing PAF-AH products can serve a variety of useful purposes. Such cells constitute a valuable source of immunogen for the development of antibody substances specifically immunoreactive with PAF-AH. Host cells of the invention are conspicuously useful in methods for the large scale production of PAF-AH wherein the cells are grown in a suitable culture medium and the desired polypeptide products are isolated from the cells or from the medium in which the cells are grown by, for example, immunoaffinity purification.

A non-immunological method contemplated by the invention for purifying PAF-AH from plasma includes the following steps: (a) isolating low density lipoprotein particles; (b) solubilizing said low density lipoprotein particles in a buffer comprising 10 mM CHAPS to generate a first PAF-AH enzyme solution; (c) applying said first PAF-AH enzyme solution to a DEAE anion exchange column; (d) washing said DEAE anion exchange column using an approximately pH 7.5 buffer comprising 1 mM CHAPS; (e) eluting PAF-AH enzyme from said DEAE anion exchange column in fractions using approximately pH 7.5 buffers comprising a gradient of 0 to 0.5M NaCl; (f) pooling fractions eluted from said DEAE anion exchange column having PAF-AH enzymatic activity; (g) adjusting said pooled, active fractions from said DEAE anion exchange column to 10 mM CHAPS to generate a second PAF-AH enzyme solution; (h) applying said second PAF-AH enzyme solution to a blue dye ligand affinity column; (i) eluting PAF-AH enzyme from said blue dye ligand affinity column using a buffer comprising 10 mM CHAPS and a chaotropic salt; (j) applying the eluate from said blue dye ligand affinity column to a Cu ligand affinity column; (k) eluting PAF-AH enzyme from said Cu ligand affinity column using a buffer comprising 10 mM CHAPS and imidazole; (l) subjecting the eluate from said Cu ligand affinity column to SDS-PAGE; and (m) isolating the approximately 44 kDa PAF-AH enzyme from the SDS-polyacrylamide gel. Preferably, the buffer of step (b) is 25 mM Tris-HCl, 10 mM CHAPS, pH 7.5; the buffer of step (d) is 25 mM Tris-HCl, 1 mM CHAPS; the column of step (h) is a Blue Sepharose Fast Flow column; the buffer of step (i) is 25 mM Tris-HCl, 10 mM CHAPS, 0.5M KSCN, pH 7.5; the column of step (j) is a Cu Chelating Sepharose column; and the buffer of step (k) is 25 mM Tris-HCl, 10 mM CHAPS, 0.5M NaCl, 50 mM imidazole at a pH in a range of about pH 7.5–8.0.

A method contemplated by the invention for purifying enzymatically-active PAF-AH from E. coli producing PAF-AH includes the steps of: (a) preparing a centrifugation supernatant from lysed E. coli producing PAF-AH enzyme; (b) applying said centrifugation supernatant to a blue dye ligand affinity column; (c) eluting PAF-AH enzyme from said blue dye ligand affinity column using a buffer comprising 10 mM CHAPS and a chaotropic salt; (d) applying said eluate from said blue dye ligand affinity column to a Cu ligand affinity column; and (e) eluting PAF-AH enzyme from said Cu ligand affinity column using a buffer comprising 10 mM CHAPS and imidazole. Preferably, the column of step (b) is a Blue Sepharose Fast Flow column; the buffer of step (c) is 25 mM Tris-HCl, 10 mM CHAPS, 0.5M KSCN, pH. 7.5; the column of step (d) is a Cu Chelating Sepharose column; and the buffer of step (e) is 25 mM Tris-HCl, 10 mM CHAPS, 0.5M NaCl, 100 mM imidazole, pH 7.5.

Another method contemplated by the invention for purifying enzymatically-active PAF-AH from E. coli producing PAF-AH includes the steps of: (a) preparing a centrifugation supernatant from lysed E. coli producing PAF-AH enzyme; (b) diluting said centrifugation supernatant in a low pH buffer comprising 10 mM CHAPS; (c) applying said diluted centrifugation supernatant to a cation exchange column equilibrated at about pH 7.5; (d) eluting PAF-AH enzyme from said cation exchange column using 1M salt; (e) raising the pH of said eluate from said cation exhange column and adjusting the salt concentration of said eluate to about 0.5M salt; (f) applying said adjusted eluate from said cation exchange column to a blue dye ligand affinity column; (g) eluting PAF-AH enzyme from said blue dye ligand affinity column using a buffer comprising about 2M to about 3M salt; and (h) dialyzing said eluate from said blue dye ligand affinity column using a buffer comprising about 0.1% Tween. Preferably, the buffer of step (b) is 25 mM MES, 10 mM CHAPS, 1 mM EDTA, pH 4.9; the column of step (c) is an S sepharose column equilibrated in 25 mM MES, 10 mM CHAPS, 1 mM EDTA, 50 mM NaCl, pH 5.5; PAF-AH is eluted in step (d) using 1 mM NaCl; the pH of the eluate in step (e) is adjusted to pH 7.5 using 2M Tris base; the column in step (f) is a sepharose column; the buffer in step (g) is 25 mM Tris, 10 mM CHAPS, 3M NaCl, 1 mM EDTA, pH 7.5; and the buffer in step (h) is 25 mM Tris, 0.5M NaCl, 0.1% Tween 80, pH 7.5.

PAF-AH products may be obtained as isolates from natural cell sources or may be chemically synthesized, but are preferably produced by recombinant procedures involving procaryotic or eucaryotic host cells of the invention. PAF-AH products having part or all of the amino acid sequence set out in SEQ ID NO: 8 are contemplated. The use of mammalian host cells is expected to provide for such post-translational modifications (e.g., myristolation, glycosylation, truncation, lipidation and tyrosine, serine or threonine phosphorylation) as may be needed to confer optimal biological activity on recombinant expression products of the invention. PAF-AH products of the invention may be full length polypeptides, fragments or variants. Variants may comprise PAF-AH analogs wherein one or more of the specified (i.e., naturally encoded) amino acids is deleted or replaced or wherein one or more nonspecified amino acids are added: (1) without loss of one or more of the enzymatic activities or immunological characteristics specific to PAF-AH; or (2) with specific disablement of a particular biological activity of PAF-AH. Proteins or other molecules that bind to PAF-AH may be used to modulate its activity.

Also comprehended by the present invention are antibody substances (e.g., monoclonal and polyclonal antibodies, single chain antibodies, chimeric antibodies, CDR-grafted antibodies and the like) and other binding proteins specific for PAF-AH. Specifically illustrating binding proteins of the invention are the monoclonal antibodies produced by hybridomas 90G11D and 90F2D which were deposited with the American Type Culture Collection (ATCC), 12301 Parklawn Drive, Rockville, Md. 20852 on Sep. 30, 1994 and were respectively assigned Accession Nos. HB 11724 and HB 11725. Proteins or other molecules (e.g., lipids or small molecules) which specifically bind to PAF-AH can be identified using PAF-AH isolated from plasma, recombinant PAF-AH, PAF-AH variants or cells expressing such products. Binding proteins are useful, in turn, in compositions for immunization as well as for purifying PAF-AH, and are useful for detection or quantification of PAF-AH in fluid and tissue samples by known immunological procedures. Anti-idiotypic antibodies specific for PAF-AH-specific antibody substances are also contemplated.

The scientific value of the information contributed through the disclosures of DNA and amino acid sequences of the present invention is manifest. As one series of examples, knowledge of the sequence of a cDNA for PAF-AH makes possible the isolation by DNA/DNA hybridization of genomic DNA sequences encoding PAF-AH and specifying PAF-AH expression control regulatory sequences such as promoters, operators and the like. DNA/DNA hybridization procedures carried out with DNA sequences of the invention under conditions of stringency standard in the art are likewise expected to allow the isolation of DNAs encoding allelic variants of PAF-AH, other structurally related proteins sharing one or more of the biochemical and/or immunological properties of PAF-AH, and non-human species proteins homologous to PAF-AH. The DNA sequence information provided by the present invention also makes possible the development, by homologous recombination or "knockout" strategies [see, e.g., Kapecchi, *Science*, 244:1288–1292 (1989)], of rodents that fail to express a functional PAF-AH enzyme or that express a variant PAF-AH enzyme. Polynucleotides of the invention when suitably labelled are useful in hybridization assays to detect the capacity of cells to synthesize PAF-AH. Polynucleotides of the invention may also be the basis for diagnostic methods useful for identifying a genetic alteration(s) in the PAF-AH locus that underlies a disease state or states. Also made available by the invention are anti-sense polynucleotides relevant to regulating expression of PAF-AH by those cells which ordinarily express the same.

Administration of PAF-AH preparations of the invention to mammalian subjects, especially humans, for the purpose of ameliorating pathological inflammatory conditions is contemplated. Based on implication of the involvement of PAF in pathological inflammatory conditions, the administration of PAF-AH is indicated, for example, in treatment of asthma [Miwa et al., *J. Clin. Invest.*, 82:1983–1991 (1988); Hsieh et al., *J. Allergy Clin. Immunol.*, 91:650–657 (1993); and Yamashita et al., *Allergy*, 49:60–63 (1994)], anaphylaxis [Venable et al., supra], shock [Venable et al., supra], reperfusion injury and central nervous system ischemia [Lindsberg et at. (1991), supra], antigen-induced arthritis [Zarco et al., *Clin. Exp. Immunol.*, 88:318–323 (1992)], atherogenesis [Handley et al., *Drug Dev. Res.*, 7:361–375 (1986)], Crohn's disease [Denizot et al., *Digestive Diseases and Sciences*, 37(3):432–437 (1992)], ischemic bowel necrosis/necrotizing enterocolitis [Denizot et al., supra and Caplan et al., *Acta Paediatr., Suppl.* 396:11–17 (1994)], ulcerative colitis (Denizot et at., supra), ischemic stroke [Satoh et al., *Stroke*, 23:1090–1092 (1992)], ischemic brain injury [Lindsberg et al., *Stroke*, 21:1452–1457 (1990) and Lindsberg et al. (1991), supra], systemic lupus erythematosus [Matsuzaki et al., *Clinica Chimica Acta*, 210:139–144 (1992)], acute pancreatitis [Kald et al., *Pancreas*, 8(4):440–442 (1993)], septicemia (Kald et at., supra), acute post streptococcal glomerulonephritis [Mezzano et al., *J. Am. Soc. Nephrol.*, 4:235–242 (1993)], pulmonary edema resulting from IL-2 therapy [Rabinovici et al., *J. Clin. Invest.*, 89:1669–1673 (1992)], allergic inflammation [Watanabe et at., *Br. J. Pharmacol.*, 111:123–130 (1994)], ischemic renal failure [Grino et al., *Annals of Internal Medicine*, 121(5):345–347 (1994); preterm labor [Hoffman et al., *Am. J. Obstet. Gynecol.*, 162(2):525–528 (1990) and Maki et al., *Proc. Natl. Acad. Sci. USA*, 85:728–732 (1988)]; and adult respiratory distress syndrome [Rabinovici et al., *J. Appl. Physiol.*, 74(4):1791–1802 (1993); Matsumoto et al., *Clin. Exp. Pharmacol. Physiol.*, 19 509–515 (1992); and Rodriguez-Roisin et al., *J. Clin. Invest.*, 93:188–194 (1994)].

Animal models for many of the foregoing pathological conditions have been described in the art. For example, a mouse model for asthma, rhinitis, and eczema is described in Example 16 herein; a rabbit model for arthritis is described in Zarco et at., supra; rat models for ischemic bowel necrosis/necrotizing enterocolitis are described in Furukawa et al., *Ped. Res.*, 34,(2):237–241 (1993) and Caplan et at., supra; a rabbit model for stroke is described in Lindsberg et al., (1990), supra; a mouse model for lupus is described in Matsuzaki et al., supra; a rat model for acute pancreatitis is described in Kald et al., supra: a rat model for pulmonary edema resulting from IL-2 therapy is described in Rabinovici et al., supra; a rat model of allergic inflammation is described in Watanabe et at., supra); a canine model of renal allograft is described in Watson et al., *Transplantation*, 56(4):1047–1049 (1993); and a rat model of adult respiratory distress syndrome is described in Rabinovici et at., supra.

Specifically contemplated by the invention are PAF-AH compositions for use in methods for treating a mammal susceptible to or suffering from PAF-mediated pathological conditions comprising administering PAF-AH to the mammal in an amount sufficient to supplement endogenous PAF-AH activity and to inactivate pathological amounts of PAF in the mammal.

Therapeutic compositions contemplated by the invention include PAF-AH and a physiologically acceptable diluent or carrier and may also include other agents having anti-inflammatory effects. Dosage amounts indicated would be sufficient to supplement endogenous PAF-AH activity and to inactivate pathological amounts of PAF. For general dosage considerations see Remmington's *Pharmaceutical Sciences*, 18th Edition, Mack Publishing Co., Easton, Pa. (1990). Dosages will vary between about 0.1 to about 1000 μg PAF-AH/kg body weight. Therapeutic compositions of the invention may be administered by various routes depending on the pathological condition to be treated. For example, administration may be by intraveneous, subcutaneous, oral, suppository, and/or pulmonary routes.

For pathological conditions of the lung, administration of PAF-AH by the pulmonary route is particularly indicated. Contemplated for use in pulmonary administration are a wide range of delivery devices including, for example, nebulizers, metered dose inhalers, and powder inhalers, which are standard in the art. Delivery of various proteins to the lungs and circulatory system by inhalation of aerosol formulations has been described in Adjei et al., *Pharm. Res.*, 7(6):565–569 (1990) (leuprolide acetate); Braquet et al., *J. Cardio. Pharm.*, 13(Supp. 5): s. 143–146 (1989) (endothelin-1); Hubbard et al., *Annals of Internal Medicine*, III(3), 206–212 (1989) (α1-antitrypsin); Smith et al., *J. Clin. Invest.*, 84:1145–1146 (1989) (α-1-proteinase inhibitor);

Debs et al., *J. Immunol.*, 140:3482–3488 (1933) (recombinant gamma interferon and tumor necrosis factor alpha); Patent Cooperation Treaty (PCT) International Publication No. WO 94/20069 published Sep. 15, 1994 (recombinant pegylated granulocyte colony stimulating factor).

BRIEF DESCRIPTION OF THE DRAWING

Numerous other aspects and advantages of the present invention will be apparent upon consideration of the following detailed description thereof, reference being made to the drawing wherein.

DETAILED DESCRIPTION

Figure 1:
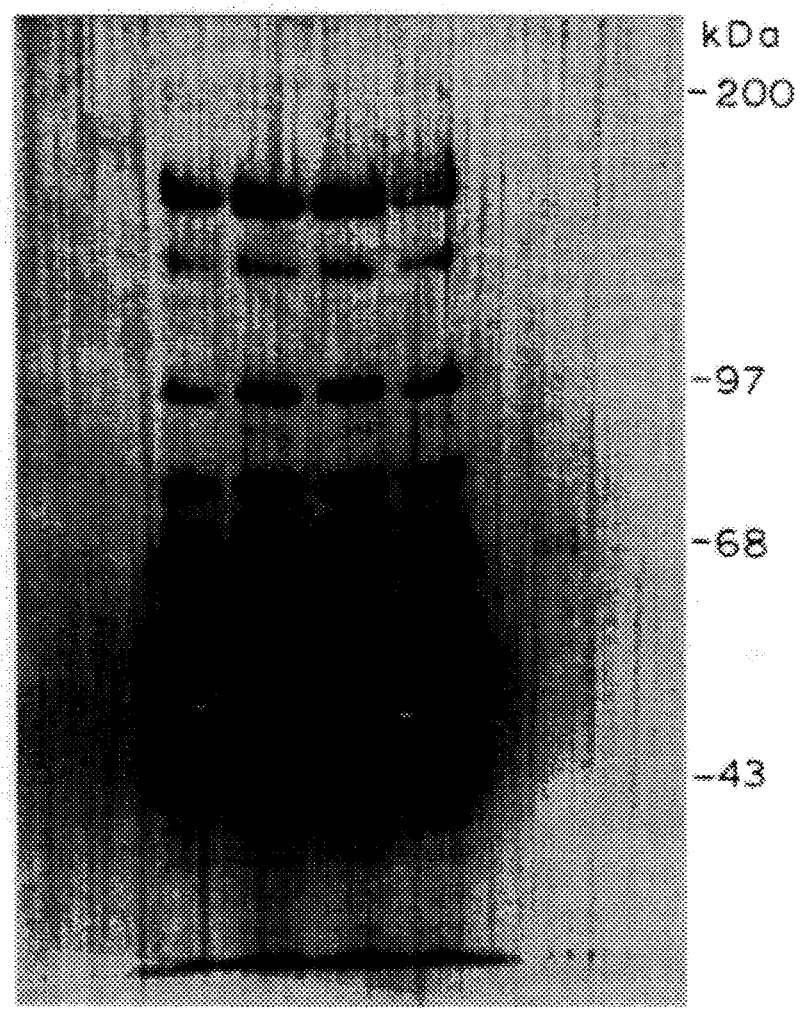
FIG. 1 is a photograph of a PVDF membrane containing PAF-AH purified from human plasma.

The following examples illustrate the invention. Example 1 presents a novel method for the purification of PAF-AH from human plasma. Example 2 describes amino acid microsequencing of the purified human plasma PAF-AH. The cloning of a full length cDNA encoding human plasma PAF-AH is described in Example 3. Identification of a putative splice variant of the human plasma PAF-AH gene is described in Example 4. The cloning of genomic sequences encoding human plasma PAF-AH is described in Example 5. Example 6 desribes the cloning of canine, murine, rodent and macaque cDNAs homologous to the human plasma PAF-AH cDNA. Example 7 presents the results of an assay evidencing the enzymatic activity of recombinant PAF-AH transiently expressed in COS 7 cells. Example 8 describes the expression of human PAF-AH in *E. coli* and *S. cerevisiae*. Example 9 presents a protocol for purification of recombinant PAF-AH from *E. coli* and assays confirming its enzymatic activity. Example 10 describes various recombinant PAF-AH products including amino acid substitution analogs and amino and carboxy-truncated products. Results of a Northern blot assay for expression of human plasma PAF-AH RNA in various tissues and cell lines are presented in Example 11 while results of in situ hybridzation are presented in Example 12. Example 13 describes the development of monoclonal antibodies specific for human plasma PAF-AH. Examples 14, 15, and 16 respectively describe the in vivo therapeutic effect of administration of recombinant PAF-AH products of the invention on acute inflammation, pleurisy and asthma in rats. Example 17 presents the results of immunoassays of serum of human patients exhibiting a deficiency in PAF-AH activity and describes the identification of a genetic lesion in the patients which is apparently responsible for the deficiency.

EXAMPLE 1

PAF-AH was purified from human plasma in order to provide material for amino acid sequencing.

A. Optimization of Purification Conditions

Initially, low density lipoprotein (LDL) particles were precipitated from plasma with phosphotungstate and solubilized in 0.1% Tween 20 and subjected to chromatography on a DEAE column (Pharmacia, Uppsala, Sweden) according to the method of Stafforini et al (1987), supra, but inconsistent elution of PAF-AH activity from the DEAE column required reevaluation of the solubilization and subsequent purification conditions.

Tween 20, CHAPS (Pierce Chemical Co., Rockford, Ill.) and octyl glucoside were evaluated by centrifugation and gel filtration chromatography for their ability to solubilize LDL particles. CHAPS provided 25% greater recovery of solubilized activity than Tween 20 and 300% greater recovery than octyl glucoside. LDL precipitate solubilized with 10 mM CHAPS was then fractionated on a DEAE Sepharose Fast Flow column (an anion exchange column; Pharmacia) with buffer containing 1 mM CHAPS to provide a large pool of partially purified PAF-AH ("the DEAE pool") for evaluation of additional columns.

The DEAE pool was used as starting material to test a variety of chromatography columns for utility in further purifying the PAF-AH activity. The columns tested included: Blue Sepharose Fast Flow (Pharmacia), a dye ligand affinity column; S-Sepharose Fast Flow (Pharmacia), a cation exchange column; Cu Chelating Sepharose (Pharmacia), a metal ligand affinity column; Fractogel S (EM Separations, Gibbstown, N.J.), a cation exchange column; and Sephacryl-200 (Pharmacia), a gel filtration column. These chromatographic procedures all yielded low, unsatisfactory levels of purification when operated in 1 mM CHAPS. Subsequent gel filtration chromatography on Sephacryl S-200 in 1 mM CHAPS generated an enzymatically active fraction which eluted over a broad size range rather than the expected 44 kDa approximate size. Taken together, these results indicated that the LDL proteins were aggregating in solution.

Different LDL samples were therefore evaluated by analytical gel filtration chromatography for aggregation of the PAF-AH activity. Samples from the DEAE pool and of freshly solubilized LDL precipitate were analyzed on Superose 12 (Pharmacia) equilibrated in buffer with 1 mM CHAPS. Both samples eluted over a very broad range of molecular weights with most of the activity eluting above 150 kDa. When the samples were then analyzed on Superose 12 equilibrated with 10 mM CHAPS, the bulk of the activity eluted near 44 kDa as expected for PAF-AH activity. However, the samples contained some PAF-AH activity in the high molecular weight region corresponding to aggregates.

Other samples eluted PAF-AH activity exclusively in the approximately 44 kDa range when they were subsequently tested by gel filtration. These samples were an LDL precipitate solubilized in 10 mM CHAPS in the presence of 0.5M NaCl and a fresh DEAE pool that was adjusted to 10 mM CHAPS after elution from the DEAE column. These data indicate that at least 10 mM CHAPS is required to maintain non-aggregated PAF-AH. Increase of the CHAPS concentration from 1 mM to 10 mM after chromatography on DEAE but prior to subsequent chromatographic steps resulted in dramatic differences in purification. For example, the degree of PAF-AH purification on S-Sepharose Fast Flow was increased from 2-fold to 10-fold. PAF-AH activity bound the Blue Sepharose Fast Flow column irreversibly in 1 mM CHAPS, but the column provided the highest level of purification in 10 mM CHAPS. The DEAE chromatography was not improved with prior addition of 10 mM CHAPS.

Chromatography on Cu Chelating Sepharose after the Blue Sepharose Fast Flow column concentrated PAF-AH activity 15-fold. It was also determined that PAF-AH activity could be recovered from a reduced SDS-polyacrylamide gel, as long as samples were not boiled. The activity of material eluted from the Cu Chelating Sepharose column when subjected to SDS-polyacrylamide gel electrophoresis coincided with a major protein band when the gel was silver stained.

B. PAF-AH Purification Protocol

The novel protocol utilized to purify PAF-AH for amino acid sequencing therefore comprised the following steps which were performed at 4° C. Human plasma was divided into 900 ml aliquots in 1 liter Nalgene bottles and adjusted to pH 8.6. LDL particles were then precipitated by adding 90 ml of 3.85% sodium phosphotungstate followed by 23 ml of 2M $MgCl_2$. The plasma was then centrifuged for 15 minutes at 3600 g. Pellets were resuspended in 800 ml of 0.2% sodium titrate. LDL was precipitated again by adding 10 g NaCl and 24 ml of 2M $MgCl_2$. LDL particles were pelleted by centrifugation for 15 minutes at 3600 g. This wash was repeated twice. Pellets were then frozen at −20° C. LDL particles from 5 L of plasma were resuspended in 5 L of buffer A (25 mM Tris-HCl, 10 mM CHAPS, pH 7.5) and stirred overnight. Solubilized LDL particles were centrifuged at 3600 g for 1.5 hours. Supernatants were combined and filtered with Whatman 113 filter paper to remove any remaining solids. Solubilized LDL supernatant was loaded on a DEAE Sepharose Fast Flow column (11 cm×10 cm; 1 L resin volume; 80 ml/minute) equilibrated in buffer B (25 mM Tris-HCl, 1 mM CHAPS, pH 7.5). The column was washed with buffer B until absorbance returned to baseline. Protein was eluted with an 8 L, 0–0.5M NaCl gradient and 480 ml fractions were collected. This step was necessary to obtain binding to the Blue Sepharose Fast Flow column below. Fractions were assayed for acetylhydrolase activity essentially by the method described in Example 4.

Active fractions were pooled and sufficient CHAPS was added to make the pool about 10 mM CHAPS. The DEAE pool was loaded overnight at 4 ml/minute onto a Blue Sepharose Fast Flow column (5 cm×10 cm; 200 ml bed volume) equilibrated in buffer A containing 0.5M NaCl. The column was washed with the equilibration buffer at 16 ml/minute until absorbance returned to baseline. PAF-AH activity was step eluted with buffer A containing 0.5M KSCN (a chaotropic salt) at 16 ml/minute and collected in 50 ml fractions. This step resulted in greater than 1000-fold purification. Active fractions were pooled, and the pool was adjusted to pH 8.0 with 1M Tris-HCl pH 8.0. The active pool from Blue Sepharose Fast Flow chromatography was loaded onto a Cu Chelating Sepharose column (2.5 cm×2 cm; 10 ml bed volume; 4 ml/minute) equilibrated in buffer C [25 mM Tris-HCl, 10 mM CHAPS, 0.5M NaCl, pH 8.0 (pH 7.5 also worked)], and the column was washed with 50 ml buffer C. PAF-AH activity was eluted with 100 ml 50 mM imidazole in buffer C and collected in 10 ml fractions. Fractions containing PAF-AH activity were pooled and dialyzed against buffer A. In addition to providing a 15-fold concentration of PAF-AH activity, the Cu Chelating Sepharose column gave a small purification. The Cu Chelating Sepharose pool was reduced in 50 mM DTT for 15 minutes at 37° C. and loaded onto a 0.75 mm, 7.5% polyacrylamide gel. Gel slices were cut every 0.5 cm and placed in disposable microfuge tubes containing 200 μl 25 mM Tris-HCl, 10 mM CHAPS, 150 mM NaCl. Slices were ground up and allowed to incubate overnight at 4° C. The supernatant of each gel slice was then assayed for PAF-AH activity to determine which protein band on SDS-PAGE contained PAF-AH activity. PAF-AH activity was found in an approximately 44 kDa band. Protein from a duplicate gel was electrotransferred to a PVDF membrane (Immobilon-P, Millipore) and stained with Coomassie Blue. A photograph of the PVDF membrane is presented in FIG. 1.

As presented in Table I below, approximately 200 μg PAF-AH was purified $2×10^6$-fold from 5 L human plasma. In comparison, a $3×10^4$-fold purification of PAF-AH activity is described in Stafforini et al. (1987), supra.

TABLE 1

| Sample | Vol. (ml) | Activity (cpm × $10^6$) | Total Activity (cpm × $10^9$) | Prot. Conc. (mg/ml) | Specific Activity (cpm × $10^6$) | % Recovery of Activity Step | % Recovery of Activity Cum. | Fold Purification Step | Fold Purification Cum. |
|---|---|---|---|---|---|---|---|---|---|
| Plasma | 5000 | 23 | 116 | 62 | 0.37 | 100 | 100 | 1 | 1 |
| LDL | 4500 | 22 | 97 | 12 | 1.76 | 84 | 84 | 33 | 33 |
| DEAE | 4200 | 49 | 207 | 1.08 | 46 | 212 | 178 | 3.7 | 124 |
| Blue | 165 | 881 | 14 | 0.02 | 54200 | 70 | 126 | 1190 | $1.5 × 10^5$ |
| Cu | 12 | 12700 | 152 | 0.15 | 82200 | 104 | 131 | 1.5 | $2.2 × 10^5$ |
| SDS-PAGE | — | — | — | — | — | — | ~10 | — | $2.2 × 10^6$ |

In summary, the following steps were unique and critical for successful purification of plasma PAF-AH for microsequencing: (1) solubilization and chromotography in 10 mM CHAPS, (2) chromatography on a blue ligand affinity column such as Blue Sepharose Fast Flow, (3) chromatography on a Cu ligand affinity column such as Cu Chelating Sepharose, and (4) elution of PAF-AH from SDS-PAGE.

EXAMPLE 2

For amino acid sequencing, the approximately 44 kDa protein band from the PAF-AH-containing PVDF membrane described in Example 1 was excised and sequenced using an Applied Biosystems 473A Protein sequencer. N-terminal sequence analysis of the ~44 kDa protein band corresponding to the PAF-AH activity indicated that the band contained two major sequences and two minor sequences. The ratio of the two major sequences was 1:1 and it was therefore difficult to interpret the sequence data.

To distinguish the sequences of the two major proteins which had been resolved on the SDS gel, a duplicate PVDF membrane containing the approximately 44 kDa band was cut in half such that the upper part and the lower part of the membrane were separately subjected to sequencing.

The N-terminal sequence obtained for the lower half of the membrane was:

---
SEQ ID NO: 1
F K D L G E E N F K A L V L I A F

---

A search of protein databases revealed this sequence to be a fragment of human serum albumin. The upper half of the same PVDF membrane was also sequenced and the N-terminal amino acid sequence determined was:

---
SEQ ID NO: 2
I Q V L M A A A S F G Q T K I P

---

This sequence did not match any protein in the databases searched and was different from the N-terminal amino acid sequence:

---
SEQ ID NO: 3
M K P L V V F V L G G

--- which was reported for erythrocyte cytoplasmic PAF-AH in Stafforini et al. (1993), supra. The novel sequence (SEQ ID NO: 2) was utilized for cDNA cloning of human plasma PAF-AH as described below in Example 3.

EXAMPLE 3

A full length clone encoding human plasma PAF-AH was isolated from a macrophage cDNA library.

A. Construction Of a Macrophage cDNA Library

Poly A$^+$ RNA was harvested from peripheral blood monocyte-derived macrophages. Double-stranded, blunt-ended cDNA was generated using the Invitrogen Copy Kit (San Diego, Calif.) and BstXI adapters were ligated to the cDNA prior to insertion into the mammalian expression vector, pRc/CMV (Invitrogen). The resulting plasmids were introduced into E. coli strain XL-1 Blue by electroporation. Transformed bacteria were plated at a density of approximately 3000 colonies per agarose plate on a total of 978 plates. Plasmid DNA prepared separately from each plate was retained in individual pools and was also combined into larger pools representing 300,000 clones each.

B. Library Screening by PCR

The macrophage library was screened by the polymerase chain reaction utilizing a degenerate antisense oligonucleotide PCR primer based on the novel N-terminal amino acid sequence described in Example 2. The sequence of the primer is set out below in IUPAC nomenclature and where "I" is an inosine.

---
SEQ ID NO: 4
5' ACATGAATTCGGIATCYTTIGTYTGICCRAA 3'

---

The codon choice tables of Wada et al., Nuc. Acids Res., 19S: 1981–1986 (1991) were used to select nucleotides at the third position of each codon of the primer. The primer was used in combination with a primer specific for either the SP6 or T7 promoter sequences, both of which flank the cloning site of pRc/CMV, to screen the macrophage library pools of 300,000 clones. All PCR reactions contained 100 ng of template cDNA, 1 μg of each primer, 0.125 mM of each dNTP, 10 mM Tris-HCl pH 8.4, 50 mM MgCl$_2$ and 2.5 units of Taq polymerase. An initial denaturation step of 94° C. for four minutes was followed by 30 cycles of amplification of 1 minute at 94° C., 1 minute at 60° C. and 2 minutes at 72° C. The resulting PCR product was cloned into pBluescript SK$^-$ (Stratagene, La Jolla, Calif.) and its nucleotide sequence determined by the dideoxy chain termination method. The PCR product contained the sequence predicted by the novel peptide sequence and corresponds to nucleotides 1 to 331 of SEQ ID NO: 7.

The PCR primers set out below, which are specific for the cloned PCR fragment described above, were then designed for identifying a full length clone.

---
Sense Primer (SEQ ID NO: 5)
5' TATTCTAGAAGTGTGGTGGAACTCGCTGG 3'
Antisense Primer (SEQ ID NO: 6)
5' CGATGAATTCAGCTTGCAGCAGCCATCAGTAC 3'

---

PCR reactions utilizing the primers were performed as described above to first screen the cDNA pools of 300,000 clones and then the appropriate subset of the smaller pools of 3000 clones. Three pools of 3000 clones which produced a PCR product of the expected size were then used to transform bacteria.

C. Library Screening by Hybridization

DNA from the transformed bacteria was subsequently screened by hybridization using the original cloned PCR fragment as a probe. Colonies were blotted onto nitrocellulose and prehybridized and hybridized in 50% formamide, 0.75M sodium chloride, 0.075M sodium citrate, 0.05M sodium phosphate pH 6.5, 1% polyvinyl pyrolidine, 1% Ficoll, 1% bovine serum albumin and 50 ng/ml sonicated salmon sperm DNA. The hybridization probe was labeled by random hexamer priming. After overnight hybridization at 42° C., blots were washed extensively in 0.03M sodium chloride, 3 mM sodium citrate, 0.1% SDS at 42° C. The nucleotide sequence of 10 hybridizing clones was determined. One of the clones, clone sAH 406-3, contained the sequence predicted by the original peptide sequence of the PAF-AH activity purified from human plasma. The DNA and deduced amino acid sequences of the human plasma PAF-AH are set out in SEQ ID NOs: 7 and 8, respectively.

Clone sAH 406-3 contains a 1.52 kb insert with an open reading frame that encodes a predicted protein of 441 amino acids. At the amino terminus, a relatively hydrophobic segment of 41 residues precedes the N-terminal amino acid (the isoleucine at position 42 of SEQ ID NO: 8) identified by protein microsequencing. The encoded protein may thus have either a long signal sequence or a signal sequence plus an additional peptide that is cleaved to yield the mature functional enzyme. The presence of a signal sequence is one characteristic of secreted proteins. In addition, the protein encoded by clone sAH 406-3 includes the consensus GxSxG motif (amino acids 271–275 of SEQ ID NO: 8) that is believed to contain the active site serine of all known mammalian lipases, microbial lipases and serine proteases. See Chapus et al., Biochimie, 70:1223–1224 (1988) and Brenner, Nature, 334:528–530 (1988).

Table 2 below is a comparison of the amino acid composition of the human plasma PAF-AH of the invention as predicted from SEQ ID NO: 8 and the amino acid composition of the purportedly purified material described by Stafforini et al. (1987), supra.

TABLE 2

| | Clone sAH 406-3 | Stafforini et al. |
|---|---|---|
| Ala | 26 | 24 |
| Asp & Asn | 48 | 37 |
| Cys | 5 | 14 |
| Glu & Gln | 36 | 42 |
| Phe | 22 | 12 |
| Gly | 29 | 58 |
| His | 13 | 24 |
| Ile | 31 | 17 |
| Lys | 26 | 50 |
| Leu | 40 | 26 |
| Met | 10 | 7 |
| Pro | 15 | 11 |
| Arg | 18 | 16 |
| Ser | 27 | 36 |
| Thr | 20 | 15 |
| Val | 13 | 14 |
| Trp | 7 | Not determined |
| Tyr | 14 | 13 |

The amino acid composition of the mature form of the human plasma PAF-AH of the invention and the amino acid composition of the previously purified material that was purportedly the human plasma PAF-AH are clearly distinct.

When alignment of the Hattori et al., supra nucleotide and deduced amino acid sequences of bovine brain cytoplasmic PAF-AH with the nucleotide and amino acid sequences of the human plasma PAF-AH of the invention was attempted, no significant structural similarity in the sequences was observed.

EXAMPLE 4

A putative splice variant of the human PAF-AH gene was detected when PCR was performed on macrophage and stimulated PBMC cDNA using primers that hybridized to the 5' untranslated region (nucleotides 31 to 52 of SEQ ID NO: 7) and the region spanning the translation termination codon at the 3' end of the PAF-AH cDNA (nucleotides 1465 to 1487 of SEQ ID NO: 7). The PCR reactions yielded two bands on a gel, one corresponding to the expected size of the PAF-AH cDNA of Example 3 and the other was about 100 bp shorter. Sequencing of both bands revealed that the larger band was the PAF-AH cDNA of Example 3 while the shorter band lacked exon 2 (Example 5 below) of the PAF-AH sequence which encodes the putative signal and pro-peptide sequences of plasma PAF-AH. The predicted catalytic triad and all cysteines were present in the shorter clone, therefore the biochemical activity of the protein encoded by the clone is likely to match that of the plasma enzyme.

EXAMPLE 5

Genomic human plasma PAF-AH sequences were also isolated. The structure of the PAF-AH gene was determined by isolating lambda and P1 phage clones containing human genomic DNA by DNA hybridization under conditions of high stringency. Fragments of the phage clones were subcloned and sequenced using primers designed to anneal at regular intervals throughout the cDNA clone sAH 406-3. In addition, new sequencing primers designed to anneal to the intron regions flanking the exons were used to sequence back across the exon-intron boundaries to confirm the sequences. Exon/intron boundaries were defined as the points where the genomic and cDNA sequences diverged. These analyses revealed that the human PAF-AH gene is comprised of 12 exons.

Exons 1, 2, 3, 4, 5, 6, and part of 7 were isolated from a male fetal placental library constructed in lamda FIX (Stratagene). Phage plaques were blotted onto nitrocellulose and prehybridized and hybridized in 50% formamide, 0.75M sodium chloride, 75 mM sodium titrate, 50 mM sodium phosphate (pH 6.5), 1% polyvinyl pyrolidine, 1% Ficoll, 1% bovine serum albumin, and 50 ng/ml sonicated salmon sperm DNA. The hybridization probe used to identify a phage clone containing exons 2–6 and part of 7 consisted of the entire cDNA clone sAH 406-3. A clone containing exon 1 was identified using a fragment derived from the 5' end of the cDNA clone (nucleotides 1 to 312 of SEQ ID NO: 7). Both probes were labelled with $^{32}$P by hexamer random priming. After overnight hybridization at 42° C., blots were washed extensively in 30 mM sodium chloride, 3 mM sodium titrate, 0.1% SDS at 42° C. The DNA sequences of exons 1, 2, 3, 4, 5, and 6 along with partial surrounding intron sequences are set out in SEQ ID NOs: 9, 10, 11, 12, 13, and 14, respectively.

The remainder of exon 7 as well as exons 8, 9, 10, 11, and 12 were subcloned from a P1 clone isolated from a human P1 genomic library. P1 phage plaques were blotted onto nitrocellulose and prehybridized and hybridized in 0.75M sodium chloride, 50 mM sodium phosphate (pH 7.4), 5 mM EDTA, 1% polyvinyl pyrolidine, 1% Ficoll, 1% bovine serum albumin, 0.5% SDS, and 0.1 mg/ml total human DNA. The hybridization probe, labeled with $^{32}$P by hexamer random priming, consisted of a 2.6 kb EcoR1 fragment of genomic DNA derived from the 3' end of a lambda clone isolated above. This fragment contained exon 6 and the part of exon 7 present on the phage clone. After overnight hybridization at 65° C., blots were washed as described above. The DNA sequences of exons 7, 8, 9, 10, 11, and 12 along with partial surrounding intron sequences are set out in SEQ ID NOs: 15, 16, 17, 18, 19, and 20, respectively.

EXAMPLE 6

Full length plasma PAF-AH cDNA clones were isolated from mouse and canine spleen cDNA libraries and a partial rodent clone was isolated from a rat thymus cDNA library. The clones were identified by low stringency hybridization (hybridization conditions were the same as described for exons 1 through 6 in Example 5 above except that 20% formamide instead of 50% formamide was used). A 1 kb HindIII fragment of the human PAF-AH sAH 406-3 cDNA clone (nucleotides 309 to 1322 of SEQ ID NO: 7) was used as a probe. In addition, a partial monkey clone was isolated from macaque brain cDNA by PCR using primers based on nucleotides 285 to 303 and 851 to 867 of SEQ ID NO: 7. The nucleotide and deduced amino acid sequences of the mouse, canine, rat, and macaque cDNA clones are set out in SEQ ID NOs: 21, 22, 23, and 24, respectively.

A comparison of the deduced amino acid sequences of the cDNA clones with the human cDNA clone results in the amino acid percentage identity values set out in Table 3 below.

TABLE 3

| | Human | Dog | Mouse |
|---|---|---|---|
| Dog | 80 | | |
| Mouse | 66 | 64 | |
| Monkey | 92 | 82 | 69 |
| Rat | 74 | 69 | 82 |

EXAMPLE 7

To determine whether human plasma PAF-AH cDNA clone sAH 406-3 (Example 3) encodes a protein having PAF-AH activity, the pRc/CMV expression construct was transiently expressed in COS 7 cells. Three days following transfection by a DEAE Dextran method, COS cell media was assayed for PAF-AH activity.

Cells were seeded at a density of 300,000 cells per 60 mm tissue culture dish. The following day, the cells were incubated in DMEM containing 0.5 mg/ml DEAE dextran, 0.1 mM chloroquine and 5-10 µg of plasmid DNA for 2 hours. Cells were then treated with 10% DMSO in phosphate-buffered saline for 1 minute, washed with media and incubated in DMEM containing 10% fetal calf serum previously treated with diisopropyl fluorophosphate (DFP) to inactivate endogenous bovine serum PAF-AH. After 3 days of incubation, media from transfected cells were assayed for PAF-AH activity. Assays were conducted in the presence and absence of either 10 mM EDTA or 1 mM DFP to determine whether the recombinant enzyme was calcium-independent and inhibited by the serine esterase inhibitor DFP as previously described for plasma PAF-AH by Stafforini et al. (1987), supra. Negative controls included cells transfected with pRc/CMV either lacking an insert or having the sAH 406-3 insert in reverse orientation.

PAF-AH activity in transfectant supernatants was determined by the method of Stafforini et al. (1990), supra, with the following modifications. Briefly, PAF-AH activity was determined by measuring the hydrolysis of $^3$H-acetate from [acetyl-$^3$H] PAF (New England Nuclear, Boston, Mass.). The aqueous free $^3$H-acetate was separated from labeled substrate by reversed-phase column chromatography over octadecylsilica gel cartridges (Baker Research Products, Phillipsburg, Pa.). Assays were carried out using 10 µl transfectant supernatant in 0.1M Hepes buffer, pH 7.2, in a reaction volume of 50 µl. A total of 50 pmoles of substrate were used per reaction with a ratio of 1:5 labeled: cold PAF. Reactions were incubated for 30 minutes at 37° C. and stopped by the addition of 40 µl of 10M acetic acid. The solution was then washed through the octadecylsilica gel cartridges which were then rinsed with 0.1M sodium acetate. The aqueous eluate from each sample was collected and counted in a liquid scintillation counter for one minute. Enzyme activity was expressed in counts per minute.

Figure 2:
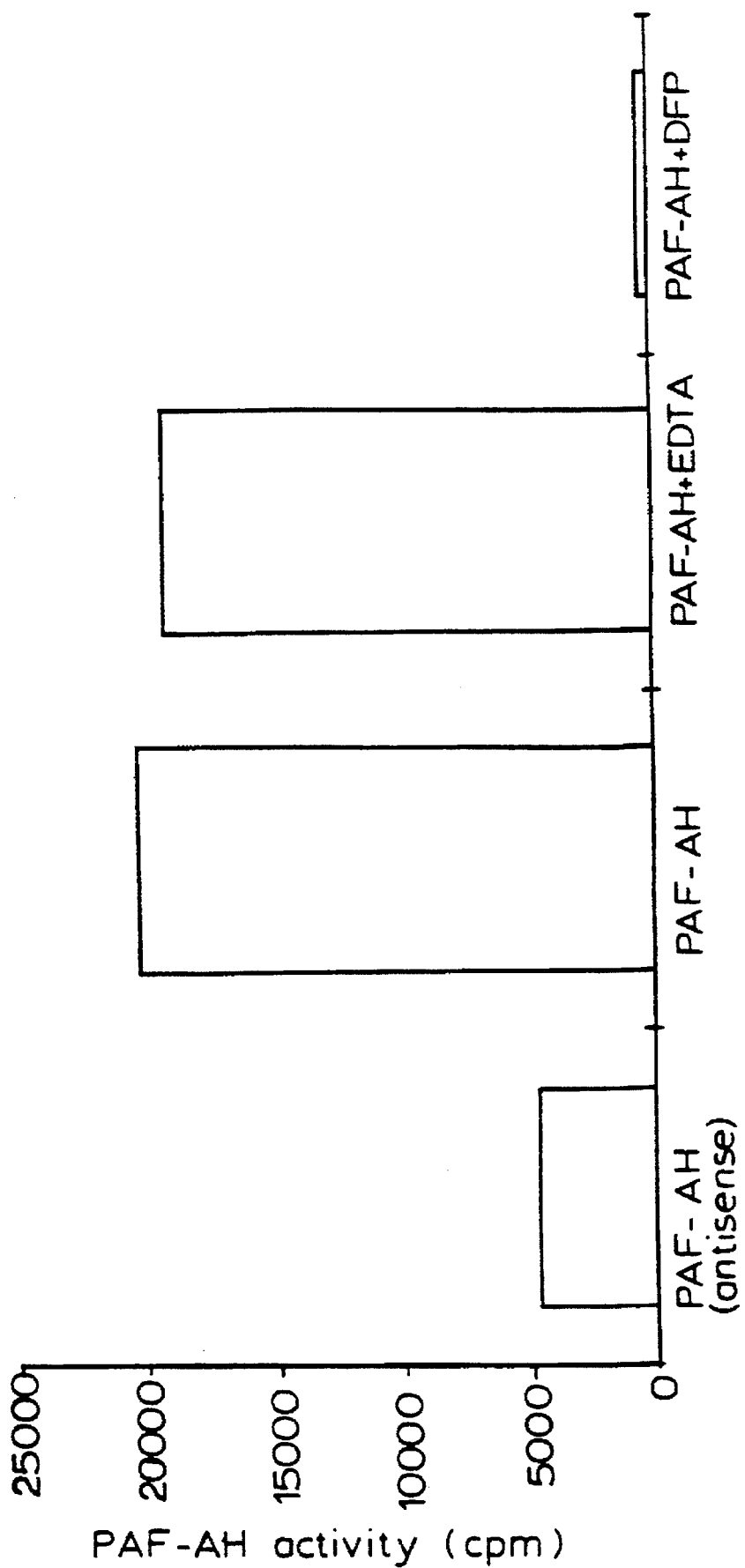
FIG. 2 is a graph showing the enzymatic activity of recombinant human plasma PAF-AH.

As shown in FIG. 2, media from cells transfected with sAH 406-3 contained PAF-AH activity at levels 4-fold greater than background. This activity was unaffected by the presence of EDTA but was abolished by 1 mM DFP. These observations demonstrate that clone sAH 406-3 encodes an activity consistent with the human plasma enzyme PAF-AH.

EXAMPLE 8

PCR was used to generate a protein coding fragment of human plasma PAF-AH cDNA from clone sAH 406-3 which was readily amenable to subcloning into an E. coli expression vector. The subcloned segment began at the 5' end of the human gene with the codon that encodes Ile$_{42}$ (SEQ ID NO: 8), the N-terminal residue of the enzyme purified from human plasma. The remainder of the gene through the native termination codon was included in the construct. The 5' sense PCR primer utilized was:

SEQ ID NO: 25
5' TATTCTAGAATTATGATACAAGTATTAATGGCTGCTGCAAG 3' and contained an XbaI cloning site as well as a translation initiation codon (underscored). The 3' antisense primer utilized was:

SEQ ID NO: 26
5' ATTGATATCCTAATTGTATTTCTCTATTCCTG 3' and encompassed the termination codon of sAH 406-3 and contained an EcoRV cloning site. PCR reactions were performed essentially as described in Example 3. The resulting PCR product was digested with XbaI and EcoRV and subcloned into a pBR322 vector containing the Trp promoter [deBoer et al., PNAS, 80:21-25 (1983)] immediately upstream of the cloning site. E. coli strain XL-1 Blue was transformed with the expression construct and cultured in L broth containing 100 µg/ml of carbenicillin. Transformants from overnight cultures were pelleted and resuspended in lysis buffer containing 50 mM Tris-HCl pH 7.5, 50 mM NaCl, 10 mM CHAPS, 1 mM EDTA, 100 µg/ml lysozyme, and 0.05 trypsin-inhibiting units (TIU)/ml Aprotinin. Following a 1 hour incubation on ice and sonication for 2 minutes, the lysates were assayed for PAF-AH activity by the method described in Example 4. E. coli transformed with the expression construct (designated trp AH) generated a product with PAF-AH activity. See Table 6 in Example 9.

Constructs including three additional promoters, the tacII promoter (deBoer, supra), the arabinose (ara) B promoter from Salmonella typhimurium [Horwitz et al., Gene, 14:309-319 (1981)], and the bacteriophage T7 promoter, were also utilized to drive expression of human PAF-AH sequences in E. coli. Constructs comprising the Trp promoter (pUC trp AH), the tacII promoter (pUC tac AH), and the araB promoter (pUC ara AH) were assembled in plasmid pUC19 (New England Biolabs, MA) while the construct comprising the T7 promoter (pET AH) was assembled in plasmid pET15B (Novagen, Madison, Wis.). A construct containing a hybrid promoters pHAB/PH, consisting of the araB promoter fused to the fibosome binding sites of the T7 promoter region was also assembled in pET15B. All E. coli constructs produced PAF-AH activity within a range of 20 to 50 U/ml/OD$_{600}$. This activity corresponded to a total recombinant protein mass of ≧1% of the total cell protein.

Recombinant human PAF-AH was also been expressed in Saccharomyces cerevisiae. The yeast ADH2 promoter was used to drive rPAF-AH expression and produced 7 U/ml/OD$_{600}$ (Table 4 below).

TABLE 4

| Construct | Promoter | Strain | Enzyme Activity (U/ml/OD) |
|---|---|---|---|
| pUC tac AH | tac | E. coli W3110 | 30 |
| pUC trp AH | trp | E. coli W3110 | 40 |
| pUC ara AH | araB | E. coli W3110 | 20 |
| pET AH | T7 | E. coli BL21 (DE3) (Novagen) | 50 |

TABLE 4-continued

| Construct | Promoter | Strain | Enzyme Activity (U/ml/OD) |
|---|---|---|---|
| pHAB/PH | araB/T7 | E. coli XL-1 | 34 |
| pYep ADH2 AH | ADH2 | Yeast BJ2.28 | 7 |

Several E. coli expression constructs were also evaluated which produce PAF-AH with extended amino termini. The N-terminus of natural plasma PAF-AH was identified as $Ile_{42}$ by amino acid sequencing (Example 2). However, the sequence immediately upstream of $Ile_{42}$ does not conform to amino acids found at signal sequence cleavage sites [i.e., the "−3−1-rule" is not followed, as lysine is not found at position −1; see von Heijne, Nuc. Acids Res., 14:4683–4690 (1986)]. Presumably a more classical signal sequence ($M_1$-$A_{17}$) is recognized by the cellular secretion system, followed by endoproteolytic cleavage. The entire coding sequence for PAF-AH beginning at the initiating methionine (nucleotides 162 to 1487 of SEQ ID NO: 7) was engineered for expression in E. coli using the trp promoter. As shown in Table 5, this construct made active PAF-AH, but expression was at about one fiftieth of the level of the original construct beginning at $Ile_{42}$. Another expression construct, beginning at $Val_{18}$ (nucleotides 213 to 1487 of SEQ ID NO: 7), produced active PAF-AH at about one third the level of the original construct. These results suggest that amino terminal end extensions are not critical or necessary for activity of recombinant PAF-AH produced in E. coli.

TABLE 5

| Construct | PAF-AH activity (U/ml/OD_600) | |
|---|---|---|
| | Lysate | Media |
| pUC trp AH | 177.7 | 0.030 |
| pUC trp AH Met_1 | 3.1 | 0.003 |
| pUC trp AH Val_18 | 54.6 | 0.033 |

EXAMPLE 9

Recombinant human plasma PAF-AH (beginning at $Ile_{42}$) expressed in E. coli was purified to a single Coomassie-stained SDS-PAGE band by various methods and assayed for activities exhibited by the native PAF-AH enzyme.

A. Purification of Recombinant PAF-AH

The first purification procedure utilized is similar to that described in Example 1 for native PAF-AH. The following steps were performed at 4° C. Pellets from 50 ml PAF-AH producing E. coli (transformed with expression construct trp AH) were lysed as described in Example 8. Solids were removed by centrifugation at 10,000 g for 20 minutes. The supernatant was loaded at 0.8 ml/minute onto a Blue Sepharose Fast Flow column (2.5 cm×4 cm; 20 ml bed volume) equilibrated in buffer D (25 mM Tris-HCl, 10 mM CHAPS, 0.5M NaCl, pH 7.5). The column was washed with 100 ml buffer D and eluted with 100 ml buffer A containing 0.5M KSCN at 3.2 ml/minute. A 15 ml active fraction was loaded onto a 1 ml Cu Chelating Sepharose column equilibrated in buffer D. The column was washed with 5 ml buffer D followed by elution with 5 ml of buffer D containing 100 mM imidazole with gravity flow. Fractions containing PAF-AH activity were analyzed by SDS-PAGE.

The results of the purification are shown in Table 6 wherein a unit equals μmol PAF hydrolysis per hour. The purification product obtained at 4° C. appeared on SDS-PAGE as a single intense band below the 43 kDa marker with some diffuse staining directly above and below it. The recombinant material is significantly more pure and exhibits greater specific activity when compared with PAF-AH preparations from plasma as described in Example 1.

TABLE 6

| Sample | Volume (ml) | Activity (units/ml) | Total Act. (units × 10⁵) | Prot Conc (mg/mL) | Specific Activity (units/mg) | % Recovery of Activity | | Fold Purification | |
|---|---|---|---|---|---|---|---|---|---|
| | | | | | | Step | Cum. | Step | Cum. |
| Lysate | 4.5 | 989 | 4451 | 15.6 | 63 | 100 | 100 | 1 | 1 |
| Blue | 15 | 64 | 960 | 0.07 | 914 | 22 | 22 | 14.4 | 14.4 |
| Cu | 1 | 2128 | 2128 | 0.55 | 3869 | 220 | 48 | 4.2 | 61 |

When the same purification protocol was performed at ambient temperature, in addition to the band below the 43 kDa marker, a group of bands below the 29 kDa marker correlated with PAF-AH activity of assayed gel slices. These lower molecular weight bands may be proteolytic fragments of PAF-AH that retain enzymatic activity.

A different purification procedure was also performed at ambient temperature. Pellets (100 g) of PAF-AH-producing E. coli (transformed with the expression construct pUC trp AH) were resuspended in 200 ml of lysis buffer (25 mM Tris, 20 mM CHAPS, 50 mM NaCl, 1 mM EDTA, 50 μg/ml benzamidine, pH 7.5) and lysed by passing three times through a microfluidizer at 15,000 psi. Solids were removed by centrifugation at 14,300×g for 1 hour. The supernatant was diluted 10-fold in dilution buffer [25 mM MES (2-[N-morpholino] ethanesulfonic acid), 10 mM CHAPS, 1 mM EDTA, pH 4.9] and loaded at 25 ml/minute onto an S Sepharose Fast Flow Column (200 ml) (a cation exchange column) equilibrated in Buffer E (25 mM MES, 10 mM CHAPS, 1 mM EDTA, 50 mM NaCl, pH 5.5). The column was washed with 1 liter of Buffer E, eluted with 1M NaCl, and the eluate was collected in 50 ml fractions adjusted to pH 7.5 with 0.5 ml of 2M Tris base. Fractions containing PAF-AH activity were pooled and adjusted to 0.5M NaCl. The S pool was loaded at 1 ml/minute onto a Blue Sepharose Fast Flow column (2.5 cm×4 cm; 20 ml) equilibrated in Buffer F (25 mM Tris, 10 mM CHAPS, 0.5M NaCl, 1 mM EDTA, pH 7.5). The column was washed with 100 ml Buffer F and eluted with 100 ml Buffer F containing 3M NaCl at 4 ml/minute. The Blue Sepharose Fast Flow chromatography step was then repeated to reduce endotoxin levels in the sample. Fractions containing PAF-AH activity were pooled and dialyzed against Buffer G (25 mM Tris pH 7.5, 0.5M NaCl, 0.1% Tween 80, 1 mM EDTA).

The results of the purification are shown in Table 7 wherein a unit equals μmol PAF hydrolysis per hour.

TABLE 7

| Sample | Volume (ml) | Activity (units/ml) | Total Act. (units × 10³) | Prot Conc (mg/mL) | Specific Activity (units/mg) | % Recovery of Activity | | Fold Purification | |
|---|---|---|---|---|---|---|---|---|---|
| | | | | | | Step | Cum. | Step | Cum. |
| Lysate | 200 | 5640 | 1128 | 57.46 | 98 | 100 | 100 | 1 | 1 |
| S | 111 | 5742 | 637 | 3.69 | 1557 | 57 | 56 | 16 | 16 |
| Blue | 100 | 3944 | 394 | 0.84 | 4676 | 35 | 62 | 3 | 48 |

The purification product obtained appeared on SDS-PAGE as a single intense band below the 43 kDa marker with some diffuse staining directly above and below it. The recombinant material is significantly more pure and exhibits greater specific activity when compared with PAF-AH preparations from plasma as described in Example 1.

Yet another purification procedure contemplated by the present invention involves the following cell lysis, clarification, and first column steps. Cells are diluted 1:1 in lysis buffer (25 mM Tris pH 7.5, 150 mM NaCl, 1% Tween 80, 2 mM EDTA). Lysis is performed in a chilled microfluidizer at 15,000–20,000 psi with three passes of the material to yield >99% cell breakage. The lysate is diluted 1:20 in dilution buffer (25 mM Tris pH 8.5, 1 mM EDTA) and applied to a column packed with Q-Sepharose Big Bead chromatography media (Pharmacia) and equilibrated in 25 mM Tris pH 8.5, 1 mM EDTA, 0.015% Tween 80. The eluate is diluted 1:10 in 25 mM MES pH 5.5, 1.2M Ammonium sulfate, 1 mM EDTA and applied to Butyl Sepharose chromography media (Pharmacia) equilibrated in the same buffer. PAF-AH activity is eluted in 25 mM MES pH. 5.5, 0.1% Tween 80, 1 mM EDTA.

B. Activity of Recombinant PAF-AH

The most remarkable property of the PAF acetylhydrolase is its marked specificity for substrates with a short residue at the sn-2 position of the substrate. This strict specificity distinguishes PAF acetylhydrolase from other forms of $PLA_2$. Thus, to determine if recombinant PAF-AH degrades phospholipids with long-chain fatty acids at the sn-2 position, hydrolysis of 1-palmitoyl-2-arachidonoyl-sn-glycero-3-phosphocholine (arachidonoylPC) was assayed since this is the preferred substrate for a well-characterized form of $PLA_2$. As predicted from previous studies with native PAF-AH, this phospholipid was not hydrolyzed when incubated with recombinant PAF-AH. In additional experiments, arachidonoylPC was included in a standard PAF hydrolysis assay at concentrations ranging from 0 to 125 µM to determine whether it inhibited the hydrolysis of PAF by recombinant PAF-AH. There was no inhibition of PAF hydrolysis even at the highest concentration of PAF-AH, which was 5-fold greater than the concentration of PAF. Thus, recombinant PAF-AH exhibits the same substrate selectivity as the native enzyme; long chain substrates are not recognized. Moreover, recombinant PAF-AH enzyme rapidly degraded an oxidized phospholipid (glutaroylPC) which had undergone oxidative cleavage of the sn-2 fatty acid. Native plasma PAF-AH has several other properties that distinguish it from other phospholipases including calcium-independence and resistance to compounds that modify sulfhydryl groups or disrupt disulfides.

Both the native and recombinant plasma PAF-AH enzymes are sensitive to DFP, indicating that a serine comprises part of their active sites. An unusual feature of the native plasma PAF acetylhydrolase is that it is tightly associated with lipoproteins in circulation, and its catalytic efficiency is influenced by the lipoprotein environment. When recombinant PAF-AH of the invention was incubated with human plasma (previously treated with DFP to abolish the endogenous enzyme activity), it associated with low and high density lipoproteins in the same manner as the native activity. This result is significant because there is substantial evidence that modification of low density lipoproteins is essential for the cholesterol deposition observed in atheromas, and that oxidation of lipids is an initiating factor in this process. PAF-AH protects low density lipoproteins from modification under oxidizing conditions in vitro and may have such a role in vivo. Administration of PAF-AH is thus indicated for the supression the oxidation of lipoproteins in atherosclerotic plaques as well as to resolve inflammation.

These results all confirm that the cDNA clone sAH 406-3 encodes a protein with the activities of the the human plasma PAF acetylhydrolase.

EXAMPLE 10

Various other recombinant PAF-AH products were expressed in E. coli. The products included PAF-AH analogs having single amino acid mutations and PAF-AH fragments.

A. PAF-AH Amino Acid Substitution Products

PAF-AH is a lipase because it hydrolyses the phospholipid PAF. While no obvious overall similarity exists between PAF-AH and other characterized lipases, there are conserved residues found in comparisons of structurally characterized lipases. A serine has been identified as a member of the active site. The serine, along with an aspartate residue and a histidine residue, form a catalytic triad which represents the active site of the lipase. The three residues are not adjacent in the primary protein sequence, but structural studies have demonstrated that the three residues are adjacent in three dimensional space. Comparisons of structures of mammalian lipases suggest that the Asp residue is generally twenty-four amino acids C-terminal to the active site serine. In addition, the histidine is generally 109 to 111 amino acids C-terminal to the active site serine.

By site-directed mutagenesis and PCR, individual codons of the human PAF-AH coding sequence were modified to encode alanine residues and were expressed in E. coli. As shown in Table 8 below wherein, for example, the abbreviation "S 108A" indicates that the serine residue at position 273 was changed to an alanine, point mutations of $Ser_{273}$, $Asp_{296}$, or $His_{351}$ completely destroy PAF-AH activity. The distances between active site residues is similar for PAF-AH (Ser to Asp, 23 amino acids; Ser to His, 78 amino acids) and other lipases. These experiments demonstrate that $Ser_{273}$, $Asp_{296}$, and $His_{351}$ are critical residues for activity and are therefore likely candidates for catalytic triad residues. Cysteines are often critical for the functional integrity of proteins because of their capacity to form disulfide bonds. The plasma PAF-AH enzyme contains five cysteines. To determine whether any of the five is critical for enzyme actvity, each cysteine was mutated individually to a serine and the resulting mutants were expressed in E. coli. As shown below in Table 8, a significant but not total loss of PAF-AH activity resulted from the conversion of either $Cys_{229}$ or $Cys_{291}$ to serine. Therefore, these cysteines appear to be necessary for full PAF-AH activity. Other point mutations had little or no effect on PAF-AH catalytic activity. In Table 8, "++++" represent wild type PAF-AH activity of about 40–60 U/ml/ $OD_{600}$, "+++" represents about 20–40 U/ml/$OD_{600}$ activity, "++" represents about 10–20 U/ml/$OD_{600}$ activity, "+" represents 1–10 U/ml/$OD_{600}$ activity, and "–" indicates <1 U/ml/$OD_{600}$ activity.

TABLE 8

| Mutation | PAF-AH activity |
| --- | --- |
| Wild type | ++++ |
| S108A | ++++ |
| S273A | – |
| D296A | – |
| D338A | ++++ |
| H351A | – |
| H395A, H399A | ++++ |
| C67S | +++ |
| C229S | + |
| C291S | + |
| C334S | ++++ |
| C407S | +++ |

B. PAF-AH Fragment Products

Figure 3:
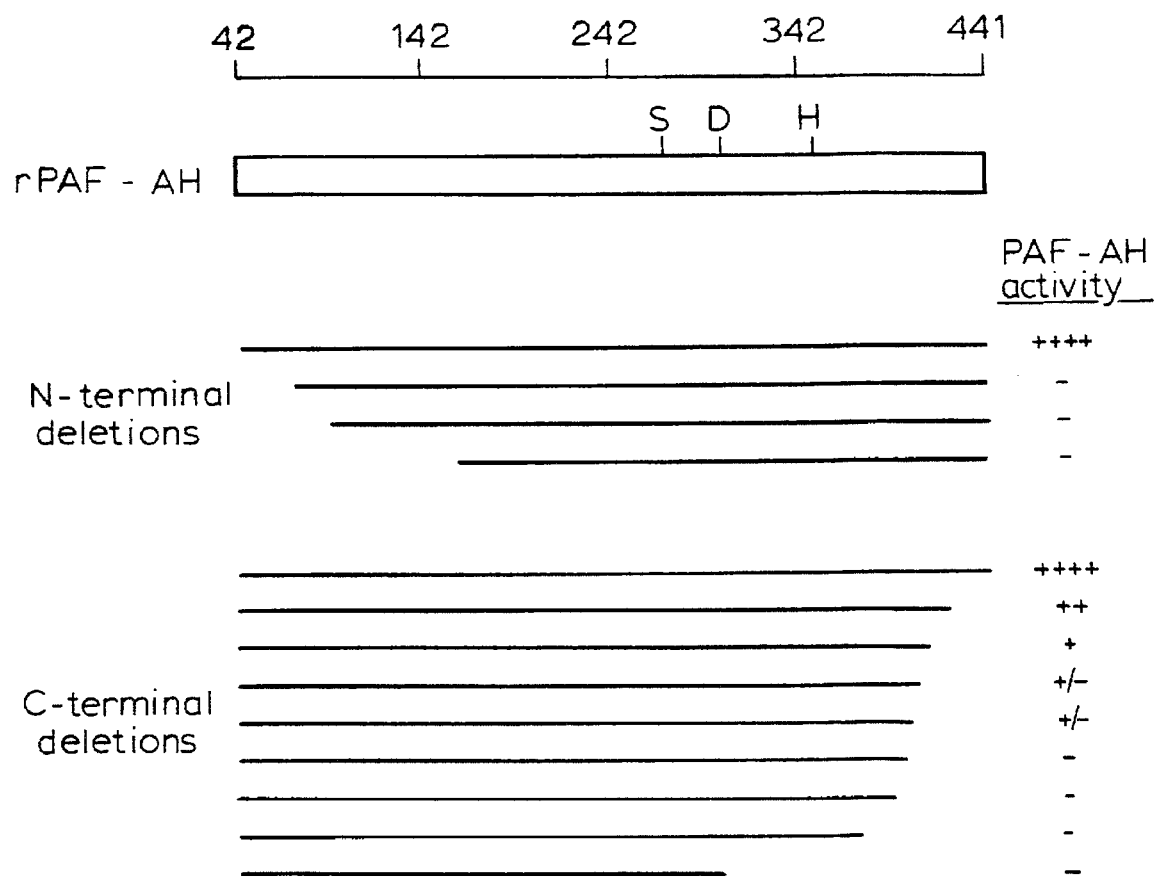
FIG. 3 is a schematic drawing depicting recombinant PAF-AH fragments and their catalytic activity.

C-terminal deletions were prepared by digesting the 3' end of the PAF-AH coding sequence with exonuclease III for various amounts of time and then ligating the shortened coding sequence to plasmid DNA encoding stop codons in all three reading frames. Ten different deletion constructs were characterized by DNA sequence analysis, protein expression, and PAF-AH activity. Removal of twenty-one to thirty C-terminal amino acids greatly reduced catalytic activity and removal of fifty-two residues completely destroyed activity. See FIG. 3.

Similar deletions were made at the amino terminal end of PAF-AH. Fusions of PAF-AH with E. coli thioredoxin at the N-terminus were prepared to facilitate consistent high level expression PAF-AH activity [LaVallie et al., Bio/technology, 11:187–193 (1993)]. Removal of nineteen amino acids from the naturally processed N-terminus ($Ile_{42}$) completely destroyed enzymatic activity in the fusion protein. See FIG. 3.

EXAMPLE 11

A preliminary analysis of expression patterns of human plasma PAF-AH mRNA in human tissues was conducted by Northern blot hybridization.

RNA was prepared from human cerebral cortex, heart, kidney, placenta, thymus and tonsil using RNA Stat 60 (Tel-Test "B", Friendswood, Tex.). Additionally, RNA was prepared from the human hematopoietic precursor-like cell line, THP-1 (ATCC TIB 202), which was induced to differentiate to a macrophage-like phenotype using the phorbol ester phorbolmyristylacetate (PMA). Tissue RNA and RNA prepared from the premyelocytic THP-1 cell line prior to and 1 to 3 days after induction were electrophoresed through a 1.2% agarose formaldehyde gel and subsequently transferred to a nitrocellulose membrane. The full length human plasma PAF-AH cDNA, sAH 406-3, was labelled by random priming and hybridized to the membrane under conditions identical to those described in Example 3 for library screening. Initial results indicate that the PAF-AH probe hybridized to a 1.8 kb band in the thymus, tonsil, and to a lesser extent, the placental RNA.

The expression of PAF-AH RNA in monocytes isolated from human blood and during their spontaneous differentiation into macrophages in culture was also examined. Little or no RNA was detected in fresh monocytes, but expression was induced and maintained during differentiation into macrophages. There was a concomitant accumulation of PAF-AH activity in the culture medium of the differentiating cells. Expression of the human plasma PAF-AH transcript was also observed in the THP-1 cell RNA at 1 day but not 3 days following induction. THP-1 cells did not express mRNA for PAF-AH in the basal state.

EXAMPLE 12

PAF-AH expression in human and mouse tissues was examined by in situ hybridization.

Human tissues were obtained from National Disease Research Interchange and the Cooperative Human Tissue Network. Normal mouse brain and spinal cord, and EAE stage 3 mouse spinal cords were harvested from S/JLJ mice. Normal S/JLJ mouse embryos were harvested from eleven to eighteen days after fertilization.

The tissue sections were placed in Tissue Tek II cryomolds (Miles Laboratories, Inc., Naperville, Ill.) with a small amount of OCT compound (Miles, Inc., Elkhart, Ind.). They were centered in the cryomold, the cryomold filled with OCT compound, then placed in a container with 2-methylbutane $[C_2H_5CH(CH_3)_2$, Aldrich Chemical Company, Inc., Milwaukee, Wis.] and the container placed in liquid nitrogen. Once the tissue and OCT compound in the cryomold were frozen, the blocks were stored at –80° C. until sectioning. The tissue blocks were sectioned at 6 μm thickness and adhered to Vectabond (Vector Laboratories, Inc., Burlingame, Calif.) coated slides and stored at –70° C. and placed at 50° C. for approximately 5 minutes to warm them and remove condensation and were then fixed in 4% paraformaldehyde for 20 minutes at 4° C., alehydrated (70%, 95%, 100% ethanol) for 1 minute at 4° C. in each grade, then allowed to air dry for 30 minutes at room temperature. Sections were denatured for 2 minutes at 70° C. in 70% formamide/2× SSC, rinsed twice in 2× SSC, dehydrated and then air dried for 30 minutes. The tissues were hybridized in situ with radiolabeled single-stranded mRNA generated from DNA derived from an internal 1 Kb HindIII fragment of the PAF-AH gene (nucleotides 308 to 1323 of SEQ ID NO: 7) by in vitro RNA transcription incorporation $^{35}$S-UTP (Amersham). The probes were used at varying lengths from 250–500 bp. Hybridization was carried out overnight (12–16 hours) at 50° C.; the $^{35}$S-labeled riboprobes (6×10$^5$ cpm/section), tRNA (0.5 μg/section) and diethylpyrocarbonate (depc)-treated water were added to hybridization buffer to bring it a final concentration of 50% formamide, 0.3M NaCl, 20 mM Tris pH 7.5, 10% dextran sulfate, 1× Denhardt's solution, 100 mM dithiothretol (DTT) and 5 mM EDTA. After hybridization, sections were washed for 1 hour at room temperature in 4× SSC/10 mM DTT, then for 40 minutes at 60° C. in 50% formamide/1× SSC/10 mM DTT, 30 minutes at room temperature in 2× SSC, and 30 minutes at room temperature in 0.1× SSC. The sections were dehydrated, air dried for 2 hours, coated with Kodak NTB2 photographic emulsion, air dried for 2 hours, developed (after storage at 4° C. in complete darkness) and counterstained with hematoxylin/eosin.

A. Brain

Cerebellum. In both the mouse and the human brains, strong signal was seen in the Purkinje cell layer of the cerebellum, as well as on individual neuronal cell bodies in the dentate nucleus (one of the four deep nuclei in the cerebellum). Additionally, signal was seen on individual cells in the granular and molecular layers of the grey matter.

Hippocampus. In the human hippocampus section, individual cells throughout the section, which appear to be neuronal cell bodies, showed strong signal.

Brain stem. On both human and mouse brain stem sections, there was strong signal on individual cells in the grey matter.

Cortex. On human cortex sections taken from the cerebral, occipital, and temporal cortexes, and on mouse whole brain sections, individual cells throughout the cortex showed strong signal. There does not appear to be differentiation in the expression pattern in the different layers of the cortex. These in situ hybridization results are different from the results for cerebral cortex obtained by Northern blotting. The difference is likely to result from the greater sensitivity of in situ hybridization compared to that of Northern blotting.

Pituitary. Somewhat weak signal was seen on scattered individual cells in the pars distalis of the human tissue section.

B. Human Colon

Both normal and Crohn's disease colons displayed signal in the lymphatic aggregations present in the mucosa of the sections, with the level of signal being slightly higher in the section from the Crohn's disease patient. The Crohn's disease colon also had strong signal in the lamina propria. Similarly, a high level of signal was observed in a diseased appendix section while the normal appendix exhibited a lower but still detectable signal. The sections from the ulcerative colitis patient showed no evident signal in either the lymphatic aggregations or the lamina propria.

C. Human Tonsil and Thymus

Strong signal was seen on scattered groups of individual cells within the germinal centers of the tonsil and within the thymus.

D. Human Lymph Node

Strong signal was observed on the lymph node section taken from a normal donor, while somewhat weak signal was observed in the lymph nodules of the section from a donor with septic shock.

E. Human Small Intestine

Both normal and Crohn's disease small intestine had weak signal in the Peyer's patches and lamina propria in the sections, with the signal on the diseased tissue slightly higher.

F. Human Spleen and Lung

Signal was not observed on any of the spleen (normal and splenic abcess sections) or lung (normal and emphysema sections) tissues.

G. Mouse S.spinal Cord

In both the normal and EAE stage 3 spinal cords, there was strong signal in the grey matter of the spinal cord, with the expression being slightly higher in the EAE stage 3 spinal cord. In the EAE stage 3 spinal cord, cells in the white matter and perivascular cuffs, probably infiltrating macrophages and/or other leukocytes, showed signal which was absent in the normal spinal cord.

F. Mouse Embryos

In the day 11 embryo signal was apparent in the central nervous system in the fourth ventricle, which remained constant throughout the embryo time course as it developed into the cerebellum and brain stem. As the embryos matured, signal became apparent in central nervous system in the spinal cord (day 12), primary cortex and ganglion Gasseri (day 14), and hypophysis (day 16). Signal was observed in the peripheral nervous system (beginning on day 14 or 15) on nerves leaving the spinal cord, and, on day 17, strong signal appeared around the whiskers of the embryo. Expression was also seen in the liver and lung at day 14, the gut (beginning on day 15), and in the posterior portion of the mouth/throat (beginning on day 16). By day 18, the expression pattern had differentiated into signal in the cortex, hindbrain (cerebellum and brain stem), nerves leaving the lumbar region of the spinal cord, the posterior portion of the mouth/throat, the liver, the kidney, and possible weak signal in the lung and gut.

G. Summary

PAF-AH mRNA expression in the tonsil, thymus, lymph node, Peyer's patches, appendix, and colon lymphatic aggregates is consistent with the conclusions that the probable predominant in vivo source of PAF-AH is the macrophage because these tisues all are populated with tissue macrophages that serve as phagocytic and antigen-processing cells.

Expression of PAF-AH in inflamed tissues would be consistent with the hypothesis that a role of monocyte-derived macrophages is to resolve inflammation. PAF-AH would be expected to inactivate PAF and the pro-inflammatory phospholipids, thus down-regulating the inflammatory cascade of events initiated by these mediators.

PAF has been detected in whole brain tissue and is secreted by rat cerebellar granule cells in culture. In vitro and in vivo experiments have demonstrated that PAF binds a specific receptor in neural tissues and induces functional and phenotypic changes such as calcium mobilization, upregulation of transcription activating genes, and differentiation of the neural precursor cell line, PC12. These observations suggested a physiologic role for PAF in the brain, and consistent with this, recent experiments using hippocampal tissue section cultures and PAF analogs and antagonists have implicated PAF as an important retrograde messenger in hippocampal long term potentiation. Therefore, in addition to its pathological effect in inflammation, PAF appears to participate in routine neuronal signalling processes. Expression of the extracellular PAF-AH in the brain may serve to regulate the duration and magnitude of PAF-mediated signalling.

EXAMPLE 13

Monoclonal antibodies specific for recombinant human plasma PAF-AH were generated using *E. coli* produced PAF-AH as an immunogen.

Mouse #1342 was injected on day 0, day 19, and day 40 with recombinant PAF-AH. For the prefusion boost, the mouse was injected with the immunogen in PBS, four days later the mouse was sacrificed and its spleen removed sterilely and placed in 10 ml serum free RPMI 1640. A single-cell suspension was formed by grinding the spleen between the frosted ends of two glass microscope slides submerged in serum free RPMI 1640, supplemented with 2 mM L-glutamine, 1 mM sodium pyruvate, 100 units/ml penicillin, and 100 µg/ml streptomycin (RPMI) (Gibco, Canada). The cell suspension was filtered through sterile 70-mesh Nitex cell strainer (Becton Dickinson, Parsippany, N.J.), and washed twice by centrifuging at 200 g for 5 minutes and resuspending the pellet in 20 ml serum free RPMI. Thymocytes taken from 3 naive Balb/c mice were prepared in a similar manner. NS-1 myeloma cells, kept in log phase in RPMI with 11% fetal bovine serum (FBS) (Hyclone Laboratories, Inc., Logan, Utah) for three days prior to fusion, were centrifuged at 200 g for 5 minutes, and the pellet was washed twice as described in the foregoing paragraph.

One ×10⁸ spleen cells were combined with 2.0×10⁷ NS-1 cells, centrifuged and the supernatant was aspirated. The cell pellet was dislodged by tapping the tube and 1 ml of 37° C. PEG 1500 (50% in 75 mM Hepes, pH 8.0) (Boehringer Mannheim) was added with stirring over the course of 1 minute, followed by adding 7 ml of serum free RPMI over 7 minutes. An additional 8 ml RPMI was added and the cells were centrifuged at 200 g for 10 minutes. After discarding the supernatant, the pellet was resuspended in 200 ml RPMI containing 15% FBS, 100 µM sodium hypoxanthine, 0.4 µM aminopterin, 16 µM thymidine (HAT) (Gibco), 25 units/ml IL-6 (Boehringer Mannheim) and 1.5×10⁶ thymocytes/ml and plated into 10 Corning flat bottom 96 well tissue culture plates (Corning, Corning N.Y.).

On days 2, 4, and 6, after the fusion, 100 µl of medium was removed from the wells of the fusion plates and replaced with fresh medium. On day 8, the fusion was screened by ELISA, testing for the presence of mouse IgG binding to recombinant PAF-AH. Immulon 4 plates (Dynatech, Cambridge, Mass.) were coated for 2 hours at 37° C. with 100 ng/well recombinant PAF-AH diluted in 25 mM TRIS, pH 7.5. The coating solution was aspirated and 200 ul/well of blocking solution [0.5% fish skin gelatin (Sigma) diluted in CMF-PBS] was added and incubated for 30 minutes at 37° C. Plates were washed three times with PBS with 0.05% Tween 20 (PBST) and 50 µl culture supernatant was added. After incubation at 37° C. for 30 minutes, and washing as above, 50 µl of horseradish peroxidase conjugated goat anti-mouse IgG(fc) (Jackson ImmunoResearch, West Grove, Pa.) diluted 1:3500 in PBST was added. Plates were incubated as above, washed four times with PBST and 100 µL substrate, consisting of 1 mg/ml o-phenylene diamine (Sigma) and 0.1 µl/ml 30% $H_2O_2$ in 100 mM Citrate, pH 4.5, was added. The color reaction was stopped in 5 minutes with the addition of 50 µl of 15% $H_2SO_4$. $A_{490}$ was read onn a plate reader (Dynatech).

Selected fusion wells were cloned twice by dilution into 96 well plates and visually scoring the number of colonies/well after 5 days. Hybridomas cloned were 90D1E, 90E3A, 90E6C, 90G11D (ATCC HB 11724), and 90F2D (ATCC HB 11725).

The monoclonal antibodies produced by hybridomas were isotyped using the Isostrip system (Boehringer Mannheim, Indianapolis, Ind.). Results showed that the monoclonal antibodies produced by hybridomas from fusion 90 were all $IgG_1$.

EXAMPLE 14

Experimental studies were performed to evaluate the in vivo therapeutic effects of recombinant PAF-AH of the invention on acute inflammation using a rat foot edema model [Henriques et al., Br. J. Pharmacol, 106:579–582 (1992)]. The results of these studies demonstrated that PAF-AH blocks PAF-induced edema. Parallel studies were done to compare the effectiveness of PAF-AH with two commercially available PAF antagonists.

A. Preparation of PAF-AH

E. coli transformed with the PAF-AH expression vector puc trp AH were lysed in a microfluidizer, solids were centrifuged out and the cell supernatants were loaded onto a S-Sepharose column (Pharmacia). The column was washed extensively with buffer consisting of 50 mM NaCl, 10 mM CHAPS, 25 mM MES and 1 mM EDTA, pH 5.5. PAF-AH was eluted by increasing the NaCl concentration of the buffer to 1M. Affinity chromatography using a Blue Sepharose column (Pharmacia) was then used as an additional purification step. Prior to loading the PAF-AH preparation on the Blue Sepharose column, the sample was diluted 1:2 to reduce the NaCl concentration to 0.5M and the pH was adjusted to 7.5. After washing the Blue Sepharose column extensively with buffer consisting of 0.5M NaCl, 25 mM tris, 10 mM CHAPS and 1 mM EDTA, pH 7.5 the PAF-AH was eluted by increasing the NaCl concentration to 3.0M.

Purity of PAF-AH isolated in this manner was generally 95% as assessed by SDS-PAGE with activity in the range of 5000–10,000 U/ml. Additional quality controls done on each PAF-AH preparation included determining endotoxin levels and hemolysis activity on freshly obtained rat erythrocytes. A buffer containing 25 mM Tris, 10 mM CHAPS, 0.5M NaCl, pH 7.5 functioned as storage media of the enzyme as well as carrier for administration. Dosages used in experiments were based on enzyme activity assays conducted immediately prior to experiments.

B. Induction of Edema

Six to eight-week-old female Long Evans rats (Charles River, Wilmington, Mass.), weighing 180–200 grams, were used for all experiments. Prior to experimental manipulations, animals were anesthetized with a mixture of the anesthetics Ketaset (Port Dodge Laboratories, Fort Dodge, Iowa), Rompun (Miles, Shawnee Mission, Kans.), and Ace Promazine (Aveco, Fort Dodge, Iowa) administered subcutaneously at approximately 2.5 mg Ketaset, 1.6 mg Rompun, 0.2 mg Ace Promazine per animal per dose. Edema was induced in the foot by administration of either PAF or zymosan as follows. PAF (Sigma #P-1402) was freshly prepared for each experiment from a 19.1 mM stock solution stored in chloroform/methanol (9:1) at −20° C. Required volumes were dried down under $N_2$, diluted 1:1000 in a buffer containing 150 mM NaCl, 10 mM Tris pH 7.5, and 0.25% BSA, and sonicated for five minutes. Animals received 50 µl PAF (final dose of 0.96 nmoles) subcutaneously between the hind foot pads, and edema was assessed after 1 hour and again after 2 hours in some experiments. Zymosan A (Sigma #A-8800) was freshly prepared for each experiment as a suspension of 10 mg/ml in PBS. Animals received 50 µl of zymosan (final dose of 500 µg) subcutaneously between the hind foot pads and edema was assessed after 2 hours.

Edema was quantitated by measuring the foot volume immediately prior to administration of PAF or zymosan and at indicated time point post-challenge with PAF or zymosan. Edema is expressed as the increase in foot volume in milliliters. Volume displacement measurements were made on anesthetized animals using a plethysmometer (UGO Basile, model #7150) which measures the displaced water volume of the immersed foot. In order to insure that foot immersion was comparable from one time point to the next, the hind feet were marked in indelible ink where the hairline meets the heel. Repeated measurements of the same foot using this technique indicate the precision to be within 5%.

C. PAF-AH Administration Routes and Dosages

PAF-AH was injected locally between the foot pads, or systematically by IV injection in the tail vein. For local administration rats received 100 µl PAF-AH (4000–6000 U/ml) delivered subcutaneously between the fight hind foot pads. Left feet served as controls by administration of 100 µl carrier (buffered salt solution). For systemic administration of PAF-AH, rats received the indicated units of PAF-AH in 300 µl of carrier administered IV in the tail vein. Controls received the appropriate volume of carrier IV in the tail vein.

D. Local Administration of PAF-AH

Figure 4:
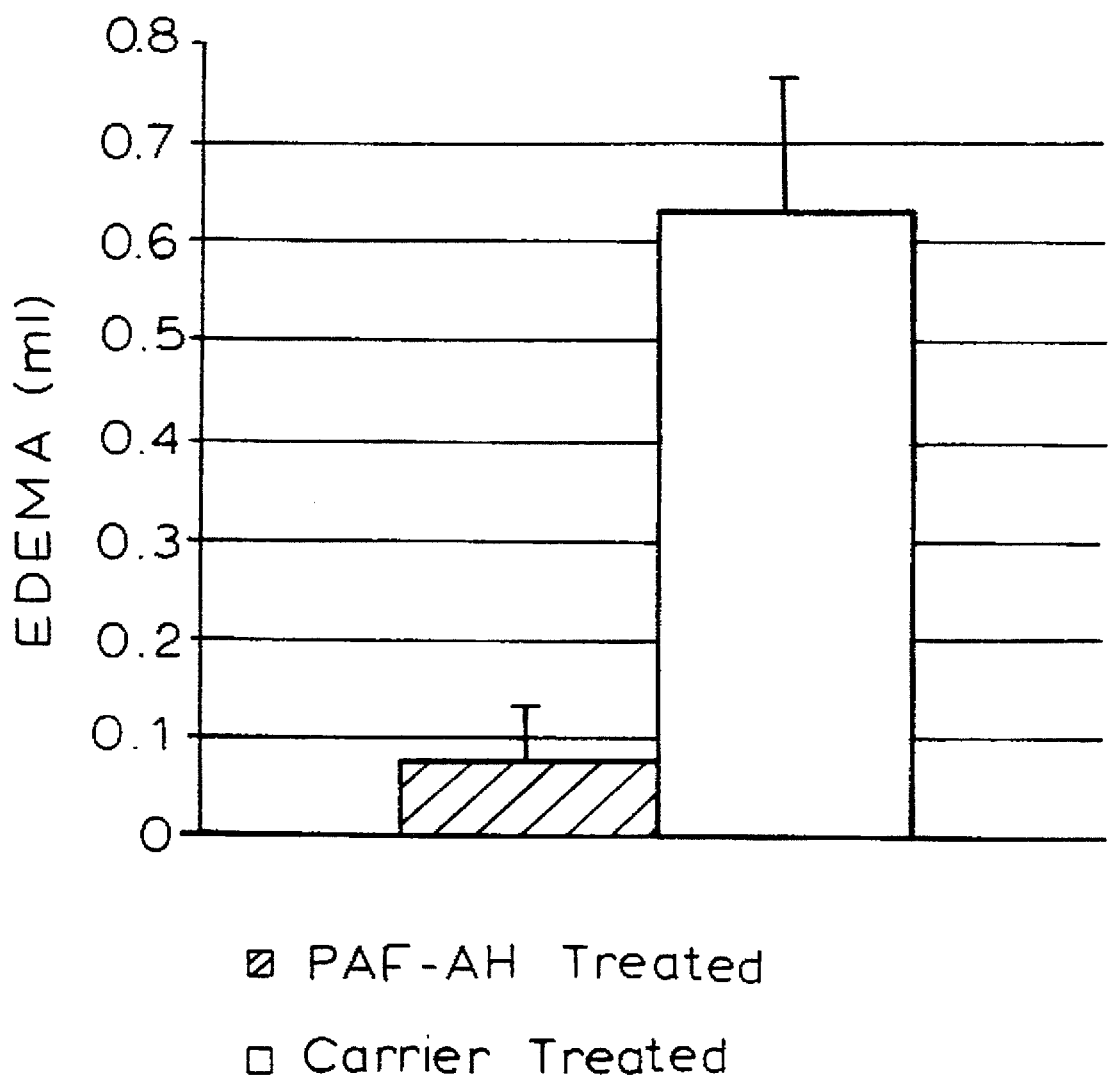
FIG. 4 is a bar graph illustrating blockage of PAF-induced rat foot edema by locally administered recombinant PAF-AH of the invention.

Rats (N=4) were injected with 100 µl of PAF-AH (4000–6000 U/ml) subcutaneously between the fight foot pads. Left feet were injected with 100 µl carrier (buffered salt solution). Four other rats were injected only with carrier. All rats were immediately challenged with PAF via subcutaneous foot injection and foot volumes assessed 1 hour post-challenge. FIG. 4, wherein edema is expressed as average increase in foot volume (ml)±SEM for each treatment group, illustrates that PAF-induced foot edema is blocked by local administration of PAF-AH. The group which received local PAF-AH treatment prior to PAF challenge showed reduced inflammation compared to the control injected group. An increase in foot volume of 0.08 ml±0.08 (SEM) was seen in the PAF-AH group as compared to 0.63±0.14 (SEM) for the carrier treated controls. The increase in foot volume was a direct result of PAF injection as animals injected in the foot only with carrier did not exhibit an increase in foot volume.

E. Intravenous Administration of PAF-AH

Figure 5:
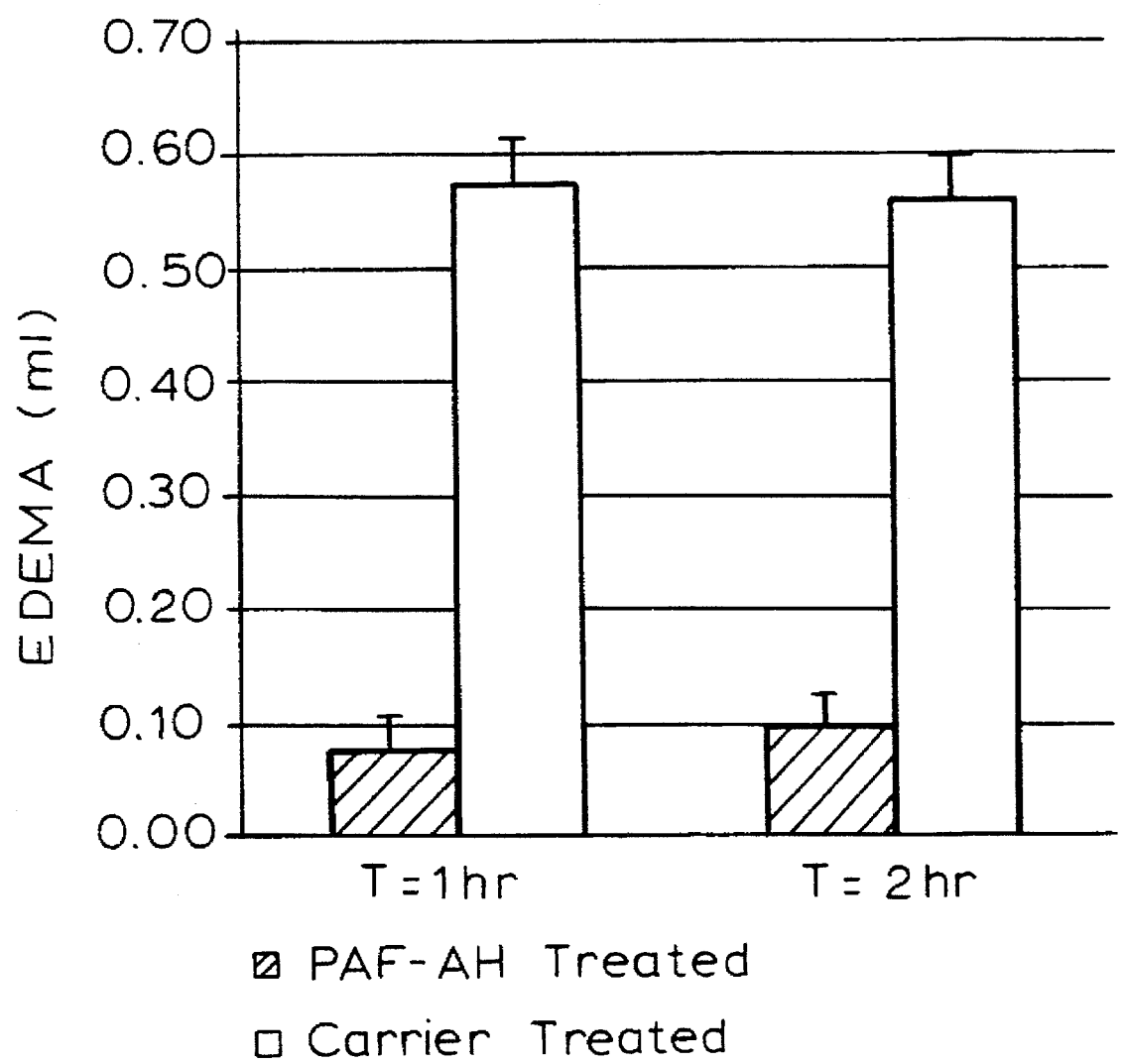
FIG. 5 is a bar graph illustrating blockage of PAF-induced rat foot edema by intravenously administered PAF-AH.

Rats (N=4 per group) were pretreated IV with either PAF-AH (2000 U in 300 µl carrier) or carrier alone, 15 minutes prior to PAF challenge. Edema was assessed 1 and 2 hours after PAF challenge. FIG. 5, wherein edema is expressed as average increase in volume (ml)±SEM for each treatment group, illustrates that IV administration of PAF-AH blocked PAF induced foot edema at one and two hours post challenge. The group which received 2000 U of PAF-AH given by the IV route showed a reduction in inflammation over the two hour time course. Mean volume increase for the PAF-AH treated group at two hours was 0.10 ml±0.08 (SEM), versus 0.56 ml±0.11 for carrier treated controls.

F. Comparison Of PAF-AH Protection in Edema Induced by PAF or Zymosan

Figure 6:
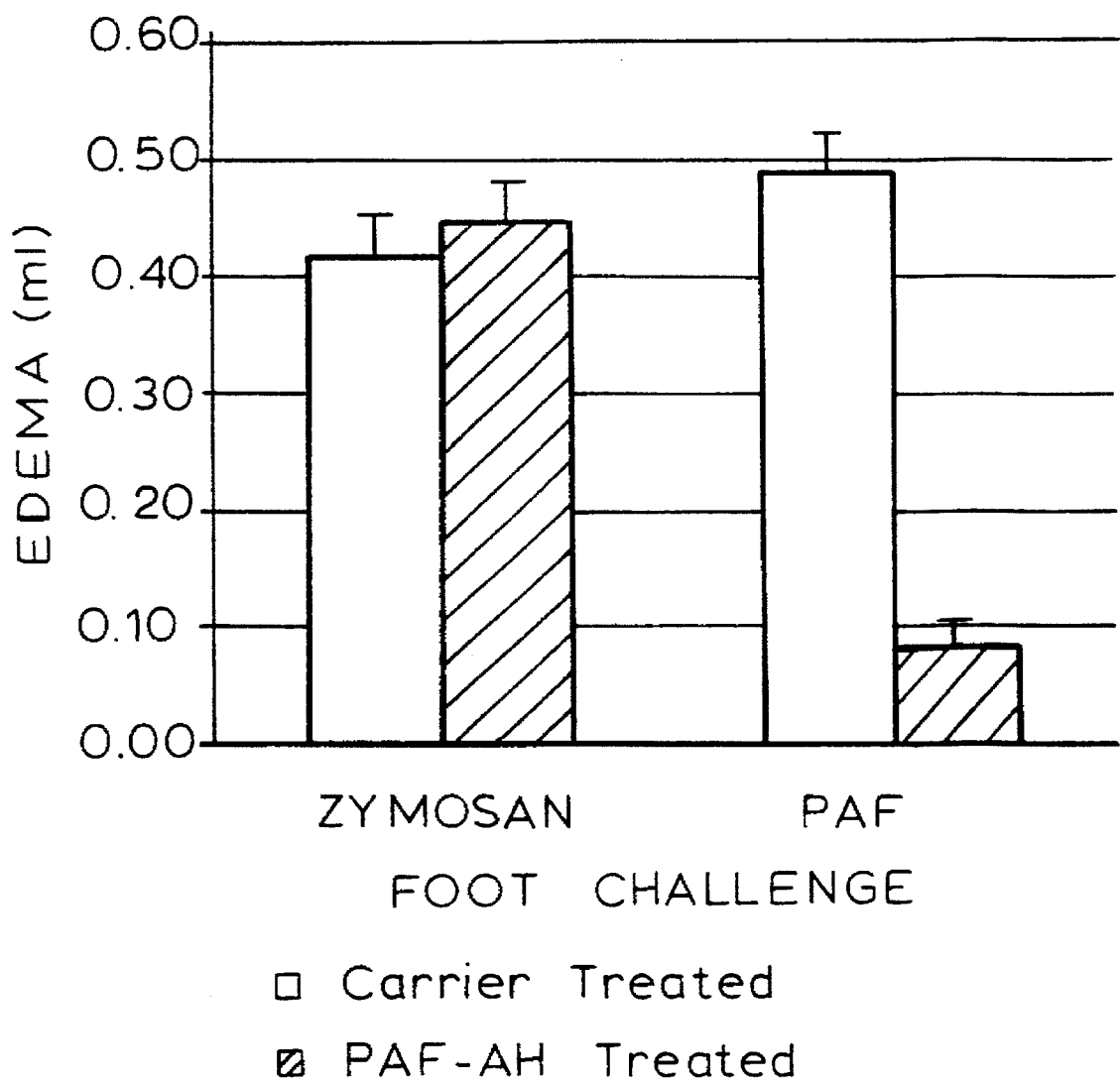
FIG. 6 is a bar graph showing that PAF-AH blocks PAF-induced edema but not zymosan A-induced edema.

Rats (N=4 per group) were pretreated IV with either PAF-AH (2000 U in 300 µl carrier) or carrier alone. Fifteen minutes after pretreatment, groups received either PAF or zymosan A, and foot volume was assessed after 1 and 2 hours, respectively. As shown in FIG. 6, wherein edema is expressed as average increase in volume (ml)±SEM for each treatment group, systemic administration of PAF-AH (2000 U) was effective in reducing PAF-induced foot edema, but failed to block zymosan induced edema. A mean increase in volume of 0.08±0.02 was seen in the PAF-AH treated group versus 0.49±0.03 for the control group.

G. Effective Dose Titration of PAF-AH Protection

Figure 7A:
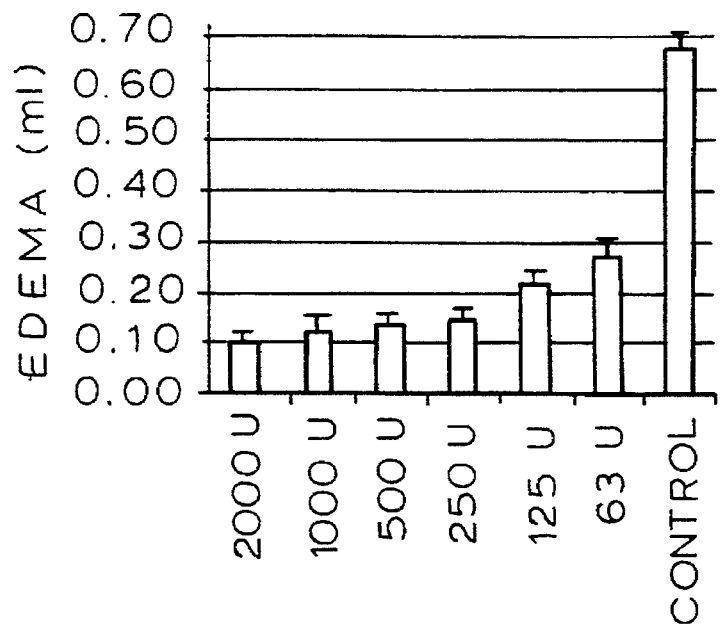
FIGS. 7A and 7B present dose response results of PAF-AH anti-inflammatory activity in rat food edema.
Figure 7B:
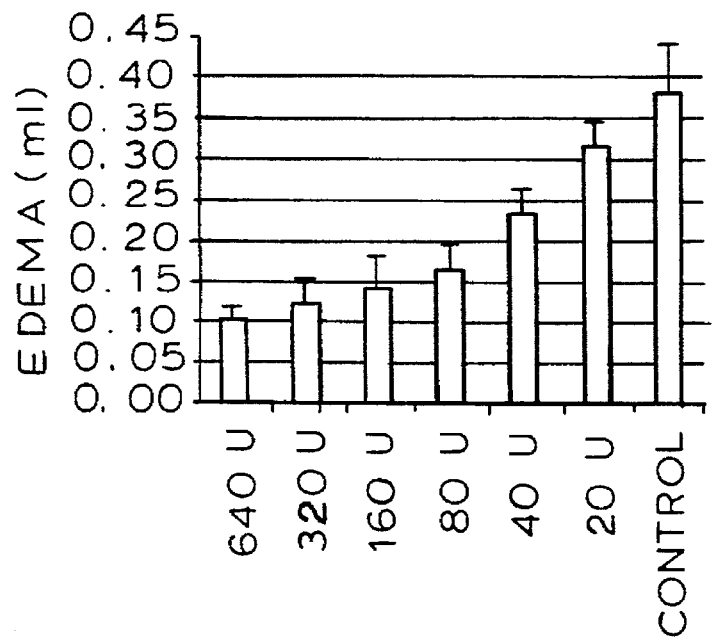

In two separate experiments, groups of rats (N=3 to 4 per group) were pretreated IV with either serial dilutions of PAF-AH or carrier control in a 300 µl volume, 15 minutes prior to PAF challenge. Both feet were challenged with PAF (as described above) and edema was assessed after 1 hour. FIG. 7 wherein edema is expressed as average increase in volume (ml)±SEM for each treatment group, illustrates the increase in protection from PAF-induced edema in rats injected with increasing dosages of PAF-AH. In the experiments, the $ID_{50}$ of PAF-AH given by the IV route was found to be between 40 and 80 U per rat.

H. In Vivo Efficacy of PAF-AH as a Function of Time After Administration

Figure 8A:
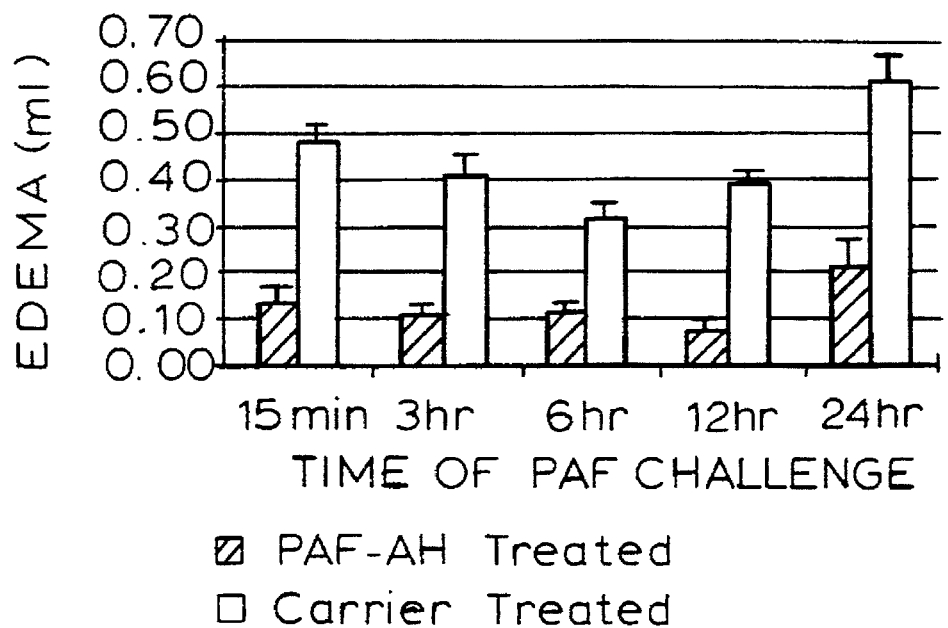
FIGS. 8A and 8B present results indicating the in vivo efficacy of a single dose of PAF-AH over time.
Figure 8B:
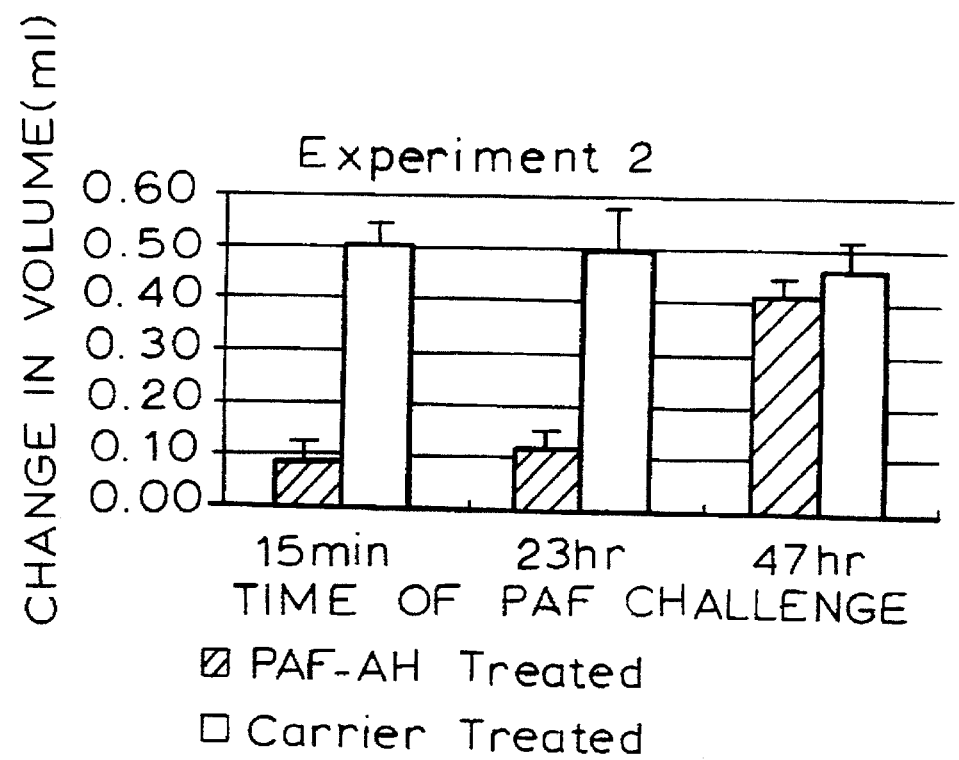

In two separate experiments, two groups of rats (N=3 to 4 per group) were pretreated IV with either PAF-AH (2000 U in 300 µl carrier) or carrier alone. After administration, groups received PAF at time points ranging from 15 minutes to 47 hours post PAF-AH administration. Edema was then assessed 1 hour after PAF challenge. As shown in FIG. 8, wherein edema is expressed as average increase in volume (ml)±SEM for each treatment group, administration of 2000 U of PAF-AH protects rats from PAF induced edema for at least 24 hours.

I. Pharmacokinetics of PAF-AH

Figure 9:
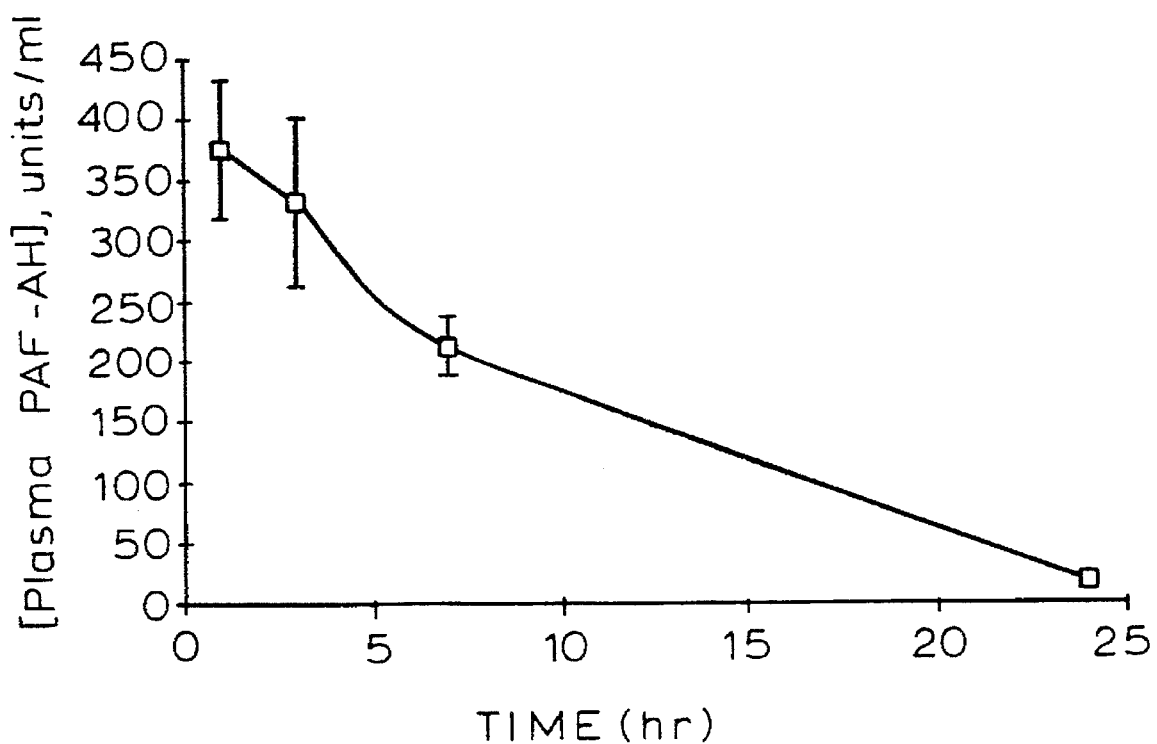
FIG. 9 is a line graph representing the pharmacokinetics of PAF-AH in rat circulation.

Four rats received 2000 U of PAF-AH by IV injection in a 300 µl volume. Plasma was collected at various time points and stored at 4° C. and plasma concentrations of PAF-AH were determined by ELISA using a double mAb capture assay. In brief, monoclonal antibody 90G11D (Example 13) was diluted in 50 mM carbonate buffer pH 9.6 at 100 ng/ml and immobilized on Immulon 4 ELISA plates overnight at 4° C. After extensive washing with PBS containing 0.05% Tween 20, the plates were blocked for 1 hour at room temperature with 0.5% fish skin gelatin (Sigma) diluted in PBS. Serum samples diluted in PBS with 15 mM CHAPS were added in duplicate to the washed ELISA plate and incubated for 1 hour at room temperature. After washing, a biotin conjugate of monoclonal antibody 90F2D (Example 13) was added to the wells at a concentration of 5 µg/ml diluted in PBS and incubated for 1 hour at room temperature. After washing, 50 µl of a 1:1000 dilution of ExtraAvidin (Sigma) was added to the wells and incubated for 1 hour at room temperature. After washing, wells were developed using OPD as a substrate and quantitated. Enzyme activity was then calculated from a standard curve. FIG. 9, wherein data points represent means±SEM, shows that at one hour plasma enzyme levels approached the predicted concentration based on a 5–6 ml plasma volume for 180–200 gram rats, mean=374 U/ml±58.2. Beyond one hour plasma levels steadily declined, reaching a mean plasma concentration of 19.3 U/ml±3.4 at 24 hours, which is still considerably higher than endogenous rat PAF-AH levels which have been found to be approximately 4 U/ml by enzymatic assays.

J. Effectiveness of PAF-AH Versus PAF Antagonists

Figure 10:
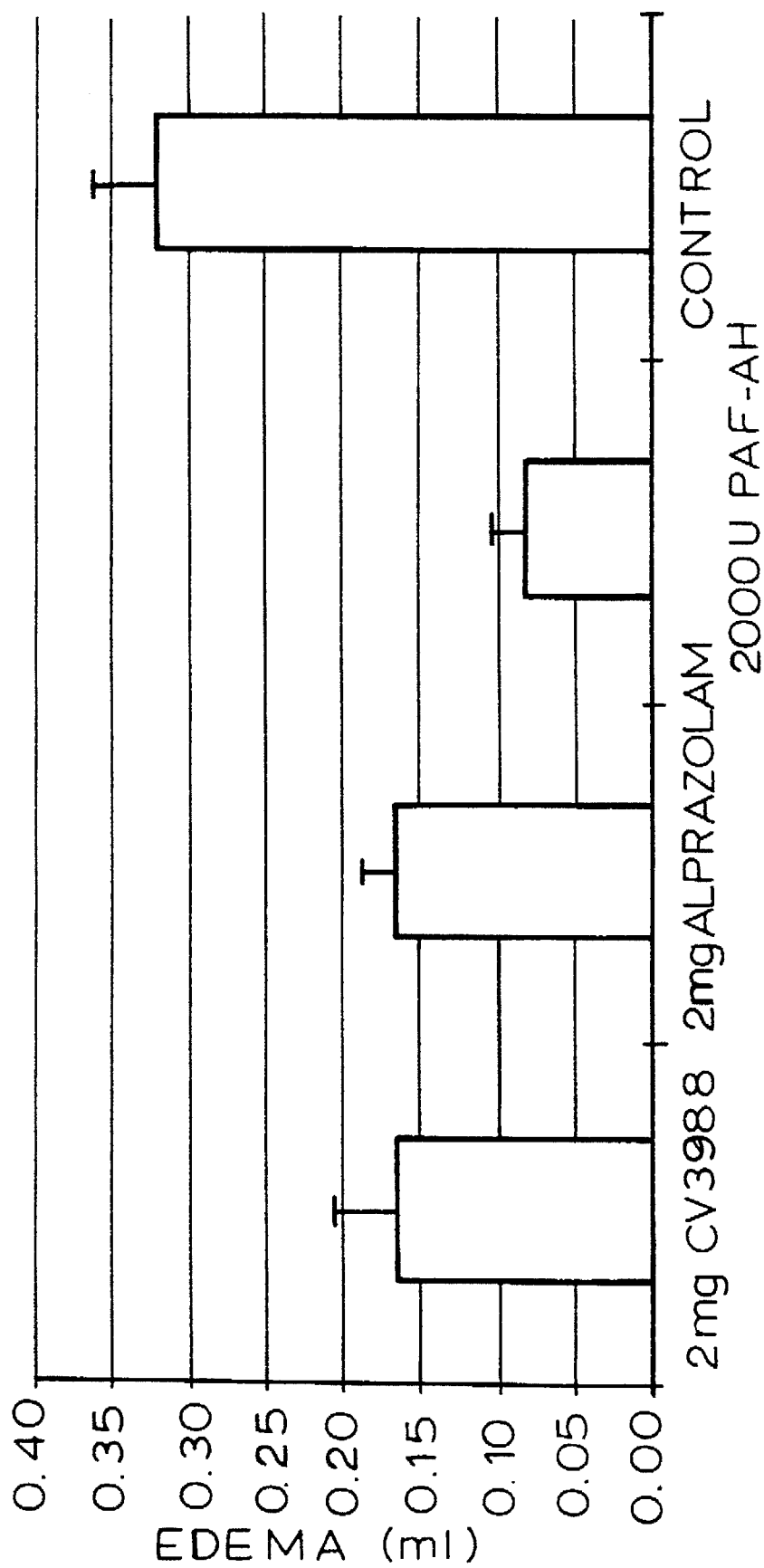
FIG. 10 is a bar graph showing the anti-inflammatory effects of PAF-AH in comparison to the lesser effects of PAF antagonists in rat foot edema.

Groups of rats (N=4 per group) were pretreated with one of three potential antiinflammatories: the PAF antagonist CV3988 (Biomol #L-103) administered IP (2 mg in 200 µl EtOH), the PAF antagonist Alprazolam (Sigma #A-8800) administered IP (2 mg in 200 µl EtOH), or PAF-AH (2000 U) administered IV. Control rats were injected IV with a 300 µl volume of carrier. The PAF antagonists were administered IP because they are solubilized in ethanol. Rats injected with either CV3988 or Alprazolam were challenged with PAF 30 minutes after administration of the PAF antagonist to allow the PAF antagonist to enter circulation, while PAF-AH and carrier-treated rats were challenged 15 minutes after enzyme administration. Rats injected with PAF-AH exhibited a reduction in PAF-induced edema beyond that afforded by the established PAF antagonists CV3988 and Alprazolam. See FIG. 10 wherein edema is expressed as average increase in volume (ml)±SEM for each treatment group.

In summary, PAF-AH is effective in blocking edema mediated by PAF in vivo. Administration of PAF-AH can be either local or systemic by IV injection. In dosing studies, IV injections in the range of 160–2000 U/rat were found to dramatically reduce PAF mediated inflammation, while the $ID_{50}$ dosage appears to be in the range of 40–80 U/rat. Calculations based on the plasma volume for 180–200 gram rats predicts that a plasma concentration in the range of 25–40 U/ml should block PAF-elicited edema. These predictions are supported by preliminary pharmacokinetic studies. A dosage of 2000 U of PAF-AH was found to be effective in blocking PAF mediated edema for at least 24 hours. At 24 hours following administration of PAF-AH plasma concentrations of the enzyme were found to be approximately 25 U/ml. PAF-AH was found to block PAF-induced edema more effectively than the two known PAF antagonists tested.

Collectively, these results demonstrate that PAF-AH effectively blocks PAF induced inflammation and may be of therapeutic value in diseases where PAF is the primary mediator.

EXAMPLE 15

Recombinant PAF-AH of the invention was tested in a second in vivo model, PAF-induced pleurisy. PAF has previously been shown to induce vascular leakage when introduced into the pleural space [Henriques et al., supra]. Female rats (Charles River, 180–200 g) were injected in the tail vein with 200 µl of 1% Evans blue dye in 0.9% with 300 µl recombinant PAF-AH (1500 µmol/ml/hour, prepared as described in Example 14) or with an equivalent volume of control buffer. Fifteen minutes later the rats received an 100 µl injection of PAF (2.0 nmol) into the pleural space. One hour following PAF challenge, rats were sacrificed and the pleural fluid was collected by rinsing the cavity with 3 ml heparinized phosphate buffered saline. The degree of vascular leak was determined by the quantity of Evans blue dye in the pleural space which was quantitated by absorbance at 620 nm. Rats pretreated with PAF-AH were found to have much less vascular leakage than control animals (representing more than an 80% reduction in inflammation).

The foregoing results support the treatment of subjects suffering from pleurisy with recombinant PAF-AH enzyme of the invention.

EXAMPLE 16

Recombinant PAF-AH enzyme of the invention was also tested for efficacy in a model of antigen-induced eosinophil recruitment. The accumulation of eosinophils in the airway is a characteristic feature of late phase immune responses which occur in asthma, rhinitis and eczema. BALB/c mice (Charles River) were sensitized by two intraperitoneal injections consisting of 1 µg of ovalbumin (OVA) in 4 mg of aluminum hydroxide (Imject alum, Pierce Laboratories, Rockford, Ill.) given at a 2 week interval. Fourteen days following the second immunization, the sensitized mice were challenged with either aerosolized OVA or saline as a control.

Prior to challenge mice were randomly placed into four groups, with four mice/group. Mice in groups 1 and 3 were pretreated with 140 µl of control buffer consisting of 25 mM tris, 0.5M NaCl, 1 mM EDTA and 0.1% Tween 80 given by intravenous injection. Mice in groups 2 and 4 were pretreated with 750 units of PAF-AH (activity of 5,500 units/ml given in 140 µl of PAF-AH buffer). Thirty minutes following administration of PAF-AH or buffer, mice in groups 1 and 2 were exposed to aerosolized PBS as described below, while mice in groups 3 and 4 were exposed to aerosolized OVA. Twenty-four hours later mice were treated a second time with either 140 µl of buffer (groups 1 and 3) or 750 units of PAF-AH in 140 µl of buffer (groups 2 and 4) given by intravenous injection.

Eosinophil infiltration of the trachea was induced in the sensitized mice by exposing the animals to aerosolized OVA. Sensitized mice were placed in 50 ml conical centrifuge tubes (Corning) and forced to breath aerosolized OVA (50 mg/ml) dissolved in 0.9% saline for 20 minutes using a nebulizer (Model 646, DeVilbiss Corp., Somerset, Pa.). Control mice were treated in a similar manner with the exception that 0.9% saline was used in the nebulizer. Forty-eight hours following the exposure to aerosolized OVA or saline, mice were sacrificed and the tracheas were excised. Tracheas from each group were inbeded in OCT and stored at −70° until sections were cut.

To evaluate eosinophil infiltration of the trachea, tissue sections from the four groups of mice were stained with either Luna solution and hematoxylin-eosin solution or with peroxidase. Twelve 6 µm thick sections were cut from each group of mice and numbered accordingly. Odd numbered sections were stained with Luna stain as follows. Sections were fixed in formal-alcohol for 5 minutes at room temperature, rinsed across three changes of tap water for 2 minutes at room temperature then rinsed in two changed of $dH_2O$ for 1 minute at room temperature. Tissue sections were stained with Luna stain 5 minutes at room temperature (Luna stain consisting of 90 mi Weigert's Iron hematoxylin and 10 ml of 1% Biebrich Scarlet). Stained slides were dipped in 1% acid alcohol six times, rinsed in tap water for 1 minute at room temperature, dipped in 0.5% lithium carbonate solution five times and rinsed in running tap water for 2 minutes at room temperature. Slides were dehydrated across 70%–95%–100% ethanol 1 minute each, at room temperature, then cleared in two changes of xylene for 1 minute at room temperature and mounted in Cytoseal 60.

For the peroxidase stain, even numbered sections were fixed in 4° C. acetone for 10 minutes and allowed to air dry. Two hundred µl of DAB solution was added to each section and allowed to sit 5 minutes at room temperature. Slides were rinsed in tap water for 5 minutes at room temperature and 2 drops of 1% osmic acid was applied to each section for 3–5 seconds. Slides were rinsed in tap water for 5 minutes at room temperature and counterstained with Mayers hematoxylin at 25° C. at room temperature. Slides were then rinsed in running tap water for 5 minutes and dehydrated across 70%–95%–100% ethanol 1 minute each at room temperature. Slides were cleared through two changes of xylene for 1 minute each at room temperature and mounted in Cytoseal 60.

The number of eosinophils in the submucosal tissue of the trachea was evaluated. Trachea from mice from groups 1 and 2 were found to have very few eosinophils scattered throughout the submucosal tissue. As expected tracheas from mice in group 3, which were pretreated with buffer and exposed to nebulized OVA, were found to have large numbers of eosinophils throughout the submucosal tissue. In contrast, the tracheas from mice in group 4, which were pretreated with PAF-AH and exposed to nebulized OVA were found to have very few eosinophils in the submucosal tissue comparable to what was seen in the two control groups, groups 1 and 2.

Thus, therapeutic treatment with PAF-AH of subjects exhibiting a late phase immune response involving the accumulation of eosinophils in the airway, such as that which occurs in asthma, rhinitis, and eczema, is indicated.

EXAMPLE 17

Nearly four percent of the Japanese population has low or undetectable levels of PAF-AH activity in their plasma. This deficiency has been correlated with severe respiratory symptoms in asthmatic children [Miwa et al., *J. Clin. Invest,.* 82:1983–1991 (1988)] who appear to have inherited the deficiency in an autosomal recessive manner.

To determine if the deficiency arises from an inactive but present enzyme or from an inability to synthesize PAF-AH, plasma from multiple patients deficient in PAF-AH activity was assayed both for PAF-AH activity (by the method described in Example 10 for transfectants) and for the presence of PAF-AH using the monoclonal antibodies 90G11D and 90F2D (Example 13) in a sandwich ELISA as follows. Immulon 4 flat bottom plates (Dynatech, Chantilly, Va.) were coated with 100 ng/well of monoclonal antibody 90G11D and stored overnight. The plates were blocked for 1 hour at room temperature with 0.5% fish skin gelatin (Sigma) diluted in CMF-PBS and then washed three times.

Patient plasma was diluted in PBS containing 15 mM CHAPS and added to each well of the plates (50 μl/well). The plates were incubated for 1 hour at room temperature and washed four times. Fifty μl of 5 μg/ml monoclonal antibody 90F2D, which was biotinylated by standard methods and diluted in PBST, was added to each well, and the plates were incubated for 1 hour at room temperature and then washed three times. Fifty μl of ExtraAvidin (Sigma) diluted 1/1000 in CMF-PBST was subsequently added to each well and plates were incubated for 1 hour at room temperature before development.

A direct correlation between PAF-AH activity and enzyme levels was observed. An absence of activity in a patient's serum was reflected by an absence of detectable enzyme. Similarly, plasma samples with half the normal activity contained half the normal levels of PAF-AH. These observations suggested that the deficiency of PAF-AH activity was due to an inability to synthesize the enzyme or due to an inactive enzyme which the monoclonal antibodies did not recognize.

Further experiments revealed that the deficiency was due to a genetic lesion in the human plasma PAF-AH gene. Genomic DNA from PAF-AH deficient individuals was isolated and used as template for PCR reactions with PAF-AH gene specific primers. Each of the coding sequence exons were initially amplified and sequenced from one individual. A single nucleotide change within exon 9 was observed (a G to T at position 996 of SEQ ID NO: 7). The nucleotide change results in an amino acid substitution of a phenylalanine for a valine at position 279 of the PAF-AH sequence (V279F). Exon 9 was amplified from genomic DNA from an additional eleven PAF-AH deficient individuals who were found to have the same point mutation.

To test whether this mutation crippled the enzyme, an *E. coli* expression construct containing the mutation was generated by methods similar to that described in Example 10. When introduced into *E. coli*, the expression construct generated no PAF-AH activity while a control construct lacking the mutation was fully active. This amino acid substitution presumably results in a structural modification which causes the observed deficiency of activity and lack of immunoreactivity with the PAF-AH antibodies of the invention.

PAF-AH specific antibodies of the invention may thus be used in diagnostic methods to detect abnormal levels of PAF-AH in serum (normal levels are about 1 to 5 U/ml) and to follow the progression of treatment of pathological conditions with PAF-AH. Moreover, identification of a genetic lesion in the PAF-AH gene allows for genetic screening for the PAF-AH deficiency exhibited by the Japanese patients. The mutation causes the gain of a restriction endonuclease site (Mae II) and thus allows for the simple method of Restriction Fragment Length Polymorphism (RFLP) analysis to differentiate between active and mutant alleles. See Lewin, pp. 136–141 in *Genes V*, Oxford University Press, New York, N.Y. (1994).

Screening of genomic DNA from twelve PAF-AH deficient patients was carried out by digestion of the DNA with MaeII, Southern blotting, and hybridization with an exon 9 probe (nucleotides 1–396 of SEQ ID NO: 17). All patients were found to have RFLPs consistent with the mutant allele.

While the present invention has been described in terms of specific embodiments, it is understood that variations and modifications will occur to those skilled in the art. Accordingly, only such limitations as appear in the appended claims should be placed on the invention.

---

We claim:

1. A purified and isolated PAF-AH polypeptide comprising the human plasma PAF-AH amino acid sequence set out in SEQ ID NO: 8.

2. A purified and isolated PAF-AH polypeptide comprising amino acids 42 to 441 of SEQ ID NO: 8.

* * * * *

UNITED STATES PATENT AND TRADEMARK OFFICE
CERTIFICATE OF CORRECTION

PATENT NO. : 5,641,669
DATED : June 24, 1997
INVENTOR(S) : Cousens et al.

It is certified that error appears in the above-identified patent and that said Letters Patent is hereby corrected as shown below:

Column 5, line 32 replace "Kapecchi" with --Capecchi--;

Column 6, line 29 delete ")";

Column 9, line 28 replace "titrate" with --citrate--;

Column 12, line 34 replace "titrate" with --citrate--;

Column 14, line 3 replace "titrate" with --citrate--;

Column 14, line 14 replace "titrate" with --citrate--;

Column 16, line 39 replace "promoters" with --promoter--;

Column 16, line 40 replace "fibosome" with --ribosome--;

Column 20, line 25 replace "the" after suppression with --of--;

Column 21, line 30 replace "HI" with --III--;

Column 26, line 23 replace "Port" with --Fort--;

Column 26, line 59 replace "fight" with --right--;

UNITED STATES PATENT AND TRADEMARK OFFICE
CERTIFICATE OF CORRECTION

PATENT NO. : 5,641,669
DATED : June 24, 1997
INVENTOR(S) : Cousens et al.

It is certified that error appears in the above-identified patent and that said Letters Patent is hereby corrected as shown below:

Column 26, line 67 replace "fight" with --right--;

Signed and Sealed this

Twenty-ninth Day of August, 2000

Attest:

Q. TODD DICKINSON

*Attesting Officer*           *Director of Patents and Trademarks*